(12) United States Patent
Hickingbotham et al.

(10) Patent No.: US 9,381,111 B2
(45) Date of Patent: Jul. 5, 2016

(54) DELIVERY AND EXTRACTION DEVICES

(76) Inventors: Dyson Hickingbotham, Wake Forest, NC (US); Norman Radtke, Louisville, KY (US)

(*) Notice: Subject to any disclaimer, the term of this patent is extended or adjusted under 35 U.S.C. 154(b) by 954 days.

(21) Appl. No.: 13/525,336

(22) Filed: Jun. 17, 2012

(65) Prior Publication Data

US 2013/0178822 A1 Jul. 11, 2013

Related U.S. Application Data

(63) Continuation of application No. PCT/US2010/060622, filed on Dec. 16, 2010.

(60) Provisional application No. 61/286,788, filed on Dec. 16, 2009.

(51) Int. Cl.
| | | |
|---|---|---|
| *A61F 9/00* | (2006.01) | |
| *A61B 17/34* | (2006.01) | |
| *A61M 5/142* | (2006.01) | |
| *A61M 1/12* | (2006.01) | |
| *A61F 9/007* | (2006.01) | |

(52) U.S. Cl.
CPC ............ *A61F 9/0017* (2013.01); *A61B 17/3468* (2013.01); *A61F 9/00781* (2013.01); *A61M 1/12* (2013.01); *A61M 5/14276* (2013.01)

(58) Field of Classification Search
CPC .............. A61B 17/3468; A61F 9/0017; A61F 9/00781; A61F 2/167; A61M 1/12; A61M 5/14276; A61M 27/002; A61M 37/0069; A61M 2205/04
See application file for complete search history.

(56) References Cited

U.S. PATENT DOCUMENTS

| | | | | |
|---|---|---|---|---|
| 2,463,149 | A * | 3/1949 | Caine ................ | A61M 16/0488 128/200.26 |
| 5,047,008 | A * | 9/1991 | de Juan, Jr. ......... | A61F 9/00763 600/564 |
| 5,634,910 | A * | 6/1997 | Kanner ............. | A61M 25/1018 604/208 |
| 6,159,218 | A * | 12/2000 | Aramant ............. | A61F 9/00727 128/897 |
| 6,886,565 | B2 * | 5/2005 | Morris ...................... | A61F 9/04 128/846 |
| 7,753,916 | B2 * | 7/2010 | Weber ..................... | A61F 2/167 606/107 |
| 2008/0188877 | A1 * | 8/2008 | Hickingbotham ..... | A61B 17/29 606/162 |
| 2010/0211079 | A1 * | 8/2010 | Aramant ............... | A61F 9/0017 606/107 |

* cited by examiner

*Primary Examiner* — Quynh-Nhu H Vu
(74) *Attorney, Agent, or Firm* — The Fedde Law Firm; Kenton Fedde; Nathaniel Fedde

(57) ABSTRACT

This invention provides a device for delivering substances such as medical implants and tissues. The device comprises a mandrel and a mandrel guide whereby substances are delivered by retracting the mandrel guide relative to the mandrel. Included among the various embodiments are devices specialized for delivering retinal pigment epithelial (RPE) cells or nanoplates containing RPE cells to the retina, devices with precise control of delivery, devices with specialized mandrels and/or nozzles, and multifunctional devices adapted to provide additional functions such as infusion and/or suction, illumination, and diathermy.

22 Claims, 43 Drawing Sheets

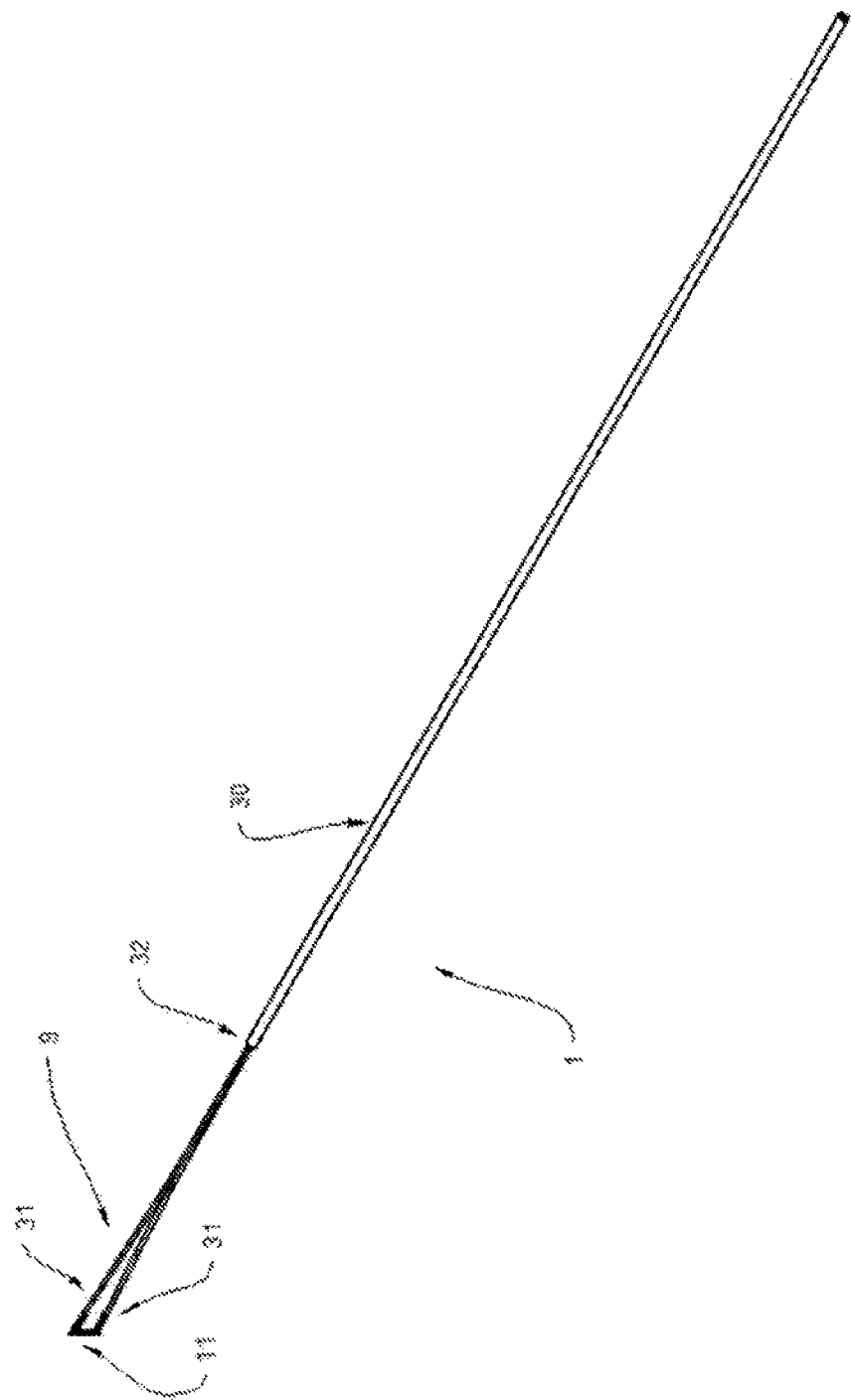

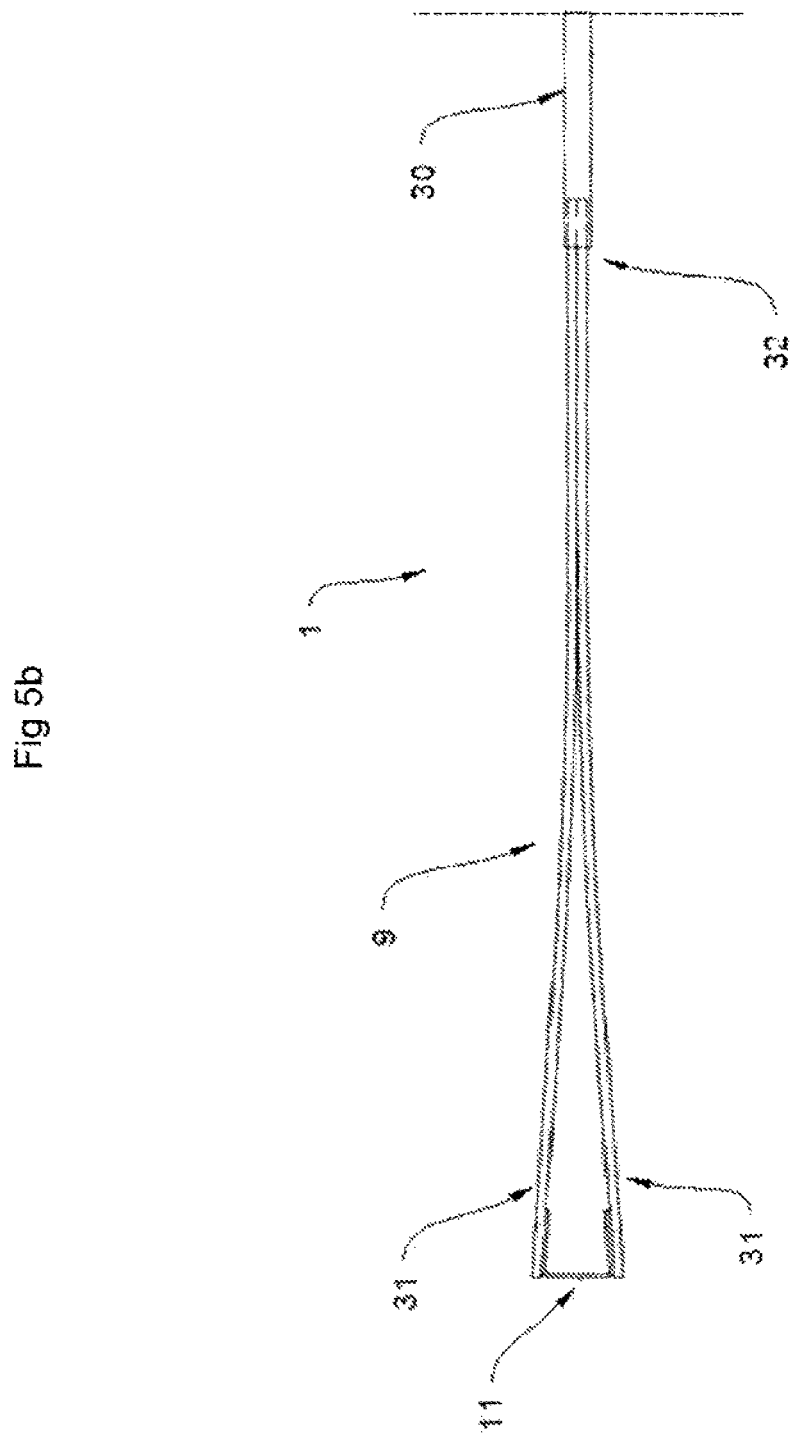

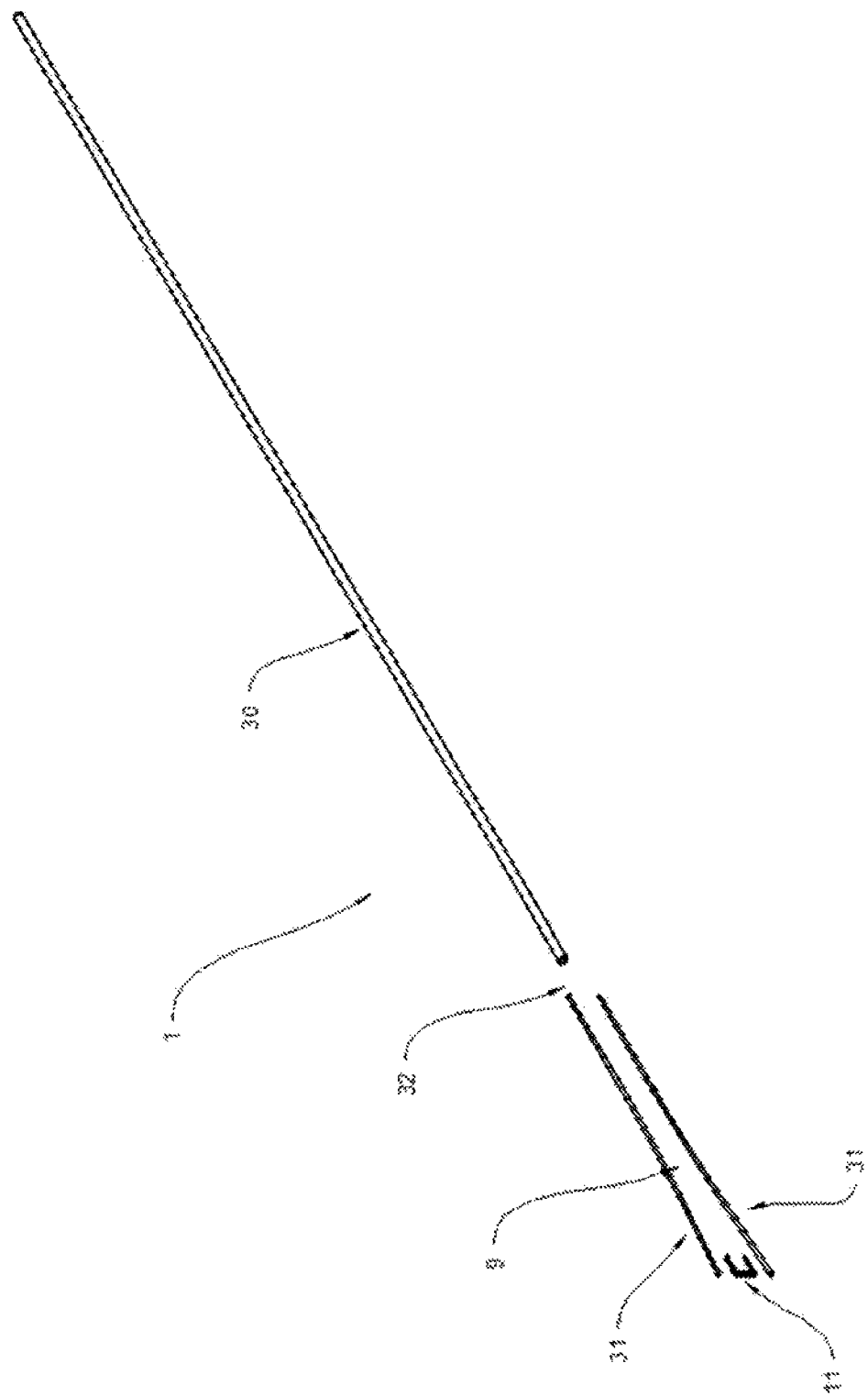

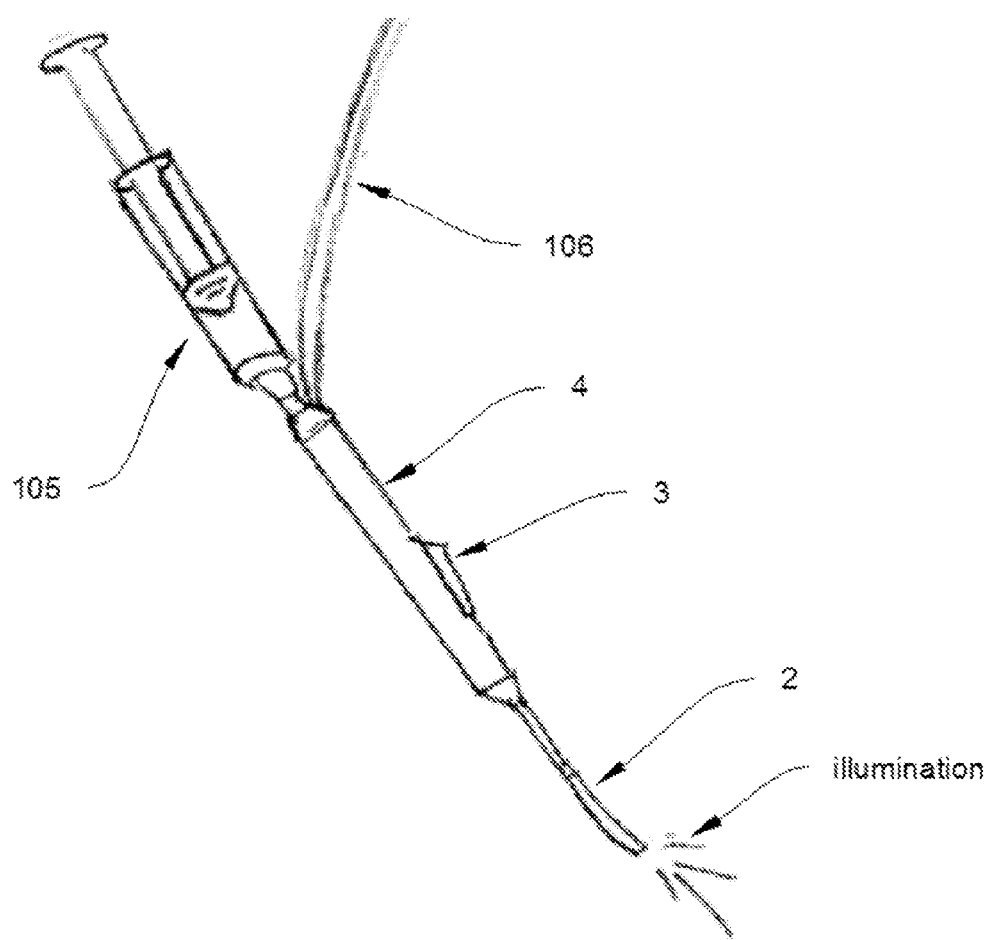

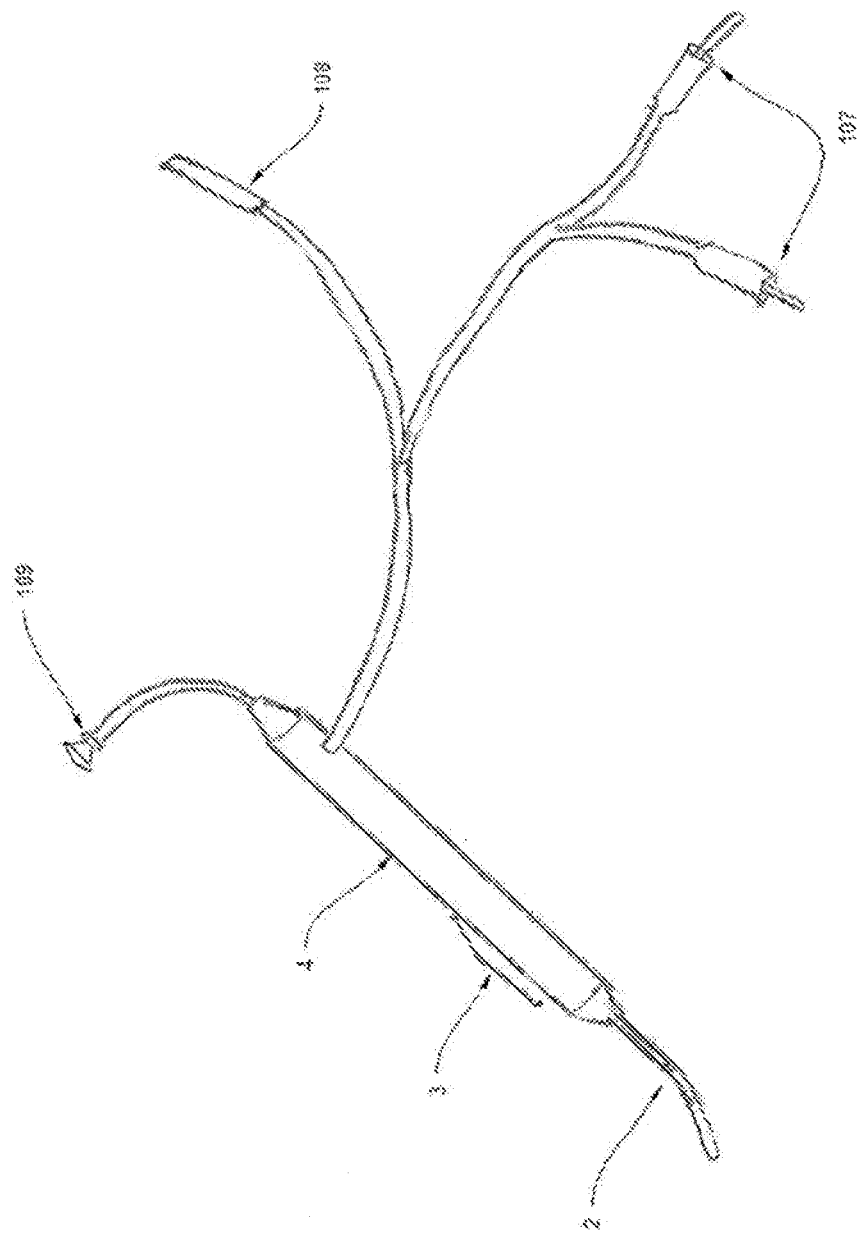

FIG. 18b
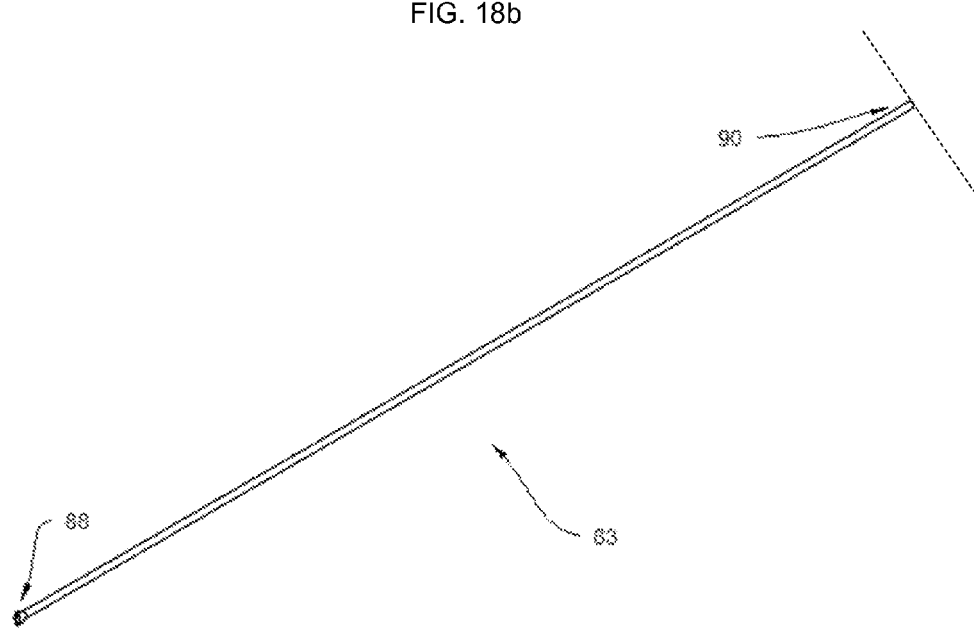
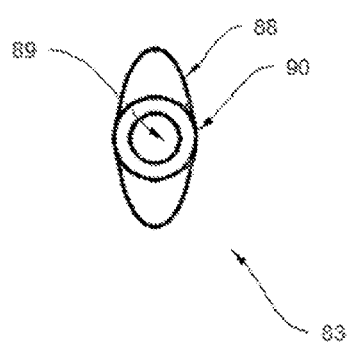
FIG. 18c

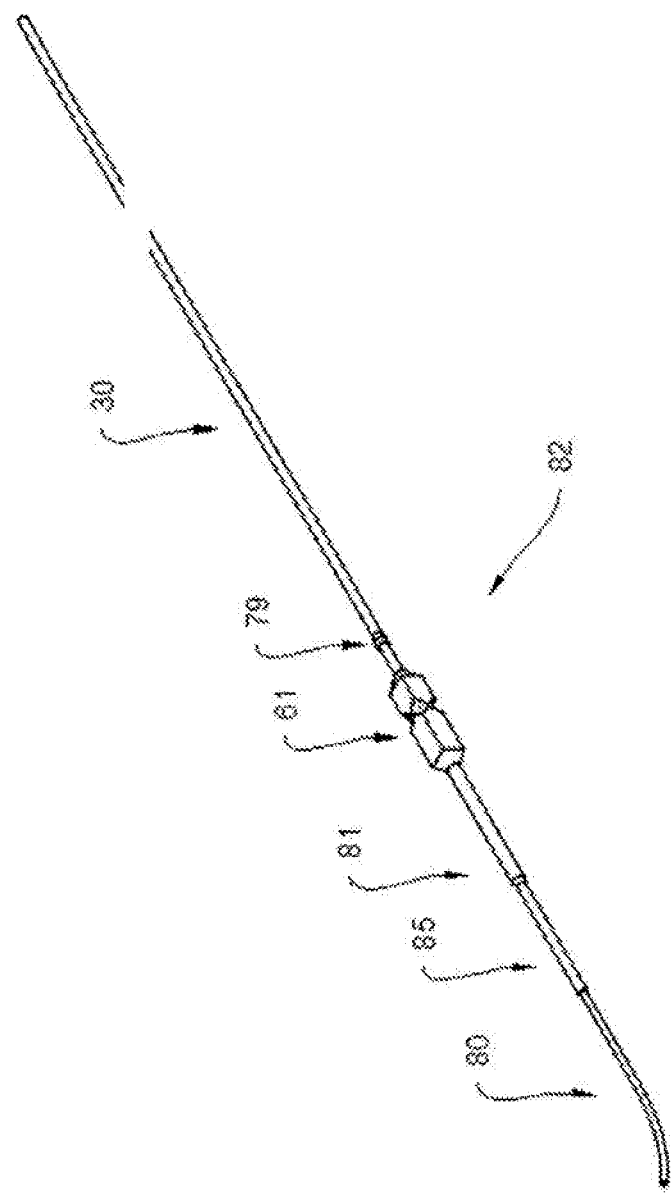

DELIVERY AND EXTRACTION DEVICES

CROSS-REFERENCE TO RELATED APPLICATIONS

This application is a continuation of PCT/US2010/060622, filed 16 Dec. 2010, which claims priority to U.S. Provisional 61/286,788 filed 16 Dec. 2009, which are hereby incorporated by reference in their entirety.

TECHNICAL FIELD

The present invention relates to delivery and extraction devices.

BACKGROUND

Medical implantation procedures generally involve the delivery of a desired substance (e.g. tissue, drug, microchip, etc) to a target site in a subject. One type of tool that has found use in certain procedures is the plunger-barrel type device. The use of a plunger-barrel type device for delivery typically involves the steps of loading a barrel with a desired substance, placing the distal end of the barrel at or near the target site in a subject, and ejecting the substance from the barrel by sliding a plunger through the barrel towards the distal end at the target site. Plunger-barrel type devices have also found use in extraction procedures, where a desired substance is extracted from a target site in a subject, essentially by reversing the steps used for delivery such that the substance is loaded into the barrel from the target site.

Difficulty can arise when the substance intended for extraction or delivery is fragile and/or when the target site is blocked or partially blocked by a delicate environment. Trauma to the surrounding environment or the substance itself can occur during the procedure in the event of off-target placement or unintentional movement of the device or extended duration of device use within the subject. Further tissue insult can ensue from the additional bulk of secondary devices such as cameras or fluid jets sometimes used to aid the procedure.

Thus far, plunger-barrel type devices have fallen short on a number of levels including their precision of device mobility and placement, ability to perform multiple functions, and simplicity of use in applications where the substance itself or the environment surrounding the target is delicate, for example, implantation/extraction procedures for nervous, cardiac, vascular, bone, and joint tissue.

Perhaps one of the more sensitive applications is the delivery or extraction of target substances to or from the eye, for example, implantation of retinal tissue into the subretinal space. Unfortunately, this type of surgery is rendered extremely difficult by both a delicate surrounding environment and a fragile target substance.

The subretinal space is the area between the retinal pigment epithelium (RPE) and the photoreceptors of the retina. The transparent, layered retina processes light images projected by the cornea and lens. The photoreceptor layer in the back of the retina transforms the light into electrical impulses. Other retinal layers transfer these impulses through the optic nerve to the brain which interprets the impulses into what we perceive as sight.

Normally, the photoreceptors are in close contact with the RPE. The RPE has many functions. It provides nutrition for the photoreceptors, and also removes waste products from the photoreceptors. In many diseases, the photoreceptors and retinal pigment epithelium degenerate. Such diseases include retinitis pigmentosa, dry age-related macular degeneration, Stargardt's disease, choroideremia, rod cone dystrophy, and Sjögren's reticular dystrophy. In a normal eye, there are no blood vessels in the subretinal space. However, in some retinal diseases, blood vessels and connective tissue can grow in this space. These abnormalities in the subretinal space under the retina can damage the retina in the back of the eye and can lead to blindness. Under certain disease conditions, the photoreceptors can detach very easily from the RPE. The photoreceptors will then degenerate, resulting in vision loss or blindness, while the other layers of the retina may remain functional. After removing the abnormal blood vessels, vision may be restored by replacing the diseased RPE and/or photoreceptors which may then integrate with the functional part of the retina.

Frequent causes of blindness are dry age-related macular degeneration and retinitis pigmentosa. The macula is located in the back of the eye in the central portion of the retina and is responsible for central vision. In subjects with dry age-related macular degeneration and retinitis pigmentosa, there is initially a dysfunction of the photoreceptors and/or RPE in the macular region. This results in impairment of central and/or peripheral vision. Age related macular degeneration is a disease that has been treated with piston-barrel type devices.

Retinitis pigmentosa is a term for genetically caused photoreceptor degeneration. In these subjects, the photoreceptors must be replaced. Again, such delivery can be accomplished by piston-barrel type devices.

Surgical correction of diseases in the subretinal space between the retina and the RPE is rendered extremely difficult by the environment in which the surgery must take place. Moreover, the surgical procedure disclosed herein to implant retinal tissue into the subretinal space of the eye is complicated by the fact that fetal retinal tissue is in the nature of a transparent gelatinous mass with two non-interdigitated layers, the photoreceptors and RPE, and therefore extremely fragile.

Difficulties of implanting retinal tissue have been previously noted, as discussed in U.S. Pat. No. 5,941,250; U.S. Pat. No. 6,159,218; and U.S. Pat. No. 6,156,042, which describe delivery devices for implanting retinal tissue into the subretinal space of the eye. These devices are of the plunger-barrel type and provide a "mandrel" as the plunger and a mandrel sleeve as the barrel. A tubular nozzle is telescoped over the distal end of the mandrel sleeve and is longitudinally slidable over the mandrel and onto the mandrel sleeve to eject the loaded retinal tissue. In the loaded position, the nozzle is positioned at the far distal end of the sleeve, but biased to slide back over the sleeve by a flat spring toggle having its distal end connected to the nozzle and its proximal end connected to the handpiece. However, none of U.S. Pat. No. 5,941,250; U.S. Pat. No. 6,159,218; and U.S. Pat. No. 6,156,042 teach a device with sensitive, error-reducing delivery control, a device having a nozzle that enables precise control of placement, or a device having a multifunctional mandrel.

U.S. Pat. No. 7,468,065 to Weber et al. describes a device for delivery of ocular implants, but like other devices discussed above, this device fails to meet the needs of applications involving fragile substances to be delivered or extracted, or where the target site is blocked by a delicate environment.

What are needed in the art are high-precision devices that are capable of rapid, non-invasive, delivery and/or extraction, yet simple to use and less prone to user error.

SUMMARY OF THE INVENTION

The present invention relates to mandrel/mandrel-guide type devices for delivering or extracting substances. A device of the present invention comprises a delivery unit comprising a mandrel guide and a mandrel disposed internally to the mandrel guide, wherein the delivery unit is supported by a delivery unit support (e.g. a handpiece), and wherein the delivery unit is operably linked to a delivery controller (e.g. a delivery toggle), whereby engagement and operation of the delivery controller by the user's operating member (e.g. a finger) induces longitudinal movement of the mandrel relative to the mandrel guide. Delivery of a substance from a delivery device is optionally achieved by loading the substance into the mandrel guide, placing the distal end (e.g. nozzle tip) of the mandrel guide at or near the target site in an environment (e.g. subretinal space of the eye) by partially inserting the mandrel guide (e.g. inserting the nozzle portion) into the environment (e.g. an eye) and ejecting the substance from the mandrel guide. This ejection is optionally accomplished, for example, by operating the delivery controller to induce longitudinal movement of the mandrel relative to the mandrel guide such that the mandrel slides through the mandrel guide towards the distal end and forces the substance form the distal end. Conversely, extraction of a substance into an extraction device (or loading a delivery device) is optionally achieved essentially by reversing the steps for delivery discussed above.

The present invention contemplates various embodiments, for example, those described below, which are optionally applied to mandrel/mandrel-guide type devices independently or in combination. For example, the present invention provides improved delivery controllers, mandrels, and mandrel guides which are optionally applied independently or in combination to mandrel/mandrel-guide type devices such as those taught herein.

In one embodiment, the mandrel of the device comprises one or more conductive members for performing one or more secondary activities during delivery or extraction procedures (e.g. aspiration or infusion of a fluid; light projection; viewing through a scope, and/or reducing bleeding by for example, diathermy using electrodes). In one embodiment, the device comprises means for interfacing the mandrel with a secondary device for performing said activities. For example, a Luer lock-type fitting is optionally provided for interfacing with a fluid pump such as a syringe.

In one embodiment, the mandrel guide comprises a removable or disposable nozzle at the distal end, wherein the delivery controller is operably linked to the delivery unit, wherein the operable linkage is configured such that the nozzle is allowed to be fully inserted (e.g. pasta nozzle coupler) into the entry site of the environment (e.g. the eye without causing further trauma). Optionally, the nozzle is non-cylindrical (e.g. shaped for delivering sheets and/or nanoplates) and/or curved when in position for delivery. The nozzle is optionally coupled to a proximal length of guide, for example, by a low profile coupler such as a low profile reversible coupler.

In one embodiment, the mandrel guide of the device comprises a proximal length of guide and a nozzle coupled to the distal end of the proximal length of guide, wherein the nozzle is longitudinally fixed relative to the proximal length of guide and the delivery controller is operably linked to the delivery unit at a location proximal to the nozzle, optionally wherein the delivery controller is operably linked to the delivery unit inside the delivery unit support. Optionally, such a configuration allows for full insertion of the nozzle (e.g. pasta low-profile nozzle coupler). Optionally, the device comprises a nozzle which is non-cylindrical (e.g. shaped for delivering sheets and/or nanoplates) and/or curved (e.g. longitudinally arched), for example, when in position for delivery. Optionally, the nozzle is non-cylindrical (e.g. flattened or oblate) through the entire length (or a substantial portion) of the nozzle is alternatively cylindrical at the proximal end but non-cylindrical at the distal tip (e.g. oblately flared).

In one embodiment, the mandrel guide of the device comprises a removable or disposable nozzle and a proximal length of guide, wherein the proximal end of the nozzle is coupled to the distal end of the proximal length of mandrel guide by a reversible coupler, such as gripping members (e.g. jaws or inner gripping members which are serrated) extending from the proximal length of guide to secure the nozzle, or other reversible coupling means. Such a configuration optionally provides a low profile coupler. Optionally, the device further comprises a sliding jaw lock. Optionally, the device comprises a flexible nozzle which is curved (e.g. longitudinally arched) when in position for delivery. Optionally the nozzle is substantially non-cylindrical (e.g. flattened or oblate). Optionally, the mandrel guide is configured for full insertion of the nozzle when in position for delivery (e.g. using a low-profile coupler and/or a nozzle of appropriate length).

In one embodiment, the device comprises: a delivery unit biasing member (e.g. spring) or a delivery unit biasing means for providing or applying ('applying' or 'imparting') a force to the delivery unit to bias the delivery unit for longitudinal movement (e.g. to deliver a loaded substance), wherein the device further comprises delivery unit engagement means for preventing said longitudinal movement of the delivery unit upon engagement, and wherein the delivery controller is configured to engage and disengage the delivery unit engagement means from said delivery unit. The delivery unit engagement means optionally inhibits said longitudinal movement by applying an opposing force such a frictional force (e.g. using a traction pad) or a normal force (e.g. using a ratchet teeth/ knife edge lock), or a combination of both. In such an embodiment, the delivery controller optionally comprises biasing means to disengage the delivery unit engagement means from the delivery unit, for example, by configuring the delivery controller such that engagement and operation of the delivery controller by the user (e.g. depression of a lever or other toggle linked to the delivery unit engagement means) disengages the delivery unit engagement means, thereby allowing said longitudinal movement, while disengagement of the delivery controller (e.g. releasing pressure from the toggle) engages the delivery unit engagement means with the delivery unit. Optionally, the device further comprises a safety switch (e.g. safety pin configured to freely move longitudinally and move laterally into and out of a safety latch) to oppose the bias of the delivery unit basing means, thereby preventing said longitudinal movement of the delivery unit, regardless of whether or not the delivery unit engagement means is engaged or disengaged with the delivery unit.

In one embodiment, the delivery unit is operably linked to a delivery controller, wherein upon engagement and operation of the delivery controller by a user's operating member, a net longitudinal force is applied or imparted to the mandrel or mandrel guide, thereby moving the mandrel or mandrel guide from a first longitudinal position towards a second longitudinal position at a desired rate; and wherein, at one or more intermediate positions between said first and second positions, the mandrel or guide immediately discontinues longitudinal movement (e.g. within about 1 mm of longitudinal movement) upon the user's operating member disengaging or releasing pressure from the delivery controller. Optionally, the user's operating member is a finger or finger tip. Optionally, the device further comprises a conductive mandrel, as taught herein. Optionally, the device further comprises a non-cylindrical (e.g. oblate or flattened) nozzle and/ or a nozzle that is curved (e.g. longitudinally arched) when in position for delivery. Such a configuration is optionally obtained in a number of manners, for example, by providing a slidable delivery controller coupled to the delivery unit, or providing both a delivery unit biasing means (e.g. spring) and a delivery unit engagement means (e.g. traction pad or knife edge lock).

In one embodiment, the mandrel guide is a modular mandrel guide comprising a proximal length of guide comprised of two reversibly coupled members: a modular mandrel guide base and a nozzle holder, wherein the nozzle holder is coupled to or configured to be coupled to a nozzle, for example, by a reversible nozzle coupler. Optionally such a device is provided with a plurality of nozzle holders, each configured for a respective mandrel.

BRIEF DESCRIPTION OF THE DRAWINGS

FIG. 5 depicts a conductive mandrel of the present invention.

DETAILED DESCRIPTION OF THE INVENTION

As used here, the following definitions and abbreviations apply.

"Examplary" (or "e.g." or "by example" or "[numbered component of a figure]") means a non-limiting example. References to specific examples are merely for illustrative purposes only and are not intended to limit the invention to species of components or orientations depicted in the figures.

"High precision" or "High precision device" refers to one or more features of the present invention, namely precise placement of the nozzle tip at the target site; precise longitudinal movement of the mandrel relative to the mandrel guide, precise movement and/or placement of a target substance, precise loading of a target substance, or precise manipulation of the device (e.g. rotation). Similarly, use of the word "precise" optionally refers to precision with respect to one or more of the above mentioned features.

"Operably linked", with respect to a delivery controller or component thereof, means that a delivery controller (e.g. toggle) is linked to at least one component of the delivery unit (e.g. mandrel or mandrel guide) such that activation or operation of the delivery controller causes the mandrel to move longitudinally, relative to the mandrel guide, for example, to cause the mandrel to forcibly eject a substance loaded in the mandrel guide. With respect to a conductive mandrel and secondary device, "operably linked" means conductively linked.

The present invention provides devices for delivering or extracting a substance. Although the device is not limited to any particular configuration, the following exemplary embodiments are provided to illustrate the principle functional components of a device according the present invention.

Figure 1:
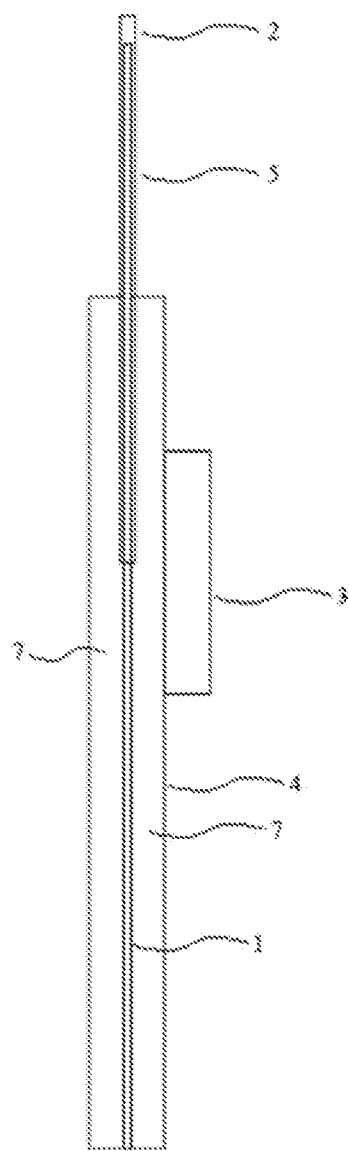
FIG. 1 depicts a schematic representative of a device of the present invention, showing only the relative longitudinal orientation of the mandrel, mandrel guide, and the distal end of the delivery unit support.

One embodiment provides a device (e.g. hand-held device) for delivering a substance, as depicted in FIG. 1. The device comprises a delivery unit (e.g. 5) comprising a mandrel guide (e.g. 2) (e.g. a cannula or barrel) and a mandrel (e.g. 1) (e.g. a plunger) disposed about (e.g. internally to) the mandrel guide (e.g. 2). The delivery unit is supported by a delivery unit support (e.g. 4) (e.g. the device housing or handpiece). A delivery controller (e.g. 3) (e.g. toggle switch such as a lever) is operably linked (linkage not shown) to the delivery unit (e.g. 5) through either the mandrel (e.g. 1) or mandrel guide (e.g. 2) to control longitudinal movement of the mandrel (e.g. 1) relative to the mandrel guide (e.g. 2). The device is optionally used for implanting a desired substance by loading the substance into the mandrel guide (e.g. 2) (e.g. the nozzle), inserting the mandrel guide (e.g. 2) into an environment (e.g. a subjects body) to place the distal end of the mandrel guide (e.g. 2) (e.g. nozzle) at the target delivery site, and operating the delivery controller (e.g. 3) (e.g. by toggling using a finger) to induce longitudinal movement of the mandrel (e.g. 1) through the mandrel guide (e.g. 2) towards the distal end until the substance is ejected from the mandrel guide (e.g. 2).

Delivery Unit

Devices of the present invention comprise a delivery unit (e.g. 5) for delivery (e.g. implantation) and/or extraction (e.g. loading) of a substance. The delivery unit (e.g. 5) comprises a mandrel guide (e.g. 2) and a mandrel (e.g. 1) disposed about (e.g. disposed internally to) the mandrel guide (e.g. 2), wherein the mandrel (e.g. 1) and mandrel guide (e.g. 2) move longitudinally, relative to each other. The delivery unit (e.g. 5) is supported by the delivery unit support (e.g. 4) (e.g. a handpiece). At least one of the components 1 or 2 of the delivery unit (e.g. 5) is not longitudinally fixed to the delivery unit support (e.g. 4) to allow longitudinal movement of the mandrel (e.g. 1) relative to the mandrel guide (e.g. 2). The relative longitudinal movement of the mandrel (e.g. 1) and the mandrel guide (e.g. 2) is controlled by a delivery controller (e.g. 3) (e.g. a toggle switch), which is operably linked to the delivery unit (e.g. 5) (e.g. by providing a linkage between the unfixed component and the delivery controller (e.g. 3)).

One embodiment provides a delivery unit (e.g. 5) comprising a mandrel guide (e.g. 2), wherein the mandrel guide has an open distal end 300 for discharge of a substance if loaded in the mandrel guide (e.g. 2); and a longitudinally elongated mandrel (e.g. 1) disposed internally to the mandrel guide (e.g. 2), whereby relative longitudinal movement of the mandrel through the mandrel guide towards the open distal end 300 biases the loaded substance to move longitudinally towards the open distal end 300. The device further comprises a delivery unit support (e.g. 4) (e.g. handpiece) providing support to the delivery unit (e.g. 5), wherein at least one of the mandrel (e.g. 1) and the mandrel guide (e.g. 2) is not fixed to the delivery unit support (e.g. 4) to allow longitudinal movement there about. The mandrel (e.g. 1) or mandrel guide (e.g. 2) further comprises means for operably linking the delivery unit (e.g. 5) to a delivery controller (e.g. 3). For example, the mandrel or mandrel guide optionally comprises a means for engaging a delivery unit-engaging means, such as any of: a) teeth of a ratchet (e.g. 6) for engaging and disengaging a knife edge lock (e.g. 15); b) a threaded hole (e.g. 29), for receiving a screw securing the delivery controller there to; or c) a member or material (e.g. the surface of mandrel (e.g. 1) or mandrel guide (e.g. 2)) which provides traction when engaged with a traction pad or clamp of the delivery controller.

Optionally, the device further comprises a delivery unit-biasing member, such as a spring (e.g. tension spring or coaxial spring such as part 17 of FIG. 8) or other delivery-unit biasing means, imparting a force on the delivery unit to bias the delivery unit for the relative longitudinal movement. Although any spring is optionally used, surprisingly, tension springs are optionally used to provide greater precision during loading, and greater control of movement during delivery, and/or more predictable movement, for example, to reduce damage to the loaded tissue (e.g. retinal tissue such as retinal sheets or nanoplates) and/or tissue at the target site (e.g. ocular tissue such as subretinal space). This is especially true over short distances of movement (e.g. during contraction of the spring towards resting state), for example, as seen in delivery of tissue to the eye (e.g. delivery of retinal tissue). Optionally, the delivery unit support comprises a handpiece. Optionally the delivery controller (e.g. 14 or 11) is configured to interface a user's finger (e.g. by placing the delivery controller on the distal end of a handpiece). Optionally, the force required to operate the delivery controller is less than about 3 lbs (e.g. less than about any of: 2 lbs, 1 lb, or ¾ lb; or about any of: 0.25 lb to 2 lb, 0.25 lb to 1 lb, or 0.25 lb to 0.75 lb; or about 200 g to about 500 g; or about 300 g). Optionally, the device is configured for positive action or negative action, as described herein.

Figure 8A:
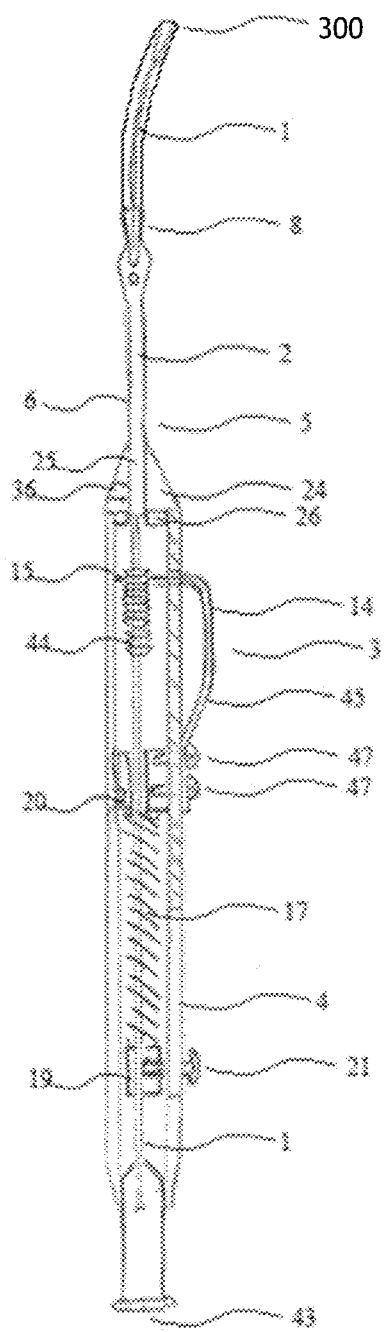
FIG. 8 depicts a device of the present invention with positive action and push-button delivery controller.
Figure 8B:
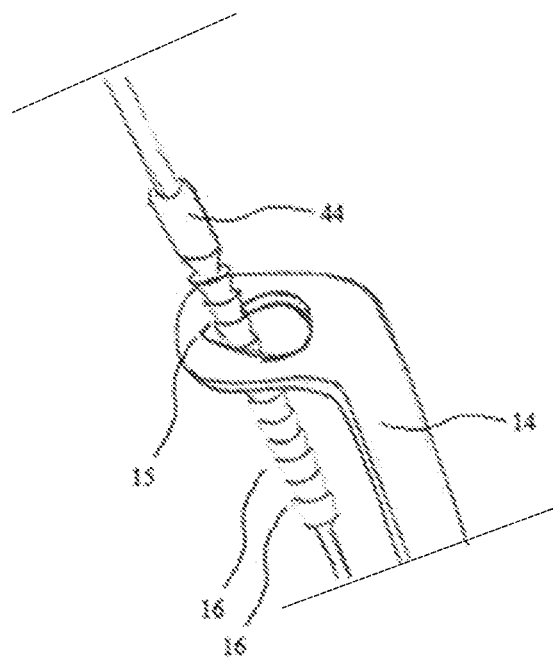
Figure 8C:
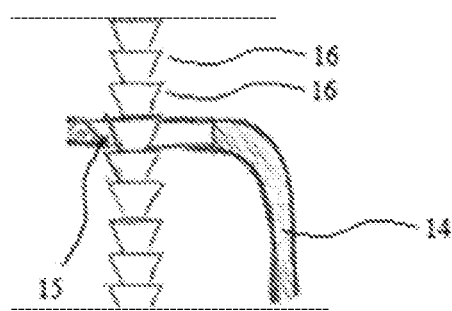
Figure 9A:
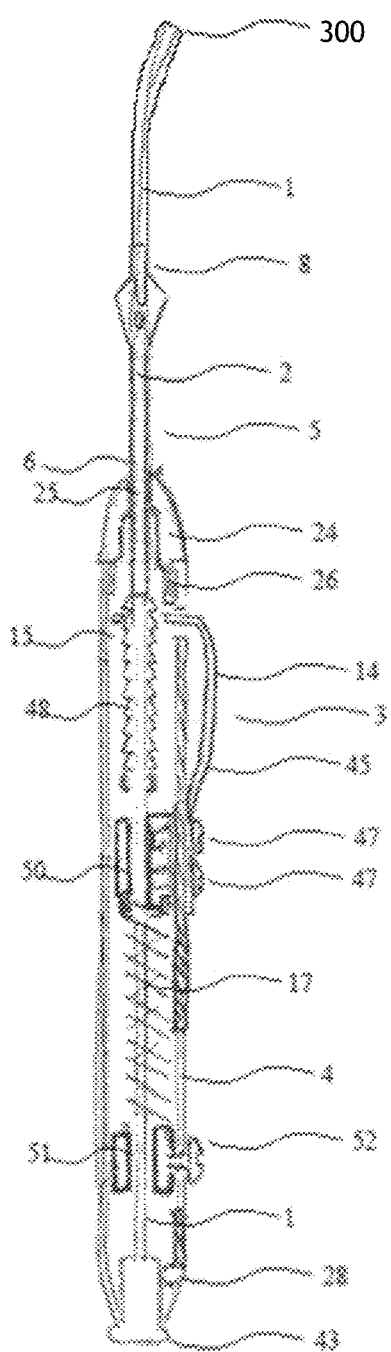
FIG. 9 depicts a device of the present invention with passive action and push-button delivery controller.
Figure 9B:
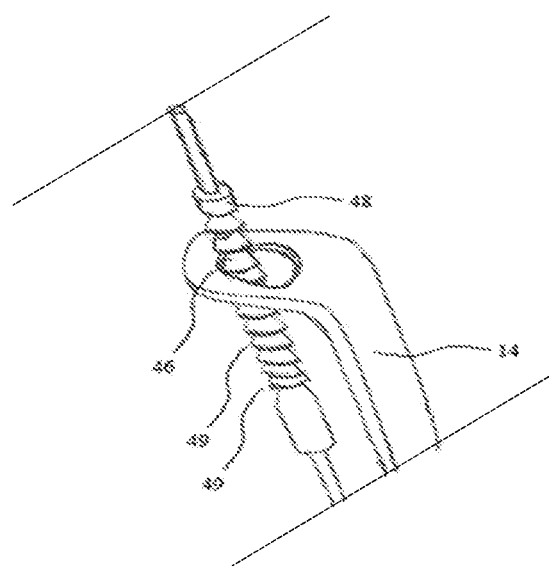
Figure 9C:
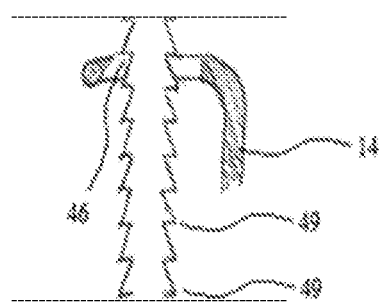
Figure 9D:
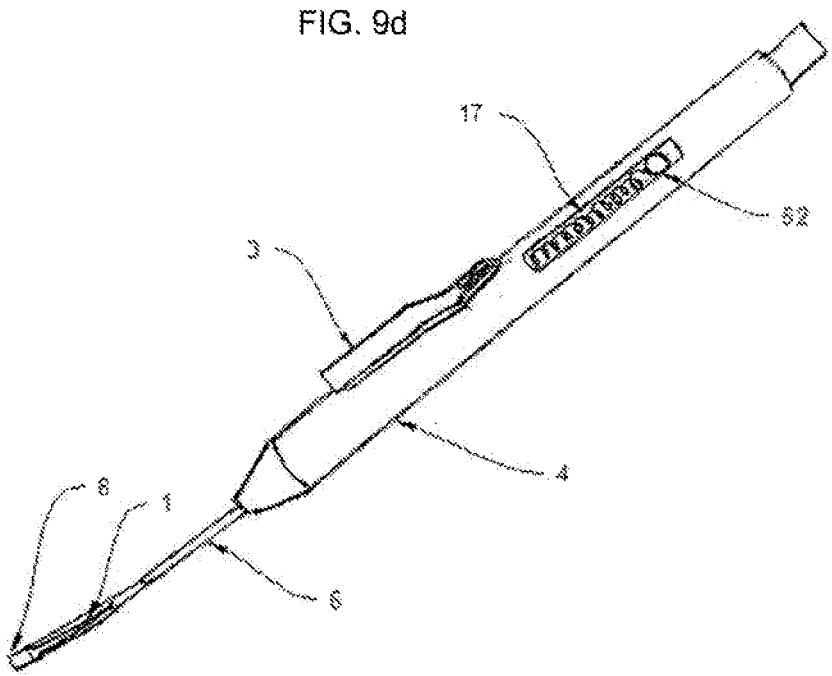

In one embodiment, the device comprises a delivery unit-biasing member as described above, or other delivery-unit biasing means, and the device further comprises force-adjusting means (e.g. a spring bushing with an adjustable position such as part 19 of FIG. 8) to adjust the force of the delivery unit on the delivery unit, wherein adjusting the force changes the delivery speed.

In one embodiment, the delivery unit biasing member or delivery unit biasing means comprises any member or collection of members which cause the mandrel and mandrel guide to move longitudinally relative to each other.

In one embodiment, the delivery unit biasing member or delivery unit biasing means is a spring based, motor-based, magnet-based (e.g. repulsion based), electromagnet-based, hydraulic-based, or pneumatic-based delivery unit biasing means. Optionally, the delivery unit biasing member is a non-electric member (e.g. is a spring). Optionally, the delivery unit biasing member does not comprise a motor. Optionally, the delivery unit biasing member does not comprise an electric motor. Optionally, the delivery unit biasing member is non-hydraulic. Optionally, the delivery unit biasing member is non-fluid pressure based.

Although certain specific examples taught herein provide a spring as a delivery unit biasing member, the present invention is not limited to such spring-based delivery unit biasing members. Accordingly, for any embodiment which is taught herein as including a spring as a delivery unit biasing member, the invention also contemplates an alternative embodiment in which the delivery unit biasing member is any delivery unit biasing member or delivery unit biasing means. For example, as an alternative to a spring, the delivery unit biasing member can comprise a motor-based, magnet-based (e.g. repulsion based), electromagnet-based, hydraulic-based, or pneumatic-based delivery unit biasing means.

In one embodiment, a substance loaded in the mandrel guide moves longitudinally as a result of force applied directly from the mandrel (e.g. 1), i.e. there is a direct interface of the substance with the distal end of the mandrel (e.g. 1). Alternatively or additionally, the substance moves longitudinally as a result of an indirect force applied from the mandrel, e.g. by fluid pressure (e.g. for delivery) or vacuum (e.g. for extraction) created in the mandrel guide (e.g. 2) by longitudinal movement of the mandrel. Alternatively or additionally, the substance moves longitudinally by infusion or suction force induced through ports optionally present on the mandrel (i.e. on a conductive mandrel).

Mandrel

The mandrel (e.g. 1) comprises an elongated member that moves longitudinally about (e.g. slides through) the mandrel guide (e.g. 2) and interfaces the substance intended for delivery at the distal end (e.g. 9) of the mandrel (e.g. 1).

In one embodiment, the mandrel (e.g. 1) comprises an elongated conductive member. Additionally or alternatively, the mandrel comprises an elongated solid member. Optionally, the mandrel comprises an elongated flat member. Optionally, the mandrel comprises an elongated cylindrical member.

In one embodiment, the mandrel (e.g. 1) comprises an elongated steel member.

In one embodiment, the mandrel comprises an elongated rubber or plastic member.

In one embodiment, the mandrel is made of stainless steel tubes and electrically conductive members or optical fibers.

In one embodiment, the mandrel is autoclavable. Optionally, the mandrel comprises optical fibers or other conductive member and is autoclavable without the optical fibers or other conductive member.

In one embodiment, the mandrel (e.g. 1) is flexible.

In one embodiment, the mandrel (e.g. 1) is not flexible. In one embodiment, the mandrel is malleable.

In one embodiment, the mandrel comprises both flexible and rigid portions. Optionally, at least the distal portion of the mandrel is curved (or curvable), optionally wherein the mandrel is curved to slide under the retina into the subretinal space when the device is inserted through the pars plane of the eye. Optionally, at least the distal portion of the mandrel is flexible (e.g. further comprising a rigid nozzle), optionally wherein the mandrel is flexible enough to slide under the retina into the subretinal space when the device is inserted through the pars plane of the eye.

In one embodiment, the distal end of mandrel is configured or shaped to deliver a particular substance (e.g. match fitted to a nozzle shaped there for). Optionally, the substance is retinal cells or tissue (sometimes simply referred to as retinal tissue). Optionally, the substance is a nanoplate or other sheet (e.g. comprising retinal tissue). For example, the mandrel described in FIG. 5, or FIG. 18 or any example selected from Example 3-Example 5, Example 7-Example 10, Example 14, Example 18, Example 4 is optionally configured for delivery of a sheet and/or nanoplate. Optionally, the substance is a nanoplate comprising retinal tissue or stem cells. Optionally, the substance is a nanoplate and the nozzle and distal end of the mandrel are size- and shape-matched to the type of nanoplate.

In one embodiment, the distal end of the mandrel is match fitted to the nozzle (e.g. a nozzle for delivering sheets or nanoplates) such that longitudinal movement therein is smooth without binding yet providing a leak-free tip and/or suction induced by withdrawing the mandrel relative to the nozzle. Optionally, the distal end of the mandrel is match fitted by use of a surface-area increasing member, as taught herein (e.g. for a non-cylindrical nozzle). Such a mandrel optionally further comprises one or more conductive members, as taught herein.

In one embodiment, the mandrel comprises a conductive member (e.g. a tubular member) for conducting a fluid such as a gas or liquid, or other material such as fiber optic fibers. Optionally, a tubular conductive is constructed from a stainless steel or plastic tube (e.g. autoclavable).

In one embodiment, the mandrel comprises a conductive mandrel for conducting light, electricity, sonic waves, and/or other waveforms. Optionally, the tubular conductive member comprises a means for conducting a waveform, such as a fiber optic cable, wire, or tube (e.g. polyimide tube) with wire inserts. Optionally, the mandrel comprises a plurality of electrodes, for example, for performing diathermy (e.g. to stop bleeding).

In one embodiment, the mandrel comprises a conductive mandrel conductively linked to an external device to, for example, drive aspiration, infusion, suction, air jetting, wave transmission, and the like. For example, the mandrels detailed in any of (e.g. as detailed in Example 3, Example 4). In one embodiment, a conductive mandrel is conductively linked to an external device, such as a fluid pump or wave transmitter by an interface, for example, at the proximal end of the mandrel. Optionally, the conductive mandrel comprises one or more distal ports, wherein the conductive mandrel is capable of conducting a fluid or wave between the fluid pump or wave transmitter and the environment at the one or more distal ports.

In one embodiment, the mandrel comprises a tubular conductive member for conducting a fluid and the mandrel optionally comprises an interface for conductively linking the mandrel to a secondary device such as a fluid pump. Optionally, the interface comprises one of a Luer lock type fitting (sometimes referred to as a Luer housing), a tube coupler, and the like. Optionally, the tubular mandrel is optionally conductively linked to an external device to drive aspiration, dispensation, suction, air jetting, liquid infusion, drug infusion, wave transmission, and the like. Although certain specific examples taught herein provide a Luer type fitting as an interface (e.g. to interface a fluid pump), the present invention is not limited to devices comprising such Luer type fittings. Accordingly, for any embodiment which is taught herein as including a Luer fitting, the invention also contemplates an alternative embodiment in which the interface is any interface configured to conductively link a tubular mandrel to a fluid pump. For example, as an alternative to a Luer fitting, the interface can comprise a threaded coupler, tapered nozzle, or any other interface for linking a tube to a fluid pump. For example, in some embodiments, a useful fluid pump interface is a port on the tubular mandrel to which second tube can be connected. Further, when reference is made to a "male" or "female" Leur fitting, the invention also contemplates an alternative embodiment, wherein the interface is any fluid-pump interface, for example, any type of Luer fitting or tube coupler.

Surprisingly, a conductive mandrel (e.g. fluid conductive mandrel) can optionally be configured to allow easier and more precise loading and/or discharge of a substance (e.g. retinal tissue such as in the form of a sheet or nanoplate).

Surprising, a light- or fiber optic-conducting mandrel can optionally be configured to provide more targeted and/or precise lighting or viewing of the target site and/or substance delivered or loaded than the light- or fiber optic conducting secondary devices used in the prior art, for example, because the port(s) are more directly aligned with and/or proximal to the substance and/or target site.

In one embodiment, a conductive mandrel is conductively linked to an external device, such as a fluid pump or wave transmitter by an interface, for example, at the proximal end of the mandrel, wherein the conductive mandrel further comprises one or more distal ports, wherein the conductive mandrel is capable of conducting a fluid or wave between the fluid pump or wave transmitter and the environment at the one or more distal ports. Optionally the conductive mandrel comprises tubular conductive member. Optionally the conductive mandrel comprises tubular conductive member and the fluid pump is gas or liquid pump. Optionally the distal end of the conductive mandrel comprises a surface area increasing member (e.g. filler weld) that increases the lateral surface area of the conductive mandrel (e.g. when match fitted to, for example, a non-cylindrical nozzle). Optionally, the distal end of the conductive mandrel comprises a plurality of conductive members disposed laterally of each other and the surface area increasing member is disposed between or among the plurality of conductive members (e.g. when match fitted to a non-cylindrical nozzle). Such configurations are useful, for example, where the conductive members conduct a liquid, such as for infusion and/or aspiration, gas, such as for aeration and/or jetting, light, or electricity, such as for diathermy, and combinations thereof (e.g. where outer conductive members conduct a fluid and inner conductive members conduct light and/or cauterizing waves).

Figure 3A:
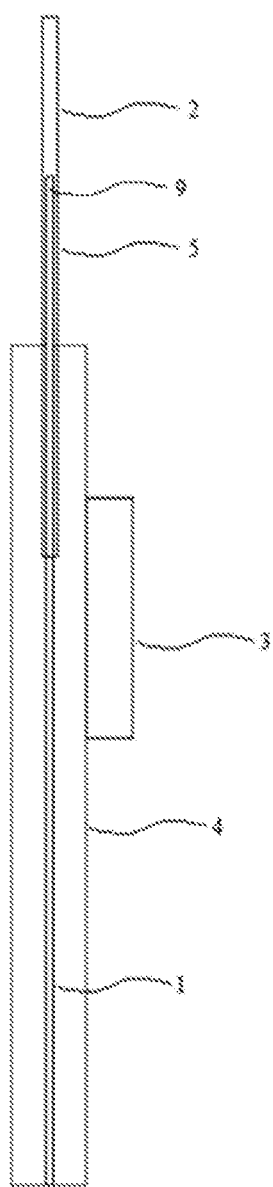
FIG. 3 depicts a schematic representative of a device of the present invention, having a conductive mandrel of the present invention, showing only the conductive functionality of a conductive mandrel.
Figure 3B:
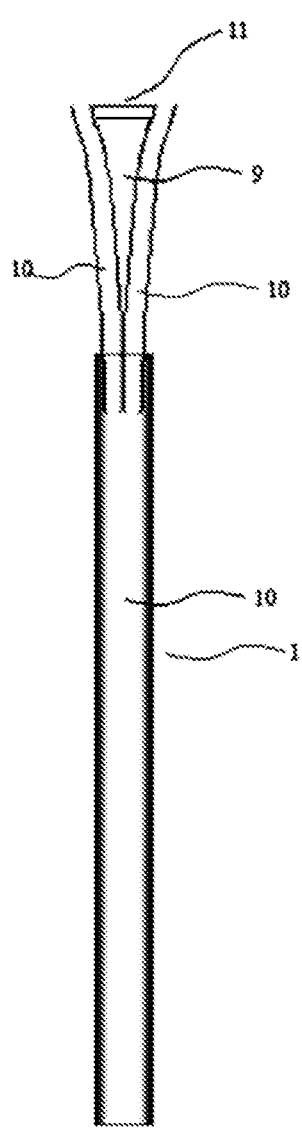

In one embodiment, the mandrel (e.g. 1) comprises a plurality of tubular conductive members that are laterally joined at the distal end by one or more joining members, such as a filler weld (e.g. 11), for example, as shown in FIG. 3b (e.g. when match fitted to, for example, a non-cylindrical nozzle). Other means to connect distal ends of tubular conductive members include adhesives and/or molded plastic. Optionally, the mandrel (e.g. 1) interfaces the substance to be delivered or extracted directly at a joining member. Optionally, the mandrel (e.g. 1) interfaces the substance to be delivered or extracted directly at a joining member or indirectly by a pressure or vacuum zone in the mandrel guide created by longitudinal movement of the mandrel.

When multiple conductive members are provided that conduct the same fluid or wave, the members are optionally connected to a secondary device (e.g. wave transmitter or fluid pump) in any manner which allows the members to conduct the same wave of fluid. Optionally, the mandrel (e.g. 1) comprises a plurality of serially linked tubular conductive members. Optionally, the mandrel (e.g. 1) comprises a plurality of conductively linked conductive members. Optionally, the mandrel (e.g. 1) comprises a plurality of tubular conductive members 10, wherein a plurality of tubular conductive members are linked in series and a plurality of tubular conductive members are linked in parallel, for example, as shown in FIG. 3b. In one embodiment, a plurality of tubular conductive members each provide different conductivity, for example, to conduct different materials such as gas and fiber optics, fiber optics for light or camera, and electrodes for diathermy, or to differentially conduct a material such as the aspiration and dispensation of a given fluid.

In one embodiment, the mandrel (e.g. 1) comprises a plurality of tubular conductive members are each conductively linked to a different external device or conductive means. In one embodiment, a plurality of tubular conductive members provide the same conductivity or conduct the same material. In such a configuration, each tubular conductive member is optionally conductively linked to a different external device or conducting means or each is optionally linked to the same external device or conducting means.

Optionally, the mandrel (e.g. 1) comprises a plurality of tubular conductive members at the distal end of the mandrel and a reduced number of proximal tubular conductive members, such as a single proximal tubular conductive member, wherein the plurality of distal tubular conductive members are conductively linked to the reduced number of tubular conductive members. Optionally, the mandrel (e.g. 1) comprises two tubular conductive members at the distal end of the mandrel (e.g. 1) conductively linked to a distal single tubular conductive member, wherein the single tubular conductive member is conductively linked to an external device or conductive means, for example, as shown in FIG. 3b.

The mandrel (e.g. 1) is optionally constructed from any material that induces longitudinal movement of the substance intended for delivery or extraction in the same direction as the mandrel (e.g. 1) (or force induced thereby; e.g. infusion or suction) when the mandrel (e.g. 1) moves (or when a force is applied) longitudinally relative to the mandrel guide (e.g. 2).

Mandrel Guide

The mandrel guide (e.g. 2) is disposed about (e.g. telescoped over) the mandrel (e.g. 1) and comprises at least two functional sections: a proximal length of guide (e.g. 6) and a distal nozzle 8, for example, as shown in FIG., 2 or FIG. 8. Optionally, the proximal length of guide is coupled to at least one of the delivery unit support (e.g. 4) (e.g. for support) and the delivery controller (e.g. for control of longitudinal movement). During delivery or extraction of a substance, at least a portion of the nozzle (e.g. 8 or 86) is inserted into the subject's body or otherwise nears contact with the target delivery site in or on the subject. Optionally, the nozzle is fully inserted into the environment (e.g. an eye) when in position for delivery (e.g. with nozzle tip at, near, or in the subretinal space).

The mandrel guide (e.g. 2) is optionally provided in any shape or configuration, so long as a loaded substance is guided towards and out of the distal nozzle from operation of the delivery controller (e.g. 3). For example, the mandrel guide (e.g. 2) is optionally provided as a cannula, barrel, sleeve, tubular member, or track, wherein the mandrel (e.g. 1) moves longitudinally about (e.g. through) the mandrel guide 1. The nozzle (e.g. 8) of the mandrel guide is optionally shaped for delivering a particular substance (e.g. non-cylindrical or oblate for delivering sheet-like substances), for example, and a proximal length of guide is minimally sized to house the mandrel or proximal portion thereof.

In one embodiment, the mandrel guide (e.g. 2) comprises two or more members (e.g. a proximal length of guide and a distal nozzle) coupled together to form a functional mandrel guide (e.g. as set forth in FIG. 6). Alternatively, the mandrel guide is formed as a single member, for example, where the proximal length of guide and the distal nozzle are formed together from a mold. The proximal length of guide and the distal nozzle optionally have different lateral cross sections or optionally have the same or similar lateral cross sections.

In one embodiment, the mandrel guide (e.g. 2) comprises an aperture in a sidewall of the mandrel guide for the acceptance of a substance, for example, tissue (e.g. retinal tissue). Examples of such a mandrel guide are described in U.S. Pat. No. 6,156,042 which is hereby incorporated by reference.

In one embodiment, the fit between the nozzle and the distal end of mandrel permits relative movement, but induces suction in the tip portion of the nozzle when the nozzle is advanced over the mandrel to thereby induct a substance (e.g. rectangular piece of retinal tissue). Optionally, the distal end of the nozzle is match fitted to slide over the distal end of the mandrel such that longitudinal movement is smooth without binding yet providing a leak-free tip. Optionally, relatively hard implants are inserted manually into the tip of the nozzle.

In one embodiment, the mandrel guide is flexible. In one embodiment, the mandrel guide is rigid. In one embodiment, the mandrel guide comprises a flexible region and a rigid region. Optionally, the nozzle is flexible (e.g. made of fluorinated ethylene propylene or elastic plastic with an appropriate thickness to retain flexibility) and proximal length of guide is rigid (e.g. made of steel). Optionally, the nozzle is flexible, optionally wherein the nozzle is flexible enough to slide under the retina into the subretinal space when the device is inserted through the pars plana of the eye. Alternatively, the nozzle is rigid but curved (e.g. longitudinally arched) to slide under the retina into the subretinal space when the device is inserted through the pars plana of the eye.

In one embodiment, the nozzle is transparent.

In one embodiment, the nozzle is molded of elastic plastic, for example fluorinated ethylene propylene with an appropriate thickness, so as to have a curvature at the tip thereof in order to slide under the retina into the subretinal space. Surprisingly, fluorinated ethylene propylene optionally provides a superior nozzle compared to nozzles constructed with other elastic plastics. For example, nozzles constructed from fluorinated ethylene propylene can not only optionally be constructed as a transparent or translucent member, thereby allowing visualization of the loaded substance or position thereof about the nozzle, but are optionally reusable and/or autoclavable, or are optionally disposable because they are cheap and/or easy to construct. Because of its elasticity, the curved nozzle tip may, when retracted, straighten out over the mandrel so as to deposit implant tissue at the target area behind the retina. Optionally, the tip of the nozzle has smooth edges and, to facilitate uptake of the retinal tissue, is optionally provided with a small lip to aid in induction of the retinal tissue, for example, as described in U.S. Pat. No. 6,156,042 which is hereby incorporated by reference.

In one embodiment, the nozzle is configured or shaped to deliver a particular substance. Optionally, the substance is retinal tissue. Optionally, the substance is a sheet, for example, a sheet of RPE or nanoplate. Optionally, the substance is a nanoplate comprising retinal tissue or stem cells. Optionally, the substance is a nanoplate and the nozzle is sized and shaped to fit match the nanoplate. Optionally, the nozzle has rectangular lateral cross section, for example, a rectangle with curved edges. Optionally, the nozzle has lateral cross section at the distal end which comprises a rectangle and a lateral cross section at the proximal end which comprises a circle, for example, for coupling to a cylindrical proximal length of guide (e.g. by a nozzle lock).

In one embodiment, the nozzle is made from a biocompatible polymer.

In one embodiment, the nozzle is made from a biocompatible polymer with a wall thickness of less than about 0.2 in, for example, less than about any of: 0.1 in, 0.05 in, or 0.1 in such as approximately 0.005 to 0.006 in.

In one embodiment, the nozzle is made from a biocompatible polymer with a wall thickness of less than about 0.2 in, for example, less than about any of: 0.1 in, 0.05 in, or 0.1 in such as approximately 0.005 to 0.006 in, and features a thin wall section to minimize trauma and a tapered tip to facilitate entry into the subretinal space.

Optionally, the mandrel guide is configured to be prone to induce tissue trauma. Surprisingly, such mandrel guides are less prone to induce tissue trauma than those described by the prior art, especially, for example, when delivering non-cylindrical substances, such as sheets (e.g. sheets or nanoplates of retinal cells) and/or when using curved nozzles, which optionally also provide for a high precision device. For example, one embodiment of a mandrel guide of the present invention provides a distal nozzle having a flexible, non-cylindrical length at the distal end (e.g. for delivering sheets or nanoplates) and proximal length of guide comprising a cylindrical length (or length with a circular cross section) proximal thereto, wherein the nozzle is configured to be insertable into the patient past the non-cylindrical length such that the length of guide having a circular cross section protrudes from the insertion site (e.g. surface of the eye). Optionally, the cylindrical length (or length with a circular cross section) that protrudes from the eye is not flexible. Surprisingly, such a configuration is far superior to prior art devices, for example, the nozzle on the device described in U.S. Pat. No. 6,159,218, which has a rectangular cross section for delivering RPE sheets, protrudes from the eye when in position for delivery. The movement (e.g. rotation) of such a rectangular cross section while inserted through tissue (e.g. an eye) can be very dangerous as leakage or even deflation can occur. For applications which use a non-circular nozzle or guide, a guide having a circular cross section at the portion which extends through the insertion point (e.g. surface of the eye) would be provide a safer proceeded which, for example, is less likely to cause leakage or deflation. Although the proximal portion of the nozzle described in U.S. Pat. No. 6,159,218 is cylindrical (see component 110 of FIG. 7 of U.S. Pat. No. 6,159,218) its larger diameter precludes insertion up to this cylindrical section—note that the proximal portion of the prior art nozzle is sized to fit over the distal portion of a guide component (see component 108 of FIG. 7 of U.S. Pat. No. 6,159,218), which is in-turn sized to slide over the guide support (see component 104 of FIG. 7 of U.S. Pat. No. 6,159,218). The prior art three-layer design prohibits the construction of a smaller diameter for the proximal, cylindrical portion of the nozzle. However, certain mandrel guides of the present invention enable a two-layer design, as will be readily appreciable to a skilled artisan with the teachings provided herein, where the proximal end of the nozzle is placed relatively flush with the distal end of the proximal length of guide and where the nozzle and proximal length of guide a coupled by a nozzle lock. With the teachings provided herein, the skilled artisan can now provide various low-profile configurations (e.g. using a nozzle coupler) to allow insertion into a patient without substantial trauma.

In one embodiment, the delivery device comprises a mandrel guide comprising a nozzle and a proximal length of guide, wherein the proximal length of guide and the proximal end of the nozzle have about the same diameter or other cross section length (e.g. where a nozzle lock is configured for placement over both components). Optionally, the distal end of the proximal length of guide and the proximal end of the nozzle are cylinders or have circular or circle-like cross sections. Optionally, a nozzle lock is provided which has an inner or luminal diameter substantially the same width as the outer surface of the distal end of the proximal length of guide and the proximal end of the nozzle.

In one embodiment, the delivery device comprises a disposable or removable nozzle. Such a device is optionally used with nozzles of different shapes and/or sizes in order to use the same device for different applications.

In one embodiment, the device comprises a delivery unit comprising a mandrel guide, wherein the mandrel guide has an open distal end for discharge of a substance if loaded in the mandrel guide; and a longitudinally elongated mandrel disposed internally to the mandrel guide, whereby relative longitudinal movement of the mandrel through the mandrel guide towards the open distal end biases the loaded substance to move longitudinally towards the open end. In one embodiment, the mandrel guide comprises a proximal length of guide and a distal nozzle removably fixed to the proximal length of guide (e.g. as set forth in FIG. 6).

Optionally, the distal nozzle is removably fixed to the proximal length of guide by a coupler (e.g. a low profile coupler for allowing insertion without trauma), wherein the coupler comprises interacting members, wherein the first member of the pair is fixed to the nozzle and the second member of the pair is fixed to the proximal length of guide. Optionally, the first member of the pair is permanently fixed to the nozzle and/or the second member of the pair is fixed to the proximal length of guide. Optionally, the first member is made of the same material as the nozzle or at least the proximal portion thereof (e.g. formed together from a mould).

Optionally, the second member is made of the same material as the proximal length of guide or at least the distal portion thereof (e.g. formed together from a mould). Optionally, the proximal length of guide is made of steel. Optionally the second member of the pair comprises one or more jaws, opposing members, or gripping members extending from the distal end of the proximal length of tube, optionally wherein the second member comprises a pair of opposing jaws. Optionally, the one or more jaws comprise one or more gripping members for securing the nozzle. Optionally, the one or more gripping members comprise one or more teeth. Optionally, the one or more jaws, opposing members, or gripping members are secured onto the nozzle by a lock (e.g. a sliding nozzle lock or threaded nozzle lock), for example, a nozzle lock with a cylindrical lumen (threaded or unthreaded), which biases or forces the members into securing position (e.g.

together upon being placed thereon). Optionally the nozzle is formed from a flexible material.

Optionally, the first member comprises one or more tooth holes for receiving one or more teeth, and the second member comprises one or more teeth for securing the nozzle by the one or more tooth holes. Optionally, the proximal length of guide comprises a removable jaw lock (e.g. sliding lock or threaded nozzle lock) for locking the jaws in a nozzle-securing position, optionally wherein the jaws are biased in a nozzle-non-securing position. Optionally, the jaw lock is a sliding jaw lock, whereby sliding the sliding jaw lock onto the jaws closes the jaws extending onto the nozzle to secure the nozzle to the proximal length of guide. Optionally, the second member of the pair comprises a sliding jaw lock engaging member, wherein the engaging member is biased to engage and immobilize the sliding jaw lock, and wherein the engaging member is positioned to engage the sliding jaw lock when the sliding jaw lock is in position for securing the jaws to the nozzle.

Figure 6A:
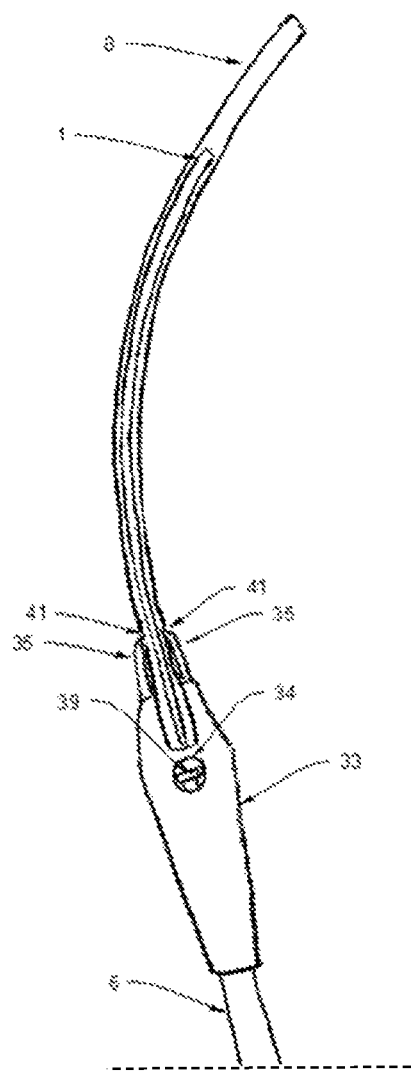
FIG. 6 depicts a mandrel guide of the present invention having a quick-connect mechanism as a reversible nozzle coupler.
Figures 6B, 6C:
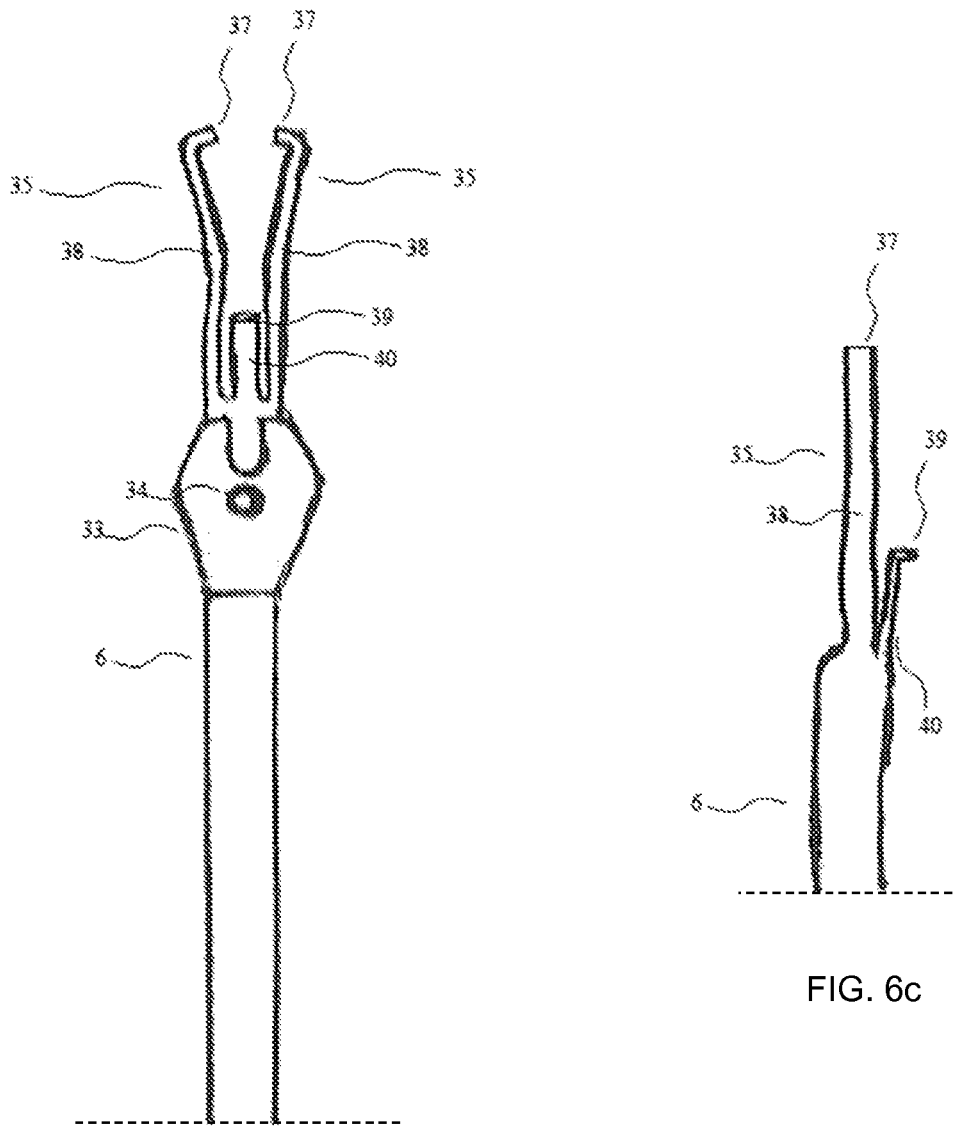

In one embodiment, the nozzle is coupled to the proximal length of guide (e.g. 6) by a locking member (e.g. a low profile coupler or locking member for allowing insertion without trauma) that secures the nozzle to the proximal length of guide (e.g. 6) to form the mandrel guide (e.g. 2). Optionally, the locking member is a sliding nozzle lock (e.g. 33), for example, as shown in FIG. 6. Other locking members include a threaded lock, for example, a lock with a threaded lumen which may, for example, be slid down the proximal length of guide, and screwed onto a distal portion of the proximal length of guide that has been threaded on its surface, such that the distal portion of the lock also surrounds (or partially surrounds) the nozzle (e.g. by screwing onto a nozzle having a similarly threaded surface) or securing members which extend from the distal end of the proximal length of guide onto the nozzle. Optionally, the nozzle lock has a cylindrical or cylinder-like shell or surface. Optionally, the nozzle lock has lateral cross sections with a circular shell or surface conical or cone-like shell or surface throughout a substantial longitudinal distance thereof (e.g. at least about 70%, 80%, 90%, or 100% of its length). Optionally, such a nozzle lock comprises a lateral cross section with a greater diameter in the middle than at the proximal and/or distal ends thereof, for example, to provide a taper on the proximal and/or distal end (e.g. as set forth in FIGS. 6a and 6b).

Optionally, the sliding nozzle lock is held in locking position by engaging one or more members fixed to one or more of the proximal length of guide (e.g. 6) and nozzle 8. Optionally, the sliding nozzle lock is threaded on the lumen and held in locking position by threads on the surface of the proximal length of guide and/or nozzle. Other locking mechanisms include a bushing with set screw or a disposable instrument with lock glued in place. Optionally, the one or more members comprise a lock engaging member, such as a pin (e.g. 39), which engages the nozzle lock, for example, as shown in FIG. 6. Optionally, the pin (or other lock engaging member) engages the nozzle lock at a receiver (e.g. pin receiver) located on the nozzle lock. Optionally, the pin-receiver is a pin hole (e.g. 34), for example, as shown in FIG. 6. Optionally, the pin is biased for engaging the nozzle lock. Optionally, the biased pin automatically engages the nozzle lock when the nozzle lock is in the correct position, for example, when the pin-receiver is aligned with the pin. Optionally, the pin is biased by a spring. Optionally, the spring is a flat spring or leaf spring (e.g. 40), for example, as shown in FIG. 6. Optionally, the spring and pin a formed as a single unit, such as a flat spring (e.g. 40) with a pin (e.g. 39) mounted thereon. Optionally, the spring is formed as a single unit with the proximal length of guide (e.g. 6). Optionally, the spring, pin, and proximal length of guide (e.g. 6) are formed as a single unit.

Figure 13:
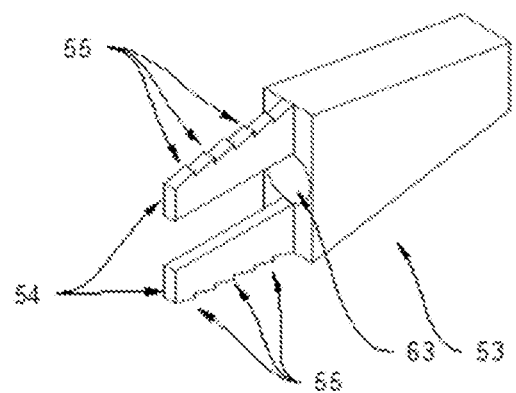
FIG. 13 depicts a reversible nozzle coupler comprising a quick-connect nozzle lock of the present invention.

In one embodiment, the nozzle is coupled to the proximal length of guide (e.g. 6) by a coupler (e.g. a low profile coupler for allowing insertion without trauma) gripping members such outer jaws (e.g. as seen in FIG. 6b) or inner gripping members (e.g. as seen in FIG. 13) fixed to and extending from the first member (e.g. 6 or 8) that secure the other member (e.g. 8 or 6) to the first member to form the mandrel guide. Examples of such couplers are depicted in FIG. 6 and FIG. 13. Optionally, jaws (e.g. 35) fixed to and extending from the proximal length of guide (e.g. 6) secure the nozzle to the proximal length of guide (e.g. 6) to form the mandrel guide (e.g. 2). Optionally, jaws fixed to and extending from the nozzle secure the proximal length of guide (e.g. 6) to the nozzle to form the mandrel guide (e.g. 2). Optionally the inner griping members are serrated. Optionally, the nozzle is non-cylindrical (e.g. shaped for delivering nanoplates).

Optionally, the jaws are biased in the open position. Optionally, the jaws are biased for securing the coupled member. Optionally, the jaws are biased by spring. Optionally, the jaws are constructed as a plurality of members that are biased inward or outward. Optionally, the jaws are constructed as two opposing members 38 that are biased in opposing directions, for example, as shown in FIG. 6.

Optionally, the jaws are locked or otherwise fixed in position for securing the coupled member (e.g. 6 or 8) by a locking member. Optionally, the locking member is a sliding lock 33, for example, as shown in FIG. 6.

Optionally, the nozzle is reversibly secured to the proximal length of the guide by two mechanisms. Optionally, the two mechanisms comprise jaws (e.g. 35) and a locking member (e.g. 33), for example, as shown in FIG. 6. Optionally, one or more of the jaws (e.g. 35) comprise a spring, such as a flat spring (e.g. 38) for biasing the jaws, for example, as shown in FIG. 6. Optionally, the jaws (e.g. 35) are biased into a non-securing position, but are forced into securing position by a locking member, (e.g. 33), for example, as shown in FIG. 6. Optionally, the locking member is a sliding lock (e.g. 33), that forces the non-secured but biased jaws, for example, as shown in FIG. 6b, into securing position, for example, as shown in FIG. 6b.

Optionally, one or more of the jaws have a gripping member that engages the coupled member. Optionally, the gripping member comprises a tooth (e.g. 37). Optionally, the coupled member (e.g. 6 or 8) has one or more gripping members receivers that engage the one or more gripping members. Optionally, the gripping member receiver comprises a hole (e.g. 34) that engages a tooth (e.g. 37) of the gripping member, for example, as shown in FIG. 6.

Optionally, jaws secure the nozzle (e.g. 8) to the proximal length of the guide by two gripping members. Optionally the two gripping members provide force in two different directions. Optionally the different directions of force are lateral and longitudinal force. Optionally, two arms of respective jaws (e.g. 35) provide lateral force while teeth (e.g. 37) of the jaws (e.g. 35) provide longitudinal and/or lateral force to the coupled member.

Figure 16:
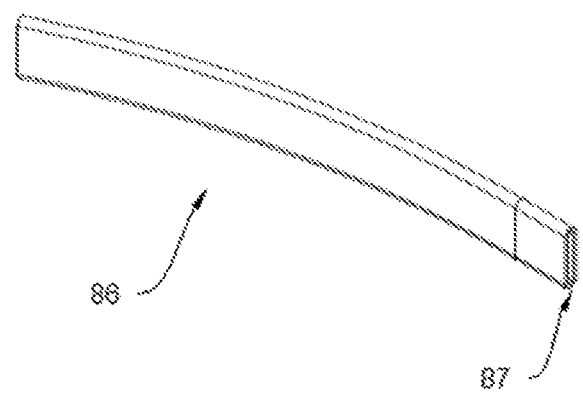
FIG. 16 depicts a non-cylindrical, oblate, nozzle of the present invention.

In one embodiment, the nozzle is coupled to the proximal length of guide by a reversible coupler (e.g. a low profile coupler for allowing insertion without trauma) comprising inner gripping members. Optionally, the inner gripping members are serrated, for example, to enhance grip on the nozzle. Optionally, the inner gripping members are rigid. Optionally, the inner gripping members are rigid and serrated. For example, the nozzle 86 of depicted in FIG. 16 is optionally coupled to the nozzle coupler 53 depicted in FIG. 17.

In one embodiment the mandrel guide is a modular mandrel guide. The proximal length of sleeve of a modular mandrel guide comprises two members which are reversibly coupled to each other such as by a key/keyway type coupler. Optionally, the first member is mandrel guide base ('modular mandrel guide base') and the second member is a nozzle holder, for example, a nozzle holder comprising nozzle coupler. A key/keyway coupler is optionally any key/keyway type coupler known in the art such as those of the male-female interaction type. A key/keyway coupler is optionally provided, for example as male member having prism or prism-like shape (e.g. a rectangular prism) and female member having prism or prism-like bore, hallow, or void, that is match fit to accept the first member. The key/keyway coupler is configured to "snaps" into coupling position, for by providing one or more of a groove, lip, collar, or clip. For example, as detailed in Example 15 and illustrated in FIG. 20b, the female member an o-ring 58 or other collar that "snaps" into a groove 97 in the male member 61. With the teachings provided herein, the skilled artisan can now readily provide functional key/keyway type couplers for modular mandrel guides. As with any mandrel guide or proximal length of guide taught herein, the modular mandrel guide comprises a guide for a mandrel, for example, a cannula extending longitudinally from end to end.

Figure 20C:
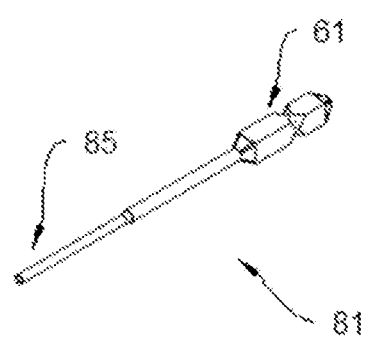
Figure 20D:
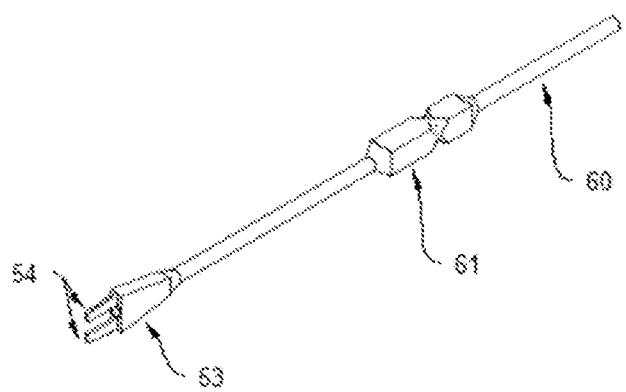
Figure 21A:
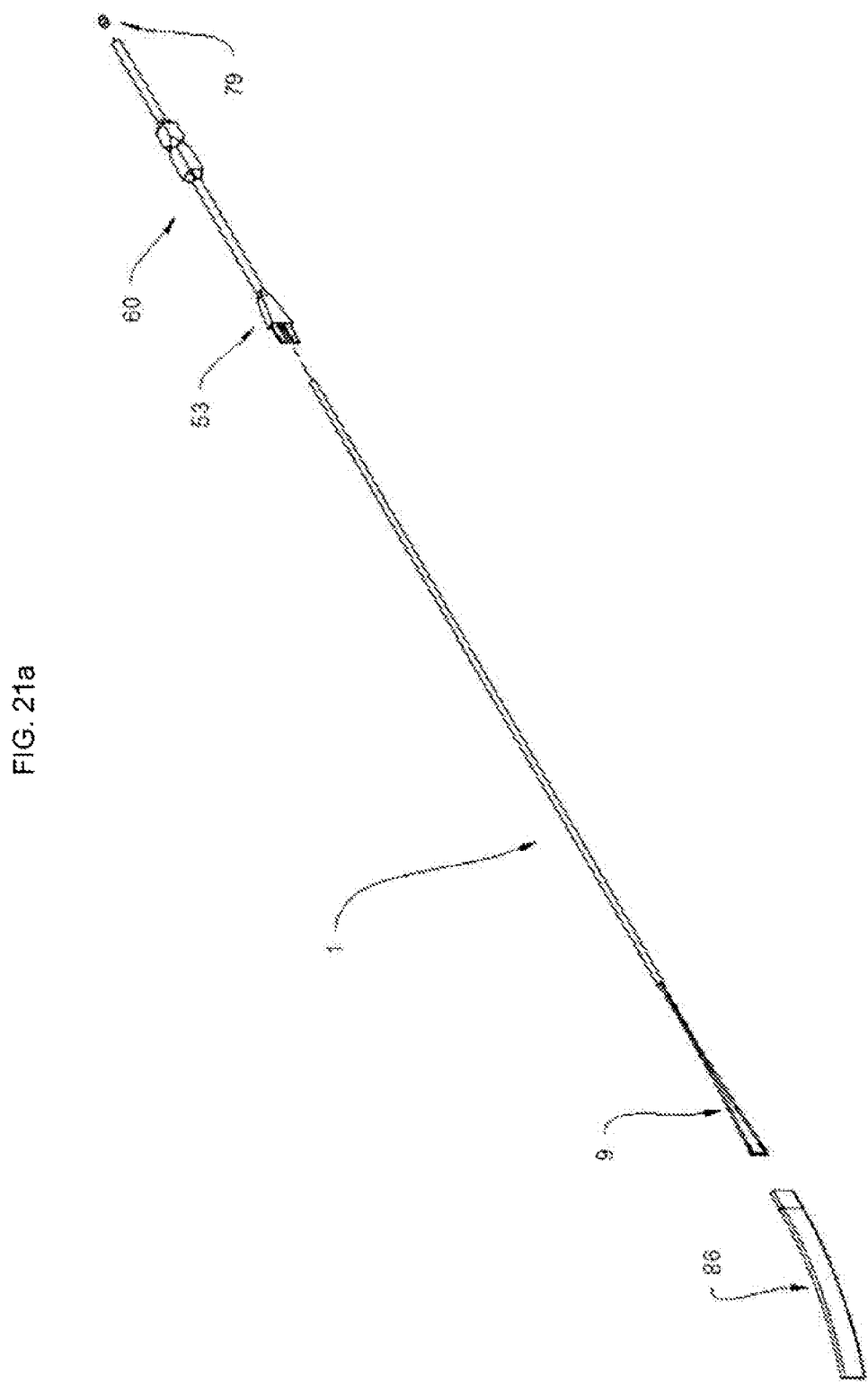
FIG. 21 depicts a mandrel, nozzle holder, and nozzle of the present invention.
Figure 21B:
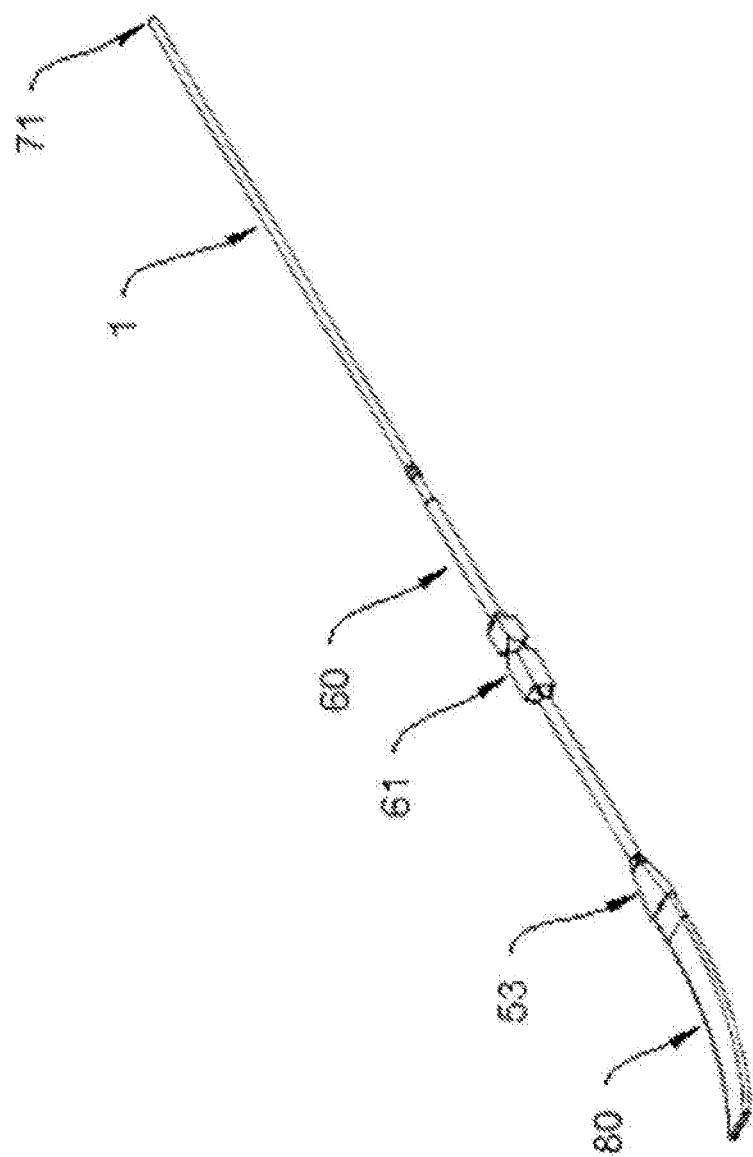
Figure 22A:
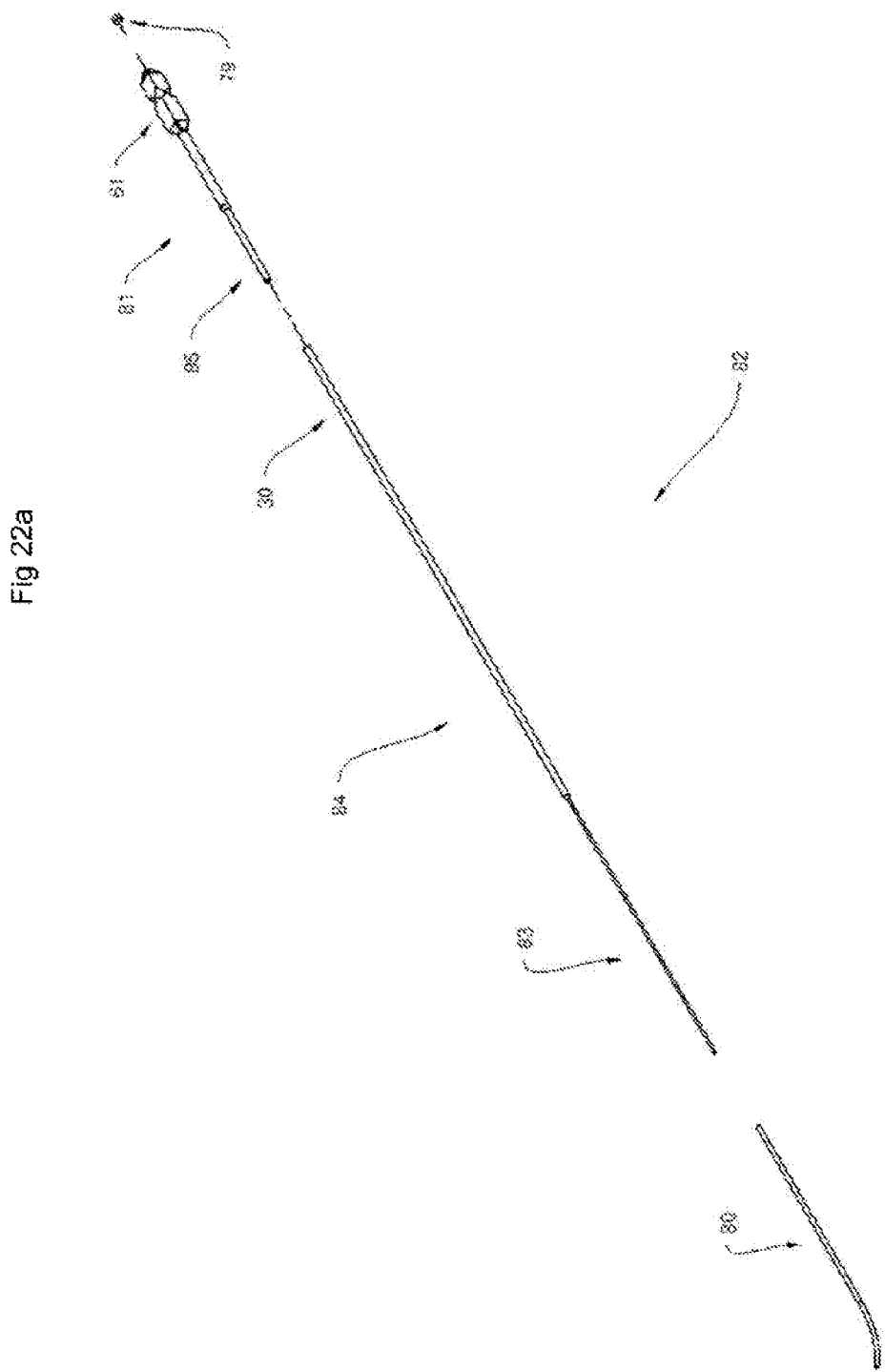
FIG. 22 depicts a mandrel, nozzle holder, and nozzle of the present invention.

The modular mandrel guide allows, for example, the alternative use of a plurality of nozzles, each associated with a different nozzle holder. For example, nozzle holder 81 (FIG. 20c) is optionally coupled to nozzle 80 (FIG. 19a), for use with mandrel 82 (FIG. 18a), as illustrated in FIG. 22a and FIG. 22b. Similarly, nozzle holder 60 (FIG. 20d) is optionally coupled to nozzle 86 (FIG. 16), for use with the mandrel of FIG. 5a, as illustrated in FIG. 21a and FIG. 21b.

Figure 24:
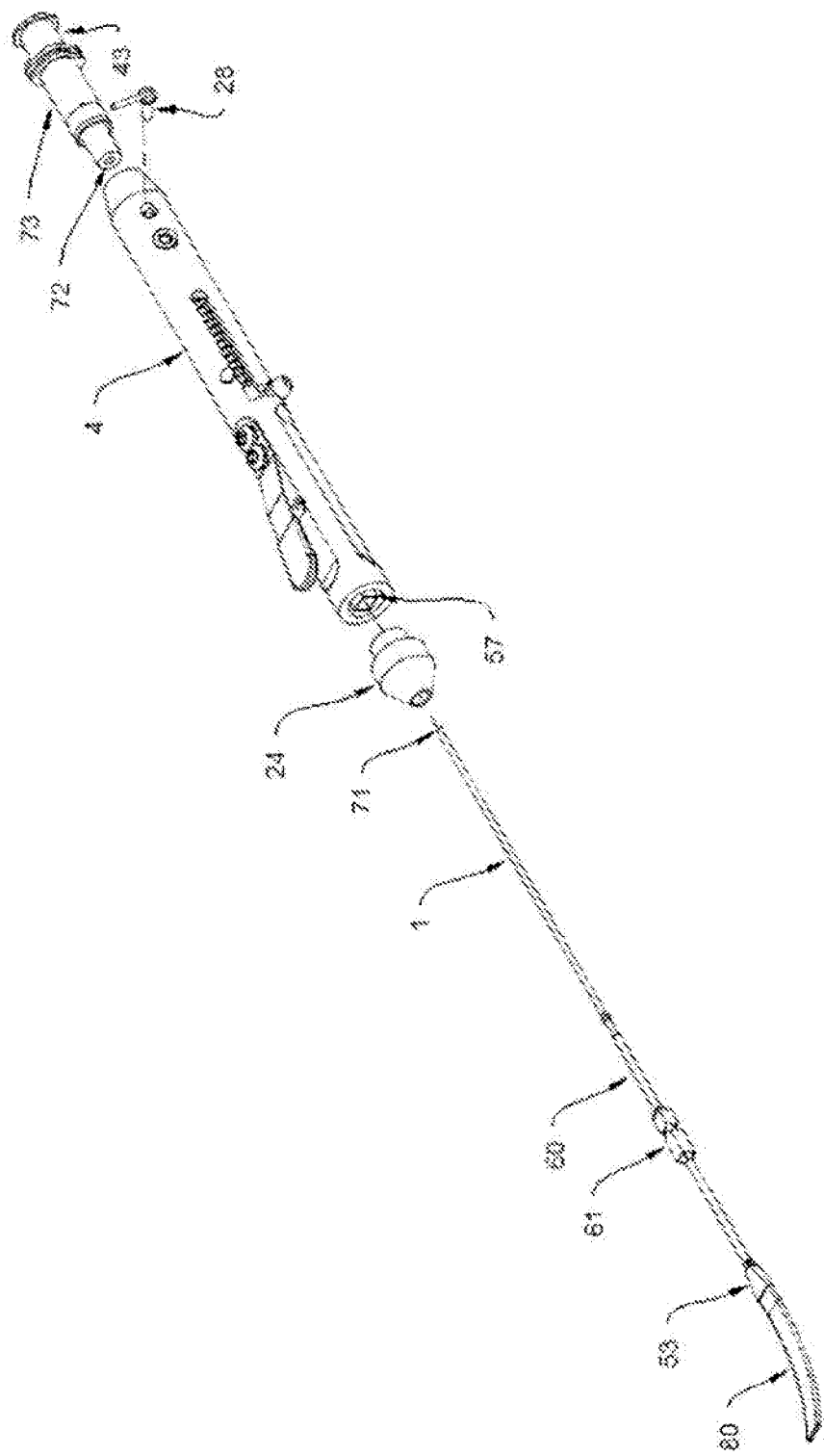
FIG. 24 depicts a delivery device of the present invention.
Figure 25:
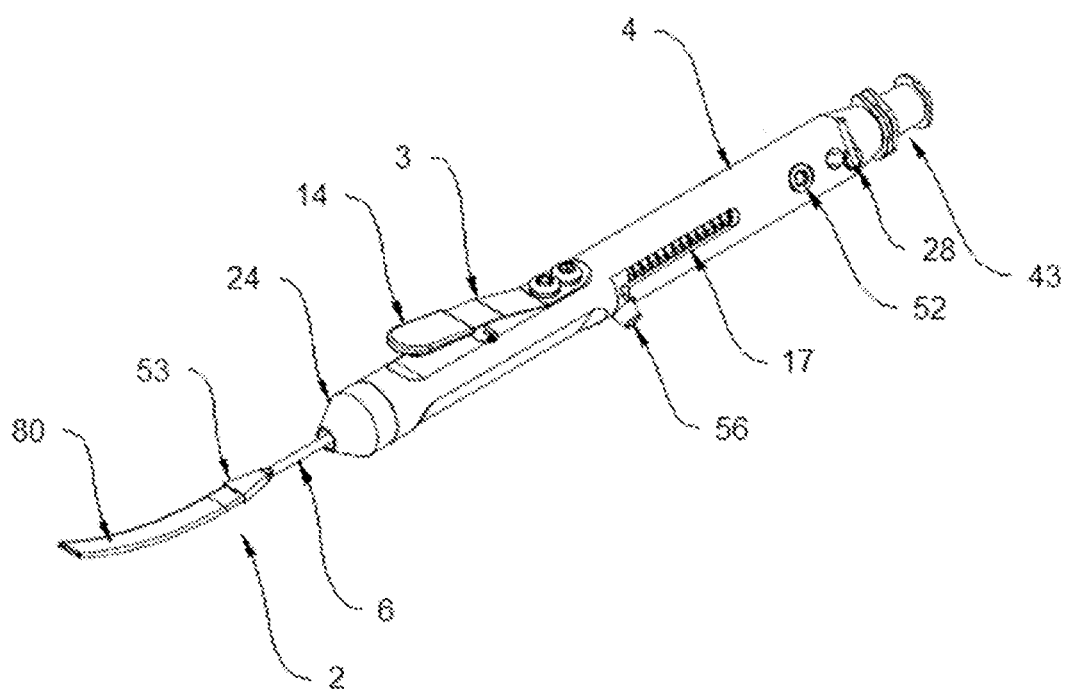
FIG. 25 depicts a delivery device of the present invention.

The reversible coupler of the modular mandrel guide is optionally provided as a key/keyway coupler such that the base of the modular mandrel guide is optionally assembled with interchangeable nozzle holders and their respective nozzles and mandrels. For example, a delivery device is optionally provided as depicted in FIG. 24 with keyway 57 such that either of the nozzle holders (and their respective mandrels) depicted in FIG. 24 or FIG. 22b can be used (FIG. 25 depicts a fully assembled delivery device).

Accordingly, the delivery device is optionally provided in a kit comprising the modular mandrel guide base and one or more sets, wherein each set comprises a mandrel and its respective nozzle (e.g. a nozzle which is size matched for the mandrel) and nozzle holder. If a plurality of sets are provided, each set is optionally different or the same. As an alternative to the kit or full device, a partial delivery device is provided comprising the delivery unit support, delivery controller, and modular mandrel guide, i.e. the delivery device without the mandrel, nozzle, and/or nozzle holder. Although the delivery device is optionally provided as a disposable device, the user can then use a single partial delivery device with his choice of the mandrel, nozzle, and/or nozzle holder.

Delivery Controller

Longitudinal movement of the mandrel relative to the mandrel guide is controlled by operably linking the delivery unit to a delivery controller and providing the delivery controller to be engagable and operable by the user's operating member, whereby activation or operation of the delivery controller induces the mandrel to move longitudinally relative to the mandrel guide.

The delivery controller is optionally configured in any manner that provides an interface between the delivery unit and the user's operating member. The operating member is optionally a part of a human user, such as an appendage of a physician, or is optionally a component of a robotic instrument or other tool used as an operating member. In one embodiment, a delivery controller is provided that interfaces with a user's finger. Optionally, a delivery unit support (e.g.) comprises a handpiece and a delivery controller is provided that interfaces with a finger of the wielding hand. Optionally, the configuration of the delivery controller allows precise control and ease of rotation within the eye.

Surprisingly, devices of the present invention which include delivery controller taught herein optionally have one or more of the following properties: allow more precise movement of the delivery unit support; allow more precise placement of the nozzle tip at the target site; allow more precise longitudinal movement of the mandrel relative to the mandrel guide; and are less interfered with by secondary devices (e.g. scopes) than those described by the prior art, for example, those described in U.S. Pat. No. 6,159,218 and U.S. Pat. No. 6,156,042. This is especially true for, for example, eye implantation devices such as retinal tissue delivery devices.

For example, when the nozzle (e.g. a curved nozzle) is inserted into a subject (e.g. at a given depth), the delivery devices are sometimes rotated or otherwise manipulated in order to place the nozzle tip at the target site. While using the devices described in, for example, U.S. Pat. No. 6,159,218 and U.S. Pat. No. 6,156,042, the user may not release his or her finger from the finger-interface without causing retraction of the nozzle (or longitudinal movement of the mandrel relative to the nozzle or mandrel guide). However, non-limiting delivery controllers taught herein allow disengagement of release of pressure (e.g. finger pressure) from the delivery controller without further allowing substantial longitudinal movement of the mandrel relative to the mandrel guide. Surprisingly, this feature can be especially useful when combined with conductive mandrels that perform secondary activities because it protects against unwanted movement of the loaded substance while performing the secondary activities (e.g. infusion/aspiration or diathermy). Further surprising is that this feature is especially useful when the user wishes to rotate his or her hand (e.g. to correctly place the tip of a curved nozzle), as it becomes even more difficult to apply a steady pressure with the finger while moving or rotating the delivery unit support, for example, when using eye implantation devices such as retinal tissue delivery devices. This feature is not present in devices which use the linkage described in U.S. Pat. No. 6,159,218 and U.S. Pat. No. 6,156,042, e.g. where longitudinal distance of the mandrel relative to the nozzle or mandrel guide is a function of the lateral distance of the user interface of the delivery controller.

In one embodiment, the delivery unit is operably linked to a delivery controller, wherein upon engagement and operation of the delivery controller by a user's operating member, a longitudinal force is applied to the mandrel or mandrel guide, thereby moving the mandrel or mandrel guide from a first longitudinal position towards a second longitudinal position at a desired rate; and wherein, at one or more intermediate positions between said first and second positions, the component immediately discontinues longitudinal movement (e.g. within 1 mm of longitudinal movement) upon the user's operating member disengaging or releasing pressure from the delivery controller. Optionally, the user's operating member is a finger or finger tip. Optionally, the delivery controller is configured to be operated with a force of less than about 3 lbs (e.g. less than about any of: 2 lbs, 1 lb, or ¾ lb; or about any of: 0.25 lb to 2 lb, 0.25 lb to 1 lb, or 0.25 lb to 0.75 lb; or about 200 g to about 500 g; or about 300 g). Optionally, the device further comprises a mandrel with conductive members, as taught herein. Optionally, the device further comprises a non-cylindrical nozzle and/or a nozzle that is curved when in position for delivery.

Surprisingly, certain devices of the present invention comprise delivery controllers which extend a minimal distance laterally from the delivery unit support (e.g. handpiece), thereby reducing bulk and potential interference or obstruction to or with secondary devices (e.g. a scope), and allowing more precise manipulation of the device. Additionally or alternatively, delivery controllers taught herein provide devices which impart a reduced angle formed between the users interacting member (e.g. a finger) and the delivery unit support or user (e.g. hand, palm, wrist, or non-interacting finger), and which are less awkward to manipulate and more precisely manipulated, especially while, for example, rotating the delivery unit support (e.g. handpiece). This is especially true when using, for example, eye implantation devices such as retinal tissue delivery devices. These features are not present in devices which use the linkage described in U.S. Pat. No. 6,159,218 and U.S. Pat. No. 6,156,042, e.g. where longitudinal distance of the mandrel relative to the nozzle or mandrel guide is a function of the lateral distance of the user interface of the delivery controller. Optionally, the delivery controller is configured to be operated with a force of less than about 3 lbs (e.g. less than about any of: 2 lbs, 1 lb, or ¾ lb, or about any of: 0.25 lb to 2 lb, 0.25 lb to 1 lb, or 0.25 lb to 0.75 lb, or about 200 g to about 500 g, or about 300 g).

When the delivery unit (e.g. 5) is in the loaded position, the mandrel (e.g. 1) is in a retracted state relative to the mandrel guide (e.g. 2). Delivery of the substance is accomplished by advancing the mandrel (e.g. 1) relative to the mandrel guide (e.g. 2) until the substance is ejected from the device. Such advancement and retraction is achieved by operating the delivery controller (e.g. 3).

With the teachings provided herein, one skilled in the art can now readily design function operably linkages between the delivery controller (e.g. 3) and the delivery unit (e.g. 5) such that activation or operation of the delivery controller (e.g. 3) induces force to move the mandrel (e.g. 1) to move longitudinally relative to the mandrel guide (e.g. 2). For example, the delivery controller (e.g. 3) is optionally operably linked to the delivery unit (e.g. 5) by providing linkage from the delivery controller (e.g. 3) to either the mandrel (e.g. 1) or the mandrel guide (e.g. 2) while the other member 2 or 1 is relatively fixed to the delivery unit support (e.g. 4).

Relative to the force applied to the delivery controller (e.g. 3), the force induced on the mandrel (e.g. 1) or mandrel guide (e.g. 2) is optionally direct (e.g. operably linking the delivery controller (e.g. 3) to the delivery unit (e.g. 5) by locking the mandrel to the delivery controller (e.g. 3)) or indirect (e.g. operably linking the delivery controller (e.g. 3) to the delivery unit (e.g. 5) through levers, pulleys, motors, etc). The indirect force is optionally an actuated force, an assisted force, or an unassisted force. An actuated force is an indirect force experienced by the delivery unit that is set in motion by activation the delivery controller (e.g. 3) by the user's operating member but is exerted by another member of the device (of spring, air, pressurized gas, or motor). An assisted force is an indirect force where the work applied to the delivery unit (e.g. 5) is greater than the work applied to the delivery controller (e.g. 3) from the users operating member (e.g. by use of spring, air, pressurized gas, or motor) or unassisted, i.e. where the operable linkage merely changes the direction of applied force (e.g. by use of only a pulley or lever).

In one embodiment, the device comprises a delivery unit comprising a mandrel guide, wherein the mandrel guide has an open distal end for discharge of a substance if loaded in the mandrel guide; and a longitudinally elongated mandrel disposed internally to the mandrel guide, whereby relative longitudinal movement of the mandrel through the mandrel guide towards the open distal end biases the loaded substance to move longitudinally towards the open end. The delivery controller comprises a sliding member operably linked (e.g. fixed) to the delivery unit, whereby sliding the sliding member imparts a force on the delivery unit to bias the delivery unit for the relative longitudinal movement (e.g. as set forth in FIG. 4 or 7).

Optionally, the delivery unit support comprises a handpiece and the sliding member is configured to interface a with a user's finger. Optionally, the sliding member slides longitudinally about the delivery unit. Optionally, the sliding member has lateral height (e.g. extending from the handpiece) of less than about one inch, or less than about or about the width of the interfacing finger. Optionally, the sliding member is mounted on the mandrel guide, whereby sliding the sliding member towards the proximal end of the mandrel imparts a force on the mandrel guide to move the mandrel guide longitudinally towards the proximal end of the mandrel to discharge a loaded substance (e.g. as set forth in FIG. 4). Optionally, the sliding member is mounted the mandrel; whereby sliding the sliding member towards the distal end of the mandrel guide imparts a force on the mandrel to move the mandrel longitudinally towards the distal end of the mandrel guide to discharge a loaded substance (e.g. as set forth in FIG. 7).

Figure 4:
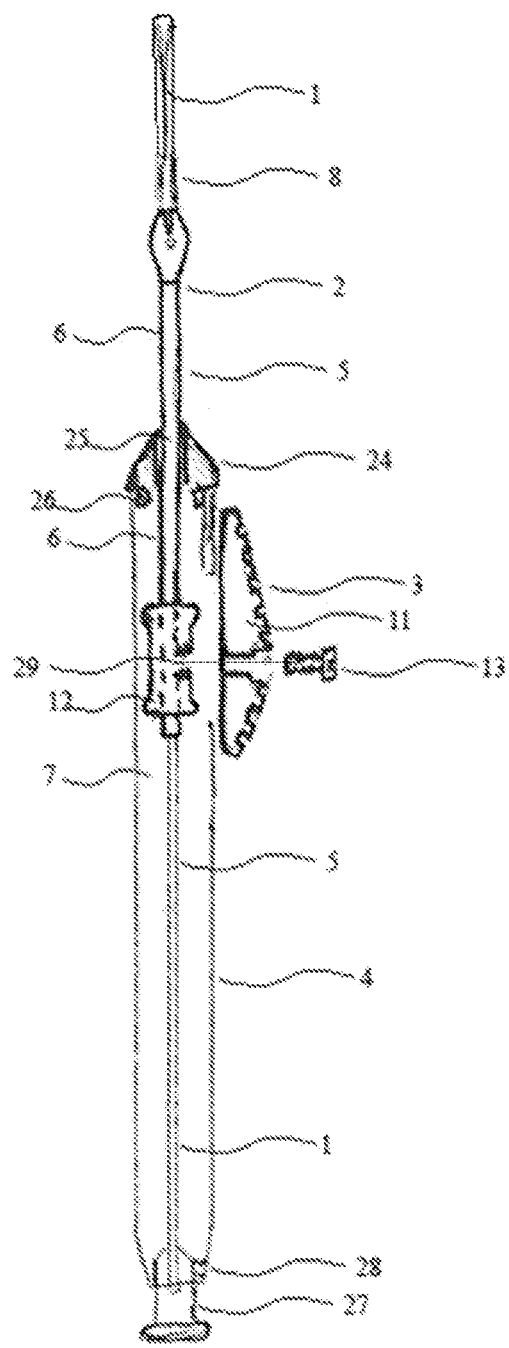
FIG. 4 depicts a device of the present invention with passive action and slidable delivery controller.

In one embodiment, the delivery controller (e.g. 3) comprises a sliding member (e.g. 11) disposed externally of the delivery unit support (e.g. 4), for example, as shown in FIG. 4. The sliding member (e.g. 11) is operably linked (e.g. fixed) to the delivery unit (e.g. 5) such that longitudinal movement sliding member (e.g. 11) longitudinally moves the mandrel (e.g. 1) relative to the mandrel guide (e.g. 2). One skilled in the art will readily appreciate how to interface the sliding member (e.g. 11) with the delivery unit (e.g. 5) to provide such an operable linkage. For example, the sliding member (e.g. 11) is optionally fixed to a mandrel or mandrel guide of the delivery unit (e.g. 5). Optionally, the sliding member (e.g. 11) is fixed to the mandrel or mandrel guide through a rack (e.g. 12) mounted on the mandrel or mandrel guide, for example, as shown in FIG. 4. Optionally, the sliding member (e.g. 11) is fixed to the member by a locking screw 13 inserted through the sliding member (e.g. 11) and screw locked to the mandrel or mandrel guide of the delivery unit (e.g. 5), for example, screw locked into a threaded hole 29 of rack (e.g. 12).

In one embodiment, the device comprises a delivery unit comprising a mandrel guide, wherein the mandrel guide has an open distal end for discharge of a substance if loaded in the mandrel guide; and a longitudinally elongated mandrel disposed internally to the mandrel guide, whereby relative longitudinal movement of the mandrel through the mandrel guide towards the open distal end biases the loaded substance to move longitudinally towards the open end.

In one embodiment, the device comprises a delivery unit comprising a mandrel guide, wherein the mandrel guide has an open distal end for discharge of a substance if loaded in the mandrel guide; and a longitudinally elongated mandrel disposed internally to the mandrel guide, whereby relative longitudinal movement of the mandrel through the mandrel guide towards the open distal end biases the loaded substance to move longitudinally towards the open end. The device further comprises a delivery unit biasing member, such as a spring (e.g. tension spring or coaxial spring such as part 17 of FIG. 8) imparting a force on the delivery unit to bias the delivery unit for the relative longitudinal movement (e.g. to bias the delivery unit for delivering a loaded substance). Optionally, the device further comprises a safety switch (e.g. safety pin configured to move longitudinally with the delivery unit and moved laterally into and out of a safety latch to prevent longitudinal movement) to oppose the bias of the delivery unit basing means, thereby preventing said longitudinal movement of the delivery unit, regardless of whether or not the delivery unit engagement means is engaged or disengaged with the delivery unit.

In one embodiment, the device comprises a delivery unit comprising a mandrel guide, wherein the mandrel guide has an open distal end for discharge of a substance if loaded in the mandrel guide; and a longitudinally elongated mandrel disposed internally to the mandrel guide, whereby relative longitudinal movement of the mandrel through the mandrel guide towards the open distal end biases the loaded substance to move longitudinally towards the open end. The device further comprises a delivery unit biasing member, such as a spring (e.g. tension spring or coaxial spring such as part 17 of FIG. 8) imparting a force on the delivery unit to bias the delivery unit for the relative longitudinal movement (e.g. to bias the delivery unit for delivering a loaded substance). The delivery controller comprises a delivery unit engagement means for engaging the delivery unit (e.g by way of the mandrel or mandrel guide), to prevent (e.g. impede, slow, or halt) delivery unit movement that would otherwise be induced by the delivery unit biasing member, whereby operation of the delivery controller engages and/or disengages the a delivery unit engagement means with and/or from the delivery unit.

In such an embodiment, the delivery unit engagement means, for example, prevents delivery unit movement by imparting an opposing force selected from a normal force using a knife edge lock or a frictional force using a traction pad. Although the present invention provides examples of knife edge locks which interact with ratchet racks, such knife edge locks are not limited thereto. With the teachings provided herein, the skilled artisan can now readily provide functional knife edge locks that prevent longitudinal movement of a delivery unit when engaged. For example, a knife edge lock is optionally any member which contacts the delivery unit to impart a normal force thereto, to prevent longitudinal movement. Although the present invention provides examples of traction pads which comprise a layer of friction-inducing pad (e.g. silicon tubing), such traction pads are not limited thereto. With the teachings provided herein, the skilled artisan can now readily provide functional traction pads that prevent longitudinal movement of a delivery unit when engaged. For example, a traction pad is optionally any member which contacts the delivery unit to impart a frictional force to prevent longitudinal movement. The skilled artisan will also realize that the configuration of either a knife edge lock or a traction pad may, in some cases, be dependent on the choice of material, the shape, or the configuration of the delivery unit engagement means and/or delivery unit.

Optionally, the delivery unit engagement means comprises a knife edge lock configured for engaging and disengaging one or more ratchet teeth provided on a delivery unit, whereby operation of the delivery controller engages and/or disengages the knife edge lock from the delivery unit, for example, from one or more ratchet teeth (e.g. as set forth in FIG. 8 or 9). Optionally, operation of the ratchet comprises less than about any of: 5, 4, 3, 2, or 1 millimeters of movement perpendicular to the length of mandrel guide inserted into the subject. Optionally, operation of the ratchet is adjustable for both actuating pressure and perpendicular movement.

Figure 10:
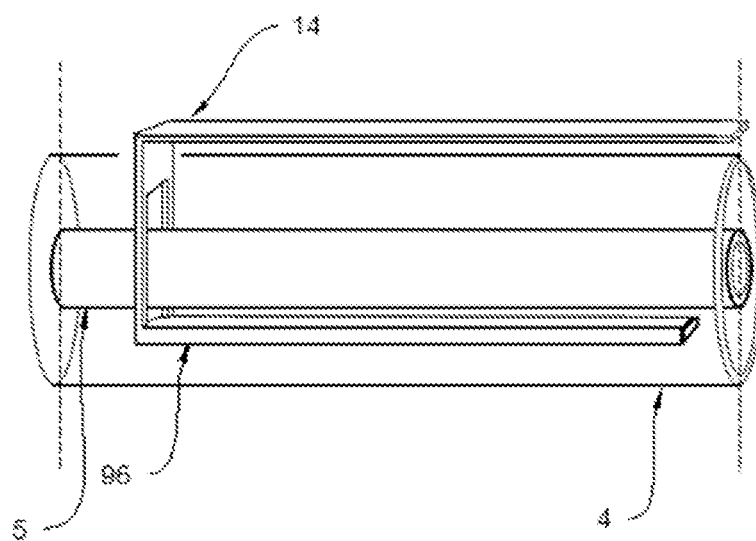
FIG. 10 depicts a push-button delivery controller of the present invention comprising a delivery unit engagement means.

Optionally, the delivery unit engagement means comprises a traction pad or other length of material which provides traction on a member of the delivery unit (e.g. the mandrel or mandrel guide) to impede, slow, or halt (e.g. immediately halt such as within 1 or 0.5 mm of) movement induced by the delivery unit biasing member (e.g. as shown in FIG. 10). Optionally, the delivery unit engagement means comprises a clamp that engages and/or disengages a member of the delivery unit (e.g. the mandrel or mandrel guide) to impede, slow, or halt (e.g. immediately halt such as within 1 or 0.5 mm of) movement induced by the delivery unit biasing member In one embodiment, the device comprises a delivery unit comprising a mandrel guide, wherein the mandrel guide has an open distal end for discharge of a substance if loaded in the mandrel guide; and a longitudinally elongated mandrel disposed internally to the mandrel guide, whereby relative longitudinal movement of the mandrel through the mandrel guide towards the open distal end biases the loaded substance to move longitudinally towards the open end. The device further comprises a delivery unit biasing member, such as a spring (e.g. tension spring or coaxial spring such as part 17 of FIG. 8) imparting a force on the delivery unit to bias the delivery unit for the relative longitudinal movement (e.g. to bias the delivery unit for delivering a loaded substance). The delivery controller comprises a delivery unit engagement means for engaging the delivery unit (e.g by way of the mandrel or mandrel guide), to prevent (e.g. impede, slow, or haft) delivery unit movement that would otherwise be induced by the delivery unit biasing member, whereby operation of the delivery controller engages and/or disengages the a delivery unit engagement means with and/or from the delivery unit. In this embodiment, the delivery unit engagement means, for example, prevents delivery unit movement by imparting an opposing force selected from a normal force using a knife edge lock or a frictional force using a traction pad. Optionally, the device further comprises a safety switch (e.g. safety pin configured to move longitudinally with the delivery unit and be moved laterally into and out of a safety latch to prevent longitudinal movement) to oppose the bias of the delivery unit basing means, thereby preventing said longitudinal movement of the delivery unit, regardless of whether or not the delivery unit engagement means is engaged or disengaged with the delivery unit.

In one embodiment, the device further comprises a delivery unit biasing member (e.g. a spring such as a coaxial or tension spring) imparting a force on the delivery unit to bias the delivery unit for delivery (e.g. imparting a force on the mandrel to move towards the distal end of the mandrel guide or imparting a force on the mandrel guide to move towards the proximal end of the mandrel). Optionally, a means for engaging the delivery unit engagement means, for example, one or more ratchet teeth, is mounted the mandrel guide; and the biasing member imparts a force on the mandrel guide to move longitudinally towards the proximal end of the mandrel to discharge a loaded substance (e.g. as set forth in FIG. 9). Optionally, a means for engaging the delivery unit engagement means, for example, one or more ratchet teeth, is mounted the mandrel; and the biasing member imparts a force on the mandrel to move longitudinally towards the distal end of the mandrel guide to discharge a loaded substance (e.g. as set forth in FIG. 8).

When a delivery unit engagement means is provided for preventing longitudinal movement of a delivery unit, the delivery controller optionally comprises a biasing member for biasing (or other delivery controller biasing means) the delivery unit engagement means (e.g. biasing member for a knife edge or traction pad) to engage the delivery unit. For example, the biasing member is optionally configured for biasing the knife edge lock to engage one or more teeth (e.g. forming the delivery controller as a flat spring toggle (e.g. 14), as set forth in FIG. 8); whereby applying a user force against the knife edge biasing member disengages the delivery unit engagement means (e.g. knife edge) from means for engaging the delivery unit engagement means (e.g. one or more ratchet teeth) to allow the relative movement of the mandrel through the mandrel guide. Further, a safety switch is optionally provided to prevent longitudinal movement of the delivery unit.

Figure 7:
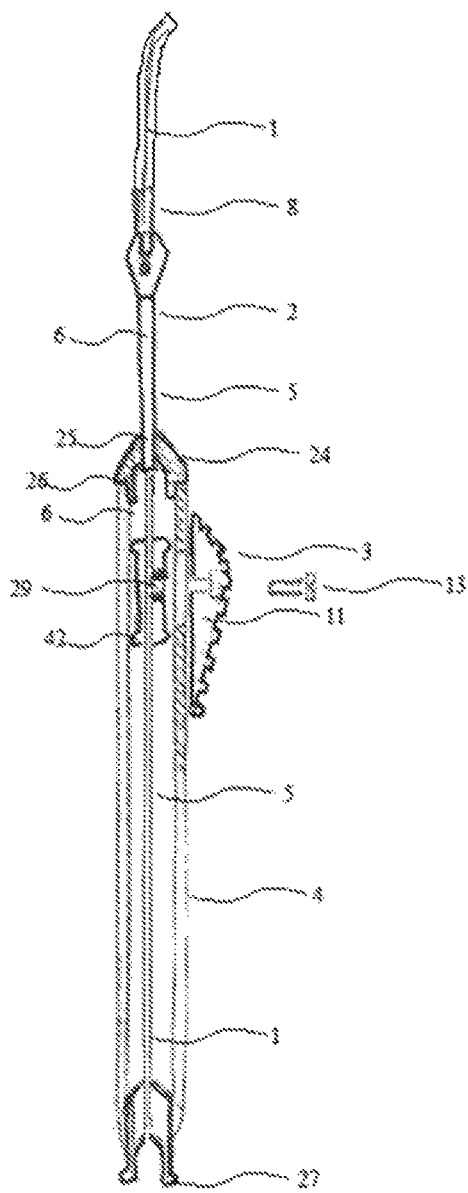
FIG. 7 depicts a device of the present invention with positive action and slidable delivery controller.

In one embodiment, the delivery unit support comprises a handpiece, wherein the delivery controller comprises a toggle configured to interface a user's finger (e.g. as set forth in FIG. 7 or 8). Optionally, the device further comprises force-adjusting means (e.g. spring bushings having adjustable positions relative to the delivery unit) to adjust the force of the delivery unit on the delivery unit, wherein adjusting the force changes the speed of the relative longitudinal movement (e.g. as set forth in FIG. 7 or 8).

In one embodiment, means for engaging the delivery unit engagement means comprises one or more ratchet teeth and comprises at least a first ratchet tooth and a second ratchet tooth; wherein when the first ratchet tooth is aligned for engagement of the knife edge lock, the relative longitudinal movement causes the first ratchet tooth to move out of a position of alignment for engagement while causing the second tooth to move towards a position of alignment for engagement of the knife edge lock. Optionally, upon releasing the user force from the knife edge biasing member, the mandrel moves a longitudinal distance of less than about 1 mm relative to the mandrel before the knife edge lock engages a ratchet tooth and substantially halts the longitudinal movement of the mandrel relative to the mandrel guide.

In one embodiment, the delivery controller (e.g. 3) comprises a toggle (e.g. 14) disposed externally of the delivery unit support (e.g. 4), for example, as shown in FIG. 8, FIG. 10, or FIG. 23. The toggle (e.g. 14) is operably linked to the delivery unit (e.g. 5) such that activation of the toggle (e.g. 14) longitudinally moves the mandrel (e.g. 1) relative to the mandrel guide (e.g. 2).

In one embodiment, such operable linkage comprises a means for engaging the delivery unit engagement means comprising a rack (e.g. ratchet rack 48, traction pad-interfacing member, or other member or material for engaging the delivery unit engagement means) mounted on the mandrel (e.g. 1) or mandrel guide (e.g. 2). Optionally, the operable linkage comprises members of ratchet, such as members 44, 16 of a linear ratchet, for example, as shown in FIG. 8. Optionally, the operable linkage includes the surface of the mandrel (e.g. 1) or mandrel guide (e.g. 2) (e.g. when the delivery controller comprises a traction pad, clamp, or other member providing traction as delivery unit engagement means), for example, a textured surface such as grooves (e.g. provided in a steel mandrel or mandrel guide).

The toggle (e.g. 14) optionally interfaces the delivery unit (e.g. 5) through a delivery unit engagement means (e.g. a knife edge lock 15 that engages/disengages teeth 16 of a rack 44, for example, mounted on a mandrel or mandrel guide of the delivery unit (e.g. 5), as shown in FIG. 8). In the loaded position, the mandrel or mandrel guide is forcibly biased for delivery such that means for engaging the delivery unit engagement means (e.g a tooth 16 of the rack 44) contacts the delivery unit engagement means (e.g. knife edge lock 15) such that the mandrel or mandrel guide is locked with respect to its longitudinal position. Activation of the toggle (e.g. 14) disengages the delivery unit engagement means (e.g. knife edge lock 15) from the means for engaging the delivery unit engagement means (e.g. teeth 16) and allows longitudinal movement of the mandrel or mandrel guide due to the biasing force.

Optionally, a means for biasing the delivery unit comprises a spring, such as a tension spring (e.g. 17). The spring is optionally housed by a pair of bushings e.g. 19, 20), for example, as shown in FIG. 8. One bushing (e.g. 19) is secured to a mandrel or mandrel guide of the delivery unit (e.g. 5) but remains unsecured to the delivery unit support (e.g. 4) while the other bushing (e.g. 20) is secured to the delivery unit support (e.g. 4) but remains unsecured to the mandrel or mandrel guide of the delivery unit (e.g. 5) to which first bushing (e.g. 19) is secured, for example, as shown in FIG. 8 The configuration will depend on the intended mode of relative movement of the mandrel (e.g. 1) relative to the mandrel guide (e.g. 2), e.g. positive or passive action, and the type of spring used, e.g. tension or compression.

In a positive action setup, the mandrel guide (e.g. 2) is longitudinally relatively fixed to the delivery unit support (e.g. 4) while the mandrel (e.g. 1) advances through the mandrel guide (e.g. 2) to deliver the substance, for example, as shown in FIG. 8. Using a tension spring 17, bushing 19 is secured to the mandrel (e.g. 1) but remains unsecured to the delivery unit support (e.g. 4) to allow advancement of the mandrel (e.g. 1) upon disengagement of the knife edge lock 15 from the teeth 16 of a rack 44 mounted on the mandrel (e.g. 1). Bushing 20 is secured to the delivery unit support (e.g. 4) to resist expansion of tension spring 17 while the mandrel (e.g. 1) is retracted to the loaded position, but is unsecured from the mandrel (e.g. 1) to allow longitudinal movement of the mandrel (e.g. 1). Optionally, the bushing 19 is secured to the mandrel (e.g. 1) by reversible securing means, such as a locking screw 21, so that the bushing 19 can be secured at the desired longitudinal position on the mandrel (e.g. 1) to adjust the spring tension/delivery rate and/or the maximum advancement distance of the mandrel (e.g. 1).

In a passive action setup, the mandrel (e.g. 1) is longitudinally relatively fixed to the delivery unit support (e.g. 4) while the mandrel guide (e.g. 2) retracts over the mandrel (e.g. 1) to deliver the substance, for example, as shown in FIG. 9. Using a tension spring (e.g. 17), bushing (e.g. 50) is secured to the mandrel guide (e.g. 2) but remains unsecured to the delivery unit support (e.g. 4) to allow retraction of the mandrel guide (e.g. 2) over the mandrel (e.g. 1) upon disengagement of, for example, the knife edge lock 46 from the teeth (e.g. 49) of a rack (e.g. 48) mounted on the mandrel guide (e.g. 2). Bushing 51 is secured to the delivery unit support (e.g. 4) to resist expansion of tension spring 17 while the mandrel guide is advanced to the loaded position, but is unsecured from the mandrel guide (e.g. 2) to allow longitudinal movement of the mandrel guide (e.g. 2). Optionally, bushing (e.g. 51) is secured to the delivery unit support (e.g. 4) by reversible securing means, such as a locking screw (e.g. 52), so that the bushing (e.g. 23) can be secured at the desired longitudinal position on the delivery unit support (e.g. 4) to adjust the spring tension/delivery rate and/or the maximum retraction distance of the mandrel guide (e.g. 2).

Delivery Unit Support

A device of the present invention comprises a delivery unit support (e.g. 4). The delivery unit support (e.g. 4) is not limited to any design, structure, or configuration, so long as it provides one of: structural support for the delivery unit (e.g. 5), a means for arranging the mandrel and mandrel guide of the delivery unit (e.g. 5) in the appropriate configuration, and/or housing device components. The delivery unit support (e.g. 4) optionally provides a means for interfacing the device with the user, for example, by providing a graspable structure to the user for placement or manipulation of the device. Optionally, the user is a human, a tool, or a robotic instrument. The delivery unit support (e.g. 4) optionally provides a structure for coupling the device with other devices, such as vacuums, fluid pumps, optic devices, and the like. The delivery unit support (e.g. 4) optionally provides a means for interfacing with other devices, such as vacuums, liquid pumps, optic devices, and the like.

In one embodiment, the delivery unit support (e.g. 4) provides substantial casing of the inner components to provide greater surface area for user interface and/or protect the components from physical damage and/or pathogens. Optionally, the delivery unit support (e.g. 4) is provided with ports, slots, or other openings, for example, to allow passage of operable linking means between inner and outer components or to allow user access to inner components.

In another embodiment, the delivery unit support (e.g. 4) is constructed from the structure required to provide a means for arranging components of the device in the appropriate configuration, providing structural support thereto, and/or housing device components. For example, the delivery unit support (e.g. 4) is optionally provided merely as a frame or guide for device components.

The delivery unit support (e.g. 4) is optionally made from any material that provides the required functions taught herein. In one embodiment, the delivery unit support (e.g. 4) is made of stainless steel to facilitate autoclaving. In another embodiment, the delivery unit support (e.g. 4) is manufactured primarily from plastic. Optionally, the delivery unit support (e.g. 4) is manufactured from a mold. The use of plastic and/or molds in the manufacturing process is especially useful to provide a disposable delivery unit support (e.g. 4).

In one embodiment, the delivery unit support (e.g. 4) comprises an ergonomic member to optimize its use with respect to the orientation to and/or grip by the user while the device is wielded.

In one embodiment, the delivery unit support (e.g. 4), or portion thereof, comprises a housing, such as a tubular housing. Optionally, the housing, or portion thereof, is substantially cylindrical or constructed as an elongated prism or prism-like shell or shell-like structure. Optionally, the delivery unit support (e.g. 4) is constructed as a handpiece. Optionally, the handpiece is constructed for delivery of retinal tissue (e.g. has a diameter of less than 1 in, for example, less than about aby of: 0.8, 0.7 in, 0.6 in, or 0.5 in).

In one embodiment, the delivery unit support (e.g. 4) is constructed as a handpiece comprising a housing, such as a tubular housing. Optionally, the housing comprises at least one flat surface for interface with a portion of the user's hand, such as for interfacing with a finger or fingers. Optionally, the housing comprises a plurality of flat surfaces disposed about the housing. Optionally, the housing comprises three flat surfaces disposed about the housing that forms a triangular prism or prism-like portion of the housing for providing an ergonomic interface with the user's hand. Optionally, a triangular prism or prism-like portion comprises a triangular prism having blunted corners for ergonomic interface with the user's hand.

In one embodiment, a delivery unit support (e.g. 4) comprises a housing, such as a tubular housing, and is provided with a distal endcap (e.g. 24) having a port 25 to allow longitudinal acceptance and lateral or radial support of the mandrel guide (e.g. 2), for example, as shown in FIG. 8. The endcap 24 is optionally removable from the housing, for example, by threaded fit, by sliding fit, as a bayonet-style lock, and the like. Alternatively, the endcap is optionally constructed as part of the housing. In a positive action setup, for example, as shown in FIG. 8, an endcap (e.g. 24) can optionally be provided that longitudinally secures the mandrel guide (e.g. 2), for example, by a locking screw (e.g. 36) or Luer lock. In a passive action setup, for example, as shown in FIG. 9, an endcap (e.g. 24) is optionally provided that allows longitudinal movement of the mandrel guide (e.g. 2) through the port 25.

In one embodiment, a delivery unit support (e.g. 4) comprises a housing, such as a tubular housing, and is provided with a proximal endcap (e.g. 43) having a port, partial port, or fixation point for longitudinal acceptance and/or support and/or lateral or radial support of the mandrel (e.g. 1), for example, as shown in FIG. 9. The endcap is optionally removable from the housing, for example, by threaded fit, by sliding fit, by a screw lock, as a bayonet-style lock, and the like. Alternatively, the endcap is optionally constructed as part of the housing.

Optionally, a proximal endcap is provided as a Luer lock (e.g. 43) or Luer housing, as shown in FIG. 8, that interfaces with an external device (e.g. secondary device such as a fluid pump) through a Luer housing or Luer lock, respectively.

In one embodiment of a passive action setup, a proximal endcap (e.g. 43) is provided that longitudinally secures the mandrel (e.g. 1) relative to the delivery unit support (e.g. 4), for example, as shown in FIG. 9.

In one embodiment of a positive action setup, a proximal endcap (e.g. 43) is provided that allows longitudinal movement of the mandrel (e.g. 1) relative to the delivery unit support (e.g. 4), for example, as shown in FIG. 8. Optionally, the proximal endcap 43 is longitudinally secured to the mandrel (e.g. 1), but is itself allowed to slide longitudinally about the proximal end of the delivery unit support (e.g. 4), for example, as shown in FIG. 8.

In one embodiment, an interface (e.g. Luer lock) is provided for interlacing the mandrel with a secondary device such as a fluid pump.

Optional Configurations

Mandrels and mandrel guides are optionally customized in different sizes and shapes for delivery or extraction of different kinds of tissue, gels containing different trophic factors or drugs, electronic microchips, and other implantable or extractable substances. Mandrels and mandrel guides are optionally produced in sterile packages for one-time use.

In one embodiment, the mandrel guide (e.g. 2) comprises a 0-40 gauge tube. Optionally, the mandrel guide (e.g. 2) comprises a 10-40 gauge tube, such as a 10-30, 15-25, or 16-20 gauge tube (e.g. 18 gauge).

In one embodiment, the mandrel (e.g. 1) comprises a 0-40 gauge member. Optionally, the mandrel guide (e.g. 2) comprises a 10-40 gauge member, such as a 10-30, 15-25, or 18-22 gauge member.

In one embodiment, the mandrel (e.g. 1) comprises an elongated member at the proximal end that forks into a plurality of elongated members (e.g. 30 gauge) at the distal end. Optionally, the conductive members are positioned laterally of each other (e.g. for use with a nanoplate and/or sheet-shaped or rectangular nozzle) Optionally, the members are conductive members. Optionally, the conductive members are tubes. Optionally, an elongated member at the proximal end comprises 0-40 gauge tube, for example, a 10-40 gauge member, such as a 10-30, 15-25, or 18-22 gauge member and a plurality of elongated members at the distal end comprise smaller lateral cross sections, for example, a plurality of elongated members of 10-50 gauge, such as a 20-40, 25-35, or 28-32 gauge. Optionally, the members at the proximal and distal end are tubes and the plurality of elongated members at the distal end are capable of at least partially sliding into the tube at the distal end to form a functional mandrel. For example, the device detailed Example 3 or Example 4 can be configured as such.

The mandrel and mandrel guide are optionally constructed of any length, as long as they together form a functional delivery unit. Optionally, the device is configured for positive action and the mandrel guide is 2-20 cm, such as 6-15 cm, and the mandrel is 10-40 cm, such as 20-30 cm. Optionally, the device is configured for passive action and the mandrel guide has a length of 10-20 cm, such as 12-16 cm, and the mandrel has a length of 10-40 cm, such as 20-30 cm. Optionally, the nozzle has a length of 2-15 cm, such as 4-10 cm.

In one embodiment, the device is useful for delivery of a substance into an eye, for example, delivery of retinal tissue. Optionally, the mandrel guide (e.g. 2) and the mandrel (e.g. 1) each comprise a 10-40 gauge tube, such as a 10-30, 15-25, or 16-20 gauge tube, wherein the mandrel (e.g. 1) is sized to slide through the mandrel guide (e.g. 2). Optionally, the mandrel guide (e.g. 2) comprises a 16-22 gauge tube and the mandrel (e.g. 1) comprises an 18-35 gauge member, such as a conductive member. Optionally, the device comprises a delivery unit support comprising a handpiece.

Devices of the present invention are not limited to any particular size. For example, a device taught above, or any component thereof such as the mandrel, mandrel guide, and nozzle, or any dimension thereof (e.g. lateral or longitudinal dimension) is optionally scaled down to 1%-10%, such as 1% or 10% (e.g. for prenatal applications), or is optionally scaled up to 500%-1500% (for applications in large animals such as elephants). Also envisioned is a device scaled up or down (eg. 1%-10% or 500%-1500) in the lateral dimensions (e.g. to facilitate more or less bulky substances or for insertion into smaller or larger environments) but not substantially scaled in the longitudinal cross sections. Also envisioned is a device scaled down (eg. 1%-10% or 30%-60%) in the lateral dimensions (e.g. to facilitate entry into a vein or artery) but scaled up (e.g. 500%-1500%) in the longitudinal length (e.g. of the nozzle) to deliver or extract a substance to/from a target site that is remote from the insertion site In one embodiment, the delivery device has one or more (e.g any 1, 2, 3, 4, or 5) of the following features:
- (a) A substantial portion (e.g. entire) delivery device is designed for single-use and/or is disposable;
- (b) A substantial portion (e.g. entire) delivery device is be fabricated of materials suitable for sterilization by gamma irradiation;
- (c) The diameter of the delivery device assembly does not exceed 1 in, for example, less than about aby of: 0.8, 0.7 in, 0.6 in, or 0.5 in;
- (d) The length of the delivery device does not exceed 10 in, e.g. 9 in, 8, or 7.0 in. long, including the nozzle and mandrel assembly;
- (e) The implantation comprises luer lock In one embodiment, the delivery device comprises a handpiece having one or more (e.g any 1, 2, 3, 4, 5, or 6) of the following features:

- (a) designed for one-handed operation.
- (b) include a means for securing a nozzle and mandrel assembly in a nonpermanent manner;
- (c) include a means of locking the nozzle in the extended position to prevent inadvertent retraction such as a safety mechanism.
- (d) includes a release lever (e.g. toggle) for retracting the nozzle in a smooth, but incremental, manner as desired by the user.
- (e) the force required to actuate the nozzle retraction release lever does not exceed 3 lbs (e.g. less than about any of: 2 lbs, 1 lb, or ¾ lb, or about any of: 0.25 lb to 2 lb, 0.25 lb to 1 lb, or 0.25 lb to 0.75 lb; or about 200 g to about 500 g, or about 300 g).
- (f) includes an integral luer lock (e.g. female luer fitting), for example, at the proximal end for connection of a user-provided syringe, with or without tubing.

In one embodiment, the nozzle and mandrel have one or more (e.g any 1, 2, 3, 4, 5, or 6) of the following features:
- (a) are not integral to the hand piece; i.e. is removable from the hand piece without damage to either assembly;
- (b) are be fabricated of materials which are inert when exposed to human tissue.
- (c) accommodate tissue specimens up to 2.25 mm wide× 7.5 mm long×0.25 mm thick.

In one embodiment, the delivery device is a device for delivering ocular tissue such as RPE cells and comprises technical features of at least two (e.g. each of) of the three previous embodiments described above.

In one embodiment, the nozzle and mandrel are configured to accommodate any size and shape of nanoplate platform. For example, nanoplates can be configured in rectangular or disc shaped platforms.

In one embodiment, the nozzle and mandrel are configured to accommodate a nanoplate platform in the micro-sized range.

In one embodiment, the nozzle and mandrel are configured to accommodate a nanoplate platform in the macro-sized range.

In one embodiment, the nozzle and mandrel are configured to deliver nanoplates, sheets, and/or other substances, wherein the substance is less than 5 mm wide×14 mm long×2 mm thick, such as those which are less than 3.5 mm wide×11 mm long×0.5 mm thick, or less than 2.25 mm wide×7.5 mm long×0.25 mm thick.

In one embodiment, the device, including the nozzle, mandrel, delivery controller, and/or delivery unit support is configured to deliver fragile nanoplates, tissue, and/or cells without damaging the implant. For example, nanoplates can be provided as cell-loaded membranes which are designed for therapeutic use such as insertion into the sub-retinal space. With the teachings provided herein, the skilled artisan can now provide devices configured as such.

Examples of devices useful according to the present invention are those listed in Table 1.

As shown in Table 1, the present invention contemplates many different configurations of components taught herein.

TABLE 1

| Mode | Mandrel guide | Mandrel | Delivery controller | Operable Linkage |
| --- | --- | --- | --- | --- |
| Passive | 18 gauge tube with nozzle on distal end | 20 gauge conductive member forks into two 30 gauge conductive members laterally | Push button toggle; | Knife edge lock coupled to toggle; 15 gauge ratchet rack mounted on mandrel guide |

TABLE 1-continued

| Mode | Mandrel guide | Mandrel | Delivery controller | Operable Linkage |
|---|---|---|---|---|
| | | connected by one or more filler welds at the distal end. | | |
| Positive | 18 gauge tube with nozzle on distal end | 20 gauge conductive member forks into two 30 gauge conductive members laterally connected by one or more filler welds at the distal end. | Push button toggle; | Knife edge lock coupled to toggle; 15 gauge ratchet rack mounted on mandrel |
| Passive | 18 gauge tube with nozzle on distal end | 20 gauge conductive member forks into two 30 gauge conductive members laterally connected by one or more filler welds at the distal end. | Sliding Member | Locking screw locked through sliding member into a rack mounted on mandrel guide |
| Positive | 18 gauge tube with nozzle on distal end | 20 gauge conductive member forks into two 30 gauge conductive members laterally connected by one or more filler welds at the distal end. | Sliding Member | Locking screw locked through sliding member into a rack mounted on mandrel |
| | 18 gauge tube with nozzle on distal end | 20 gauge conductive member forks into two 30 gauge conductive members laterally connected by one or more filler welds at the distal end. | Push button toggle; | Traction pad coupled to toggle; 15 gauge ratchet rack mounted on mandrel guide |
| | non-cylindrical nozzle on distal end, optionally matched for delivering nanoplates | Two tubular conductive members laterally connected by one or more filler welds at the distal end, optionally curved to deliver retinal tissue, optionally further comprising fiber optic and/or diathermy cables | Sliding member or push-button or other member. | Configured such that release of finger pressure from delivery controller immediately halts longitudinal movement of the mandrel |
| Passive | 18 gauge tube with nozzle on distal end | 20 gauge conductive member forks into one or two 30 gauge conductive members laterally connected by one or more filler welds at the distal end. | Push button toggle; | Traction pad or other means for engaging the delivery unit |
| Positive | 18 gauge tube with nozzle on distal end | 20 gauge conductive member forks into one or two 30 gauge conductive members laterally connected by one or more filler welds at the distal end. | Push button toggle; | Traction pad or other means for engaging the delivery unit |

In one embodiment, the invention provides a device listed in Table 1, wherein at least one the delivery unit, mandrel, mandrel guide, nozzle, proximal length of guide, delivery controller, or delivery unit support is further modified in accordance with another embodiment taught herein. In another embodiment, the invention provides a device listed in Table 1, wherein at least one component selected from the delivery unit, mandrel, mandrel guide, nozzle, proximal length of guide, delivery controller, or delivery unit support is replaced with another component taught herein.

The devices taught herein are not limited to any particular configuration or device components and modifications which alternatively provide components having the same property or function are also contemplated. Accordingly, the invention provides an alternative embodiment in which a component that performs a specific function is replaced by a means for performing said function.

Utility

Devices of the present invention are useful for delivering or extracting a substance into/from an environment. Devices of the present invention are further useful for delivering or extracting a substance into/from an environment where the target site is blocked or partially blocked by a delicate environment and/or the substance intended for extraction or delivery is fragile.

Accordingly, one embodiment of the present invention provides a method for delivering a substance from device of the present invention into an environment, the method comprising loading a substance into the mandrel guide, orienting the open end of the mandrel guide at a target site in the environment, and retracting the mandrel guide relative to the mandrel to discharge the substance at the target site. Optionally, the method comprises inserting the mandrel guide into the environment. Optionally, retracting the mandrel guide comprises retracting both the nozzle and the proximal length of guide.

Optionally, the environment is an organism. Optionally, the organism is an animal, optionally a mammal, optionally a human or horse. Optionally, the mammal is a companion mammal, for example, a cat or dog. Optionally, the mammal is a laboratory mammal, for example, a mouse or a rat. Optionally, the environment is an organ, cavity, or joint. Optionally, the environment is an eye (e.g. the subretinal space of the eye).

Optionally, the substance is a tissue specimen, cellular specimen, an electronic chip, a drug, or a gel. Optionally, the tissue specimen is nervous, cardiac, vascular, bone, joint tissue, or the like, for example, radioactive seeding. Optionally, the nervous tissue is ocular tissue, for example, retinal tissue (e.g. fetal retinal tissue).

Optionally, the environment is an electronic device or a mechanical device, such as a circuit board, computer or computer component, automobile, medical implant (e.g. prosthetic tissue or organ).

Examples of such a substance are tissue specimens, gels, microchips, drugs, manufactured materials (e.g. supports) further comprising a drug or biological sample. Other substances include radioactive seeding.

Some delivery devices of the present invention provide a delivery device having a removable nozzle, wherein the nozzle is fully insertable into the environment, for example, insertable to the proximal length of guide. Optionally, the nozzle is substantially non-cylindrical (e.g. fit for nanoplates) and the proximal length of guide is cylindrical. Optionally, the environment is an eye. Accordingly, one embodiment provides a method of delivery a substance into an environment, the method comprising fully inserting the nozzle of a device having a removable nozzle into the environment before discharging the substance, wherein the insertion site is not substantially traumatized by said insertion.

Some delivery devices of the present invention provide a device having a conductive mandrel for performing a secondary activity. Accordingly, one embodiment of the present invention provides a method of delivering a substance into an environment, the method comprising placing the open end of the mandrel guide at the target site, discharging the substance, and performing a secondary activity with the delivery device before, during, or after said placing or said discharging. Optionally, the secondary activity comprises aspiration or infusion of a fluid at the target site. Optionally, the secondary activity comprises illumination visualizing the target site or environment. Optionally, the secondary activity comprises cauterization (e.g. diathermy or laser). Optionally, the secondary activity comprises infusion/aspiration, and one or more of cauterization and illumination.

Some delivery/extraction devices of the present invention provide a device having a removable or disposable quick-connect nozzle. Accordingly, one embodiment of the present invention provides a method of delivering a substance into an environment, the method comprising assembling the mandrel guide by fixing a nozzle to the proximal length of guide, placing the open end of the mandrel guide at the target site, and discharging the substance. Optionally, the step of fixing a nozzle to the proximal length of guide comprises placing the nozzle on or at the proximal length of guide and locking the nozzle to the proximal length of guide by at least one of jaws and a sliding nozzle lock. Alternatively, the step of fixing a nozzle to the proximal length of guide optionally comprises placing a nozzle on inner grippiers (e.g. rigid and/or serrated inner grippers). Optionally, the substance is ocular tissue, such as retinal tissue (e.g. a nanoplate comprising retinal tissue or stem cells).

Some delivery/extraction devices of the present invention provide a device having a delivery controller operable with reduced force (e.g. less than about 3 lbs), perpendicular force (e.g. less than about 3 lbs, such as less than about any of: 2 lbs, 1 lb, or ¾ lb, or about any of: 0.25 lb to 2 lb, 0.25 lb to 1 lb, or 0.25 lb to 0.75 lb, or about 200 g to about 500 g, or about 300 g), and/or perpendicular motion (e.g. less than about 4 mm) relative to the angle of the length of mandrel guide that protrudes from the insertion site. Such devices reduce tissue trauma, for example, by allowing the user to keep the device absolutely still. Accordingly, one embodiment of the present invention provides a method for delivery a substance from a device of the present invention, the method comprising, the method comprising loading a substance into the mandrel guide, inserting the mandrel guide into an environment, and operating the delivery controller to discharge the substance by imparting a perpendicular motion on the delivery controller of less than 4, 3, 2, or 1 mm, relative to the angle length of mandrel guide that protrudes from the insertion site.

Device configurations of the present invention are especially useful for ocular surgery because target site is blocked or partially blocked by a delicate environment and the substance intended for extraction or delivery is often fragile. Accordingly, one embodiment of the present invention provides a method for delivering a substance (e.g. retinal tissue, for example a sheet of retinal tissue or a nanoplate comprising retinal tissue or stem cells) from a device of the present invention to a target site in an ocular environment (e.g. subretinal space), the method comprising loading a substance into the mandrel guide, inserting the mandrel guide into an eye, orienting the open end of the mandrel guide at a target site in the eye, and moving the mandrel through the mandrel guide towards the open end to discharge the substance at the target site. Optionally, the target site is the subretinal space of the eye. Optionally, the substance is a tissue specimen such as retinal tissue (e.g. fetal retinal tissue). Optionally, the method comprises making an incision in the eye before inserting the mandrel guide through the incision. Optionally, the method comprises inserting the mandrel guide through the pars plana in the region of the ciliary body at the periphery of the retina. Optionally, the method comprises incising the retina near the diseased target site giving access to the subretinal space. Optionally, the delivery device comprises a removable nozzle and the method comprises fully inserting the nozzle into the eye before discharging the substance, wherein the insertion site is not substantially traumatized by said insertion. Optionally, moving the mandrel through the mandrel guide towards the open end to discharge the substance at the target site comprises operating a delivery controller which comprises a sliding member or ratchet, as taught herein.

EXAMPLES

Example 1

Device with Delivery Controller Linked Internally

One embodiment of the present invention provides a device for delivering a substance, as depicted in FIG. 1. The device comprises a delivery unit 5 comprising a mandrel guide (e.g. 2) and a mandrel 1 disposed internally of the mandrel guide (e.g. 2). The delivery unit is supported by a delivery unit support 4. A delivery controller 3 is operably linked (operable linkage not shown) to the delivery unit 5 in the lumen 7 of the delivery unit support 4 to control longitudinal movement of the mandrel 1 relative to the mandrel guide (e.g. 2).

Surprisingly, such a configuration provides for easier maneuverability in the presence of other devices such as scopes and less obstruction of vision, for example, thereby reducing tissue trauma during a procedure. Such a configuration reduces bulk in comparison to prior art devices in which the delivery controller is linked, for example, directly to the nozzle externally of the mandrel guide. Surprisingly, prior art devices with external linkage are very awkward and dangerous to manipulate around other devices such as scopes.

Example 2

Device with Fully Insertable Nozzle

Figure 2:
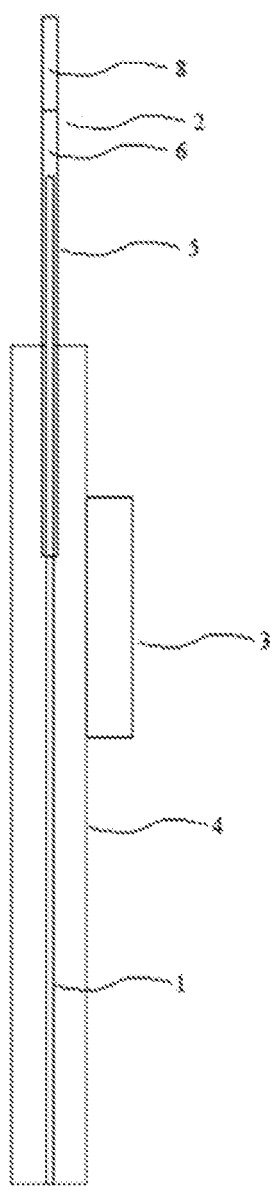
FIG. 2 depicts a schematic representative of a device of a device the present invention, showing only the relative longitudinal orientation of the mandrel, mandrel guide, and the distal end of the delivery unit support, and the relative longitudinal orientation of the nozzle and proximal length of guide.

One embodiment of the present invention provides a device for delivering a substance, as depicted in FIG. 2. The device comprises a delivery unit 5 comprising a mandrel guide (e.g. 2) and a mandrel 1 disposed internally of the mandrel guide (e.g. 2). The mandrel guide (e.g. 2) comprises a proximal length of guide 6 supported by a delivery unit support 4. The mandrel guide (e.g. 2) also comprises a nozzle 8 that is longitudinally fixed relative to the proximal length of guide 6. A delivery controller 3 is operably linked (operable linkage not shown) to the delivery unit 5 through a component other than the nozzle 8 (e.g. proximal to the nozzle such as linked to the mandrel 1 or proximal length of guide 6) to control longitudinal movement of the mandrel 1 relative to the mandrel guide (e.g. 2). Such a configuration allows the nozzle 8 to be fully inserted in tissue when the delivery unit 5 is in position for delivery such that the nozzle does not protrude from the site of insertion (e.g. the eye for delivery of retinal tissue to the subretinal space). This is especially advantageous when using curved and/or non-cylindrical nozzles in combination with a cylindrical proximal length of guide such that the cylindrical portion extends through the insertion site rather than the nozzle which would otherwise traumatize the insertion site when rotated, as is often required in order to place the distal end of a curved nozzle at the target site.

Example 3

Device with Conductive Mandrel

One embodiment of the present invention provides a device for delivering a substance, as depicted in FIG. 3a. The device comprises a delivery unit 5 comprising a mandrel guide (e.g. 2) and a mandrel 1 disposed internally of the mandrel guide (e.g. 2). The delivery unit is supported by a delivery unit support 4. A delivery controller 3 is operably linked (operably linkage not shown) to the delivery unit 5 to control longitudinal movement of the mandrel 1 relative to the mandrel guide (e.g. 2). The mandrel 1 interfaces with the substance intended for delivery (not shown) at the distal end 9 of the mandrel 1. The mandrel further comprises least one conductive member, such as a tubular member 10 to conduct gas, liquid, or other substances such as fiber optic fibers. As depicted in FIG. 3b, optionally, the mandrel 1 comprises a plurality of tubular members 10 and/or a filler weld 11 to increase the surface area of the interface between the distal end 9 of the mandrel 1 and the substance intended for delivery (not shown).

In addition to delivery and/or extraction, a device having such a configuration performs additional functions that were previously performed by separate devices, thereby lessening tissue trauma by reducing the total device volume inserted into the patient and facilitating a simplified medical procedure using only a single device.

Example 4

Conductive Mandrel

An example of a conductive mandrel of the present invention is shown in FIG. 5a. A magnified view of the far most distal portion of the mandrel 1 is shown in FIG. 5b and an exploded view is shown in FIG. 5c. The mandrel 1 is constructed from a proximal elongated tubular conductive member 30 that conductively forks 32 into two distal tubular conductive members 31 that form the distal end 9 of the mandrel 1. The distal end of the mandrel 9 interfaces with the substance to be delivered or extracted (not shown) at a filler weld 11 that lateral connects the distal ends of the tubular conductive members 31. The proximal tubular conductive member 30 is conductively linked 32 to the distal end of the mandrel 9, which is in turn conductively linked (not shown) to an external device (not shown) to allow gas, liquid, fiber optics, and the like to be transmitted between the target delivery site and the external device through the mandrel 1 (not shown).

The mandrel can optionally be made from a metal, for example, stainless steel such as 304 stainless steel, or other inert material (i.e. inert to biological tissue and/or pharmaceutically acceptable material) such as inert polymers.

The tubular conductive members can optionally be made from SS hypodermic tubing such as TW 304 SS hypodermic tubing.

The tubular conductive members 31 at distal end 9 of the mandrel can optionally be made from hypodermic tubing (e.g. TW 304 SS hypodermic tubing) or other inert tubing and/or sized for delivering substances to the eye, for example, using 30 gauge tubing.

The proximal elongated tubular conductive member 30 can optionally be made from hypodermic tubing (e.g. TW 304 SS hypodermic tubing) or other inert tubing and/or sized for delivering substances such as 20 gauge tubing for delivering substances to the eye.

Although FIG. 5b depicts conductive members 31 merging into a single proximal elongated tubular conductive member 31, conductive mandrels are not limited to such a configuration. For example, the conductive members 31 alternatively extend throughout the length of the device and are operably linked to the same secondary device or different secondary devices. In addition, although FIG. 5b depicts distinct members 31 that fork at the distal end, the invention also encompasses configurations wherein the distal end is made from only a single conductive member that is flared to distribute the port across the interface of a substance to be delivered.

The filler weld can optionally be made from metal or other inert material, for example, from 304 stainless steel.

Figure 14:
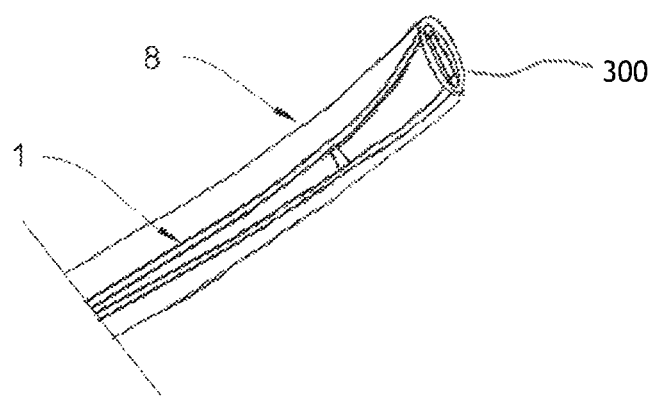
FIGS. 14 and 15 depict mandrel configurations for conductive mandrels and for non-cylindrical nozzles of the present invention.
Figure 15:
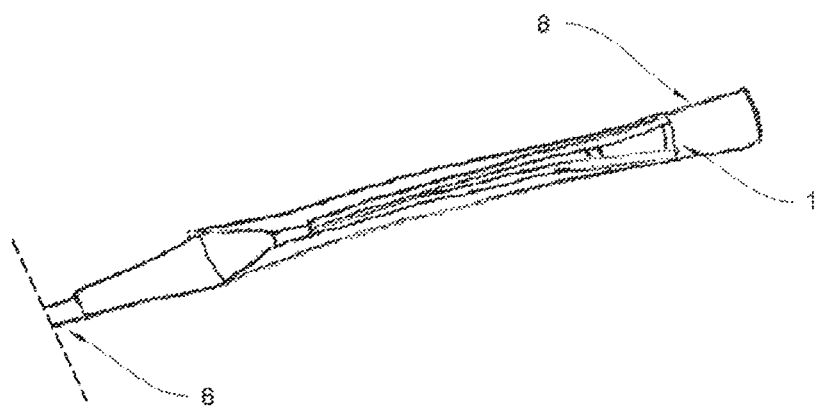

FIGS. 14 and 15 illustrate non limiting examples of conductive mandrels inside a nozzle.

Such a mandrel performs additional functions that were previously performed by separate devices, yet effectively performs the function of a mandrel and/or extraction (i.e. to bias the substance for discharge upon movement through the mandrel guide) by interfacing the substance at the filler weld 11. The forked configuration of such a mandrel is especially well suited for substances in the form of a sheet, for example, retinal tissue or a nanoplate (e.g. comprising stem cells or retinal tissue for implantation into the eye).

Surprisingly, infusion/aspiration conductive members are optionally configured to eliminate the need for external venting of the instrument during delivery. Further surprising is that infusion/aspiration conductive members are optionally used to load a substance into the device with gentle suction, which is significantly less damaging to delicate substances such as RPE cells and/or sheets and nanoplates.

Example 5

Conductive Mandrel

Figure 11A:
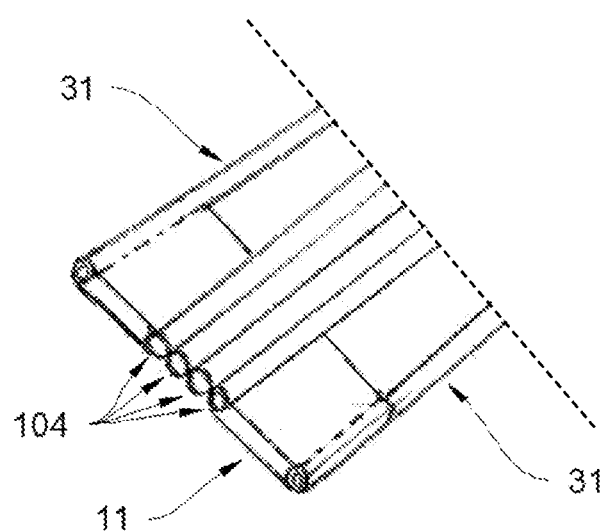
FIG. 11 depicts examplary configurations for devices of the present invention with conductive mandrels.

A conductive mandrel is provided, as in Example 4. More specifically, the mandrel comprises one or more tubular conductive members for aspiration/infusion, and additionally comprises one or more additional conductive members for light (e.g. fiber optic cables) and/or conductive members for cauterization (e.g. diathermy cables or a laser). An example of such a conductive mandrel is depicted in FIG. 11a. Examples of devices comprising such a conductive mandrel are depicted in FIGS. 11b, 11c, and 11d.

FIG. 11a depicts a specific example of a mandrel comprising tubular conductive members 31 for aspiration/infusion (e.g. linked in paralleled to a fluid pump) and further comprising conductive members 104 for light and/or cauterization, for example, positioned between the tubular conductive members or elsewhere. Although FIG. 11a depicts four conductive members, such a conductive mandrel is not limited thereto. Collectively, the conductive members 104 can optionally include any of the following:
 a. fiber optic cables e.g. all fiber optic cables);
 b. diathermy cables;
 c. a mixture of fiber optic cables and diathermy cables (e.g. two fiber optic cables and two diathermy cables);
 d. a mixture of at least one laser fiber and one or more fiber optic cables; and
 e. arthroscope or camera.

Figure 11B:
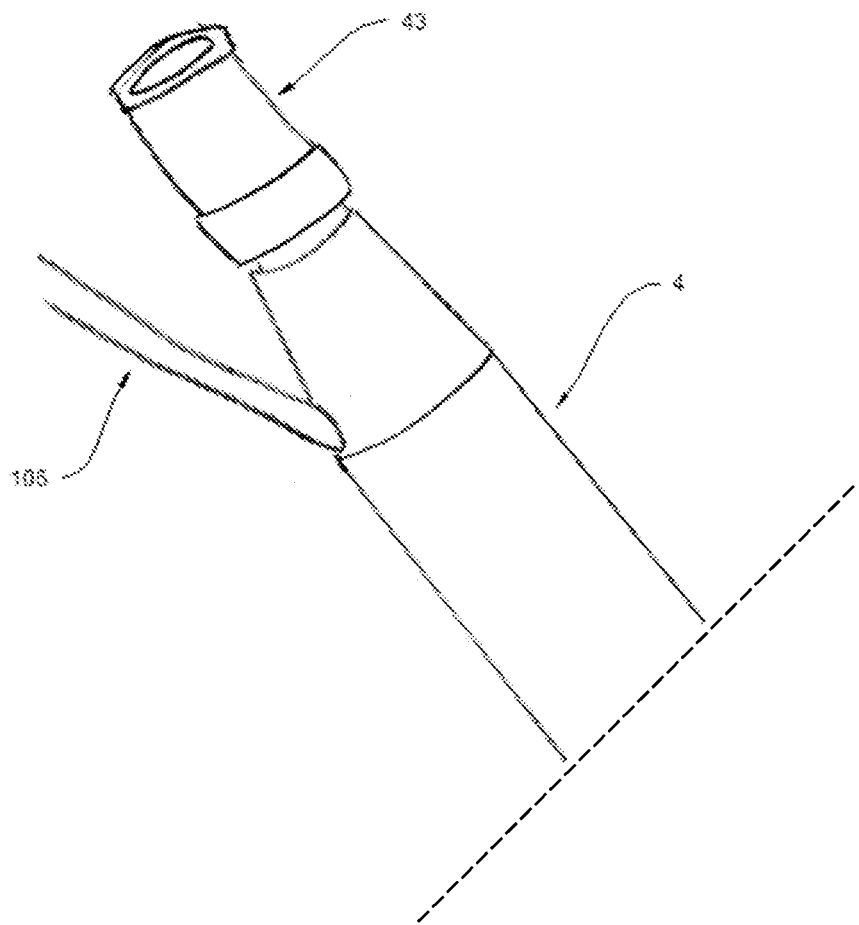

FIGS. 11b, 11c, and 11d depict optional configurations for operably linking conductive members 31 and 104 to secondary devices. For example, conductive members 31 can optionally be operably linked to a fluid pump (e.g. syringe 105) using a Luer lock 43 (or other pump coupling means such as an insution/aspiration tube 109). Conductive members 104 can optionally be operably linked through operably linkage 106 to one or more secondary devices. For example, banana plugs 107 (or other diathermy coupling means) can optionally be provided for operably linked diathermy cables and/or a fiber optic coupler 109 can optionally be provided to operably link fiber optic cables to a light source.

FIG. 11c illustrates the illumination that can optionally be provided by the fiber optic cables of a conductive mandrel. As can be seen in FIG. 11c, the cables can optionally be configured to illuminate the target site at the distal end of the nozzle, and/or illuminate any of: the nozzle itself and a substance loaded therein when a translucent or transparent nozzle is used.

In addition to the superior properties discussed in Example 4, the incorporation of fiber optic cables surprisingly allows illumination and/or visualization of the tip of the nozzle under the target site (e.g. retina) to provide far more accurate placement of substance to reduce trauma. In addition, the fiber optic cables allow better visualization during loading to ensure loading of the substance (e.g. RPE cells and/or nanoplates) in the proper orientation of the substance in the nozzle, and to ensure proper position within the nozzle during a procedure. The nozzle can optionally be provided as a translucent or transparent nozzle, for example, to enhance such surprising properties.

Additionally or alternatively, the use of diathermy cables is surprisingly effective in stopping bleeding, for example, at the edge of the retinotomy during in-vivo use.

Example 6

Mandrel Guide with Quick-Connect Nozzle

An example of a mandrel guide of the present invention is shown in FIG. 6. The mandrel guide (e.g. 2) is constructed from a removable or disposable nozzle 8, a proximal length of guide 6, and a sliding nozzle lock 33. Opposing jaws 35 fixed to and extending from the first member proximal length of guide 6 are biased in the open position by flat springs 38, as shown in FIG. 6b. The nozzle 8 is placed between the jaws 35 such that a pair tooth holes 41 align with the respective jaw teeth 37. Once the nozzle 8 is in position for the tooth holes 41 to accept the respective jaw teeth 37, the sliding nozzle lock 35 is slid from the position shown in FIG. 6b towards the distal end. As it slides, the sliding nozzle lock 35 forces the pair of jaws 35 to close on the nozzle 8 and insert the jaw teeth 37 into the tooth holes 41. A pin 39, also fixed to and extending from the proximal length of guide 6 is biased outwardly towards the pin hole 34 of the sliding lock 35 by a flat spring 40. The mandrel guide (e.g. 2) is fully assembled when the pin 39 is inserted into the pin hole 34 of the sliding nozzle lock 35, as shown in FIG. 6a.

The nozzle is optionally non-cylindrical (e.g. shaped to fit nanoplates), for example, as shown in FIGS. 14-16. The nozzle is optionally made from a biocompatible polymer with a wall thickness of approximately 0.005 inch to 0.006 inch, and optionally transparent and flexible (e.g. made from fluorinated ethylene propylene). Further, the nozzle is optionally disposable.

Such a configuration not only provides ease of entry into and exit from the eye, but also facilitates rapid yet sturdy on-site assembly of the mandrel guide. In addition, this configuration provide a minimally evasive, low profile coupler which is optionally inserted through an insertion site (e.g. the eye).

As an alternative to the jawed configuration illustrated in FIG. 6, the proximal length of guide 6 is optionally provided with inner gripping members to grip a nozzle slid thereover, as illustrated in FIG. 13. The gripping members are optionally serrated to provide additional grip. This also provides a minimally evasive, low profile coupler which is optionally inserted through an insertion site (e.g. the eye).

Example 7

Device with Passive Action Sliding Delivery Controller

FIG. 4 depicts one embodiment of the invention. The device comprises a delivery unit 5 comprising a mandrel guide (e.g. 2), as described in Example 6, and a mandrel 1, as described in Example 4 disposed internally of the mandrel guide (e.g. 2). A delivery unit support 4 comprises a tubular housing and is provided with a distal endcap 24 having a port 25 for longitudinal acceptance but latitudinal or radial support of the mandrel guide (e.g. 2) to allow the mandrel guide (e.g. 2) to slide longitudinally through the endcap port 25 with little or no latitudinal or radial movement of the mandrel guide (e.g. 2) at the endcap 24. The endcap 24 is fit to the delivery unit support 4 by an endcap lip 26 for sliding fit into the delivery support 4.

The proximal end of the mandrel 1 is fixed to the delivery unit support 4 in a Luer lock 27, which is itself fixed to the distal end of the delivery unit support 4 by a locking screw 28. The Luer lock 27 is optionally connected to an external device through a Luer housing of the external device (not shown).

The delivery controller 3 comprises a sliding member 11 disposed externally of the delivery unit support 4. The delivery controller 3 is operably linked to the delivery unit 5 by fixing sliding member 11 to the mandrel guide (e.g. 2). The sliding member 11 is fixed to the mandrel guide (e.g. 2) by a locking screw 13 inserted through the sliding member 11 and screw locked into a rack 12 mounted on the proximal length of guide 6 and having a threaded hole 29 for acceptance and locking of the locking screw 13. In such a configuration, sliding member 11 longitudinally towards the proximal end of the device causes the mandrel guide (e.g. 2) to also slide longitudinally over the mandrel 1 towards the proximal end of the device until the substance to be delivered is ejected from the nozzle 8 of the mandrel guide (e.g. 2).

Surprisingly, such a configuration provides a high precision device that is readily maneuverable, smooth delivery of delicate tissue, and simple to use.

Such a configuration allows the device to be operated with little or no force or motion perpendicular to the mandrel guide at the insertion site, thereby reducing trauma to the patient.

Surprisingly, such a configuration provides high precision device that is capable of easy maneuverability, smooth delivery of delicate tissue, and simple to use to provide more accurate placement of the substance (e.g. beneath the retina) and less trauma to the target site (e.g. retina) and its environment.

Example 8

Device with Positive Action Sliding Delivery Controller

FIG. 7 depicts one embodiment of the invention. The device comprises a delivery unit 5 comprising a mandrel guide (e.g. 2), as described in Example 6, and a mandrel 1, as described in Example 4, disposed internally of the mandrel guide (e.g. 2). A delivery unit support 4 comprises a tubular housing and is provided with a distal endcap 24 having a port 25 for longitudinal acceptance but latitudinal or radial support of the mandrel guide (e.g. 2). The endcap 24 is fit to the delivery unit support 4 by an endcap lip 26 for sliding fit into the delivery support 4. The mandrel guide (e.g. 2) is fixed to delivery unit support 4 by a locking screw (not shown) screwed through the endcap 24 and locked onto the proximal length of guide 6.

The proximal end of the mandrel 1 is not fixed to delivery unit support 4, but is inserted in a Luer lock 27, which slides longitudinally through the proximal end of the delivery unit 4. The Luer lock 27 is optionally connected to an external device through a Luer housing of the external device (not shown).

The delivery controller 3 comprises a sliding member 11 disposed externally of the delivery unit support 4. The delivery controller 3 is operably linked to the delivery unit 5 by fixing sliding member 11 to the mandrel 1. The sliding member 11 is fixed to the mandrel 1 by a locking screw 13 inserted through the sliding member 11 and screw locked into a rack 42 mounted on the mandrel 1 and having a threaded hole 29 for acceptance and locking of the locking screw 13. In such a configuration, sliding member 11 longitudinally towards the proximal end of the device causes the mandrel guide 1 to also slide longitudinally through the mandrel guide (e.g. 2) towards the distal end of the device until the substance to be delivered or extracted is ejected from the nozzle 8 of the mandrel guide (e.g. 2).

Surprisingly, such a configuration provides high precision devices that are readily maneuverable, can smoothly deliver delicate tissue, and are simple to use to provide more accurate placement of the substance (e.g. beneath the retina) with less trauma to the target site (e.g. retina) and its environment.

Such a configuration allows the device to be operated with little or no force or motion perpendicular to the mandrel guide at the insertion site, thereby reducing trauma to the patient.

Example 9

Device with Positive Action Push-Button Control

FIG. 8 depicts one embodiment of the invention. The device comprises a delivery unit 5 comprising a mandrel guide (e.g. 2), as described in Example 6, and a mandrel 1, as described in Example 4, disposed internally of the mandrel guide (e.g. 2). A delivery unit support 4 comprises a tubular housing and is provided with a distal endcap 24 having a port 25 for longitudinal acceptance but latitudinal or radial support of the mandrel guide (e.g. 2). The endcap 24 is fit to the delivery unit support 4 by an endcap lip 26 for sliding fit into the delivery support 4. The mandrel guide (e.g. 2) is fixed to delivery unit support 4 by a locking screw 36 screwed through the endcap 24 and locked onto the proximal length of guide 6.

The proximal end of the mandrel 1 is not fixed to the delivery unit support 4, but is inserted in a Luer housing 43, which slides longitudinally through the proximal end of the delivery unit 4. The Luer housing 43 is optionally connected to an external device through a Luer lock of the external device (not shown).

The delivery controller 3 comprises a toggle (e.g. 14) disposed externally of the delivery unit support 4. The toggle (e.g. 14) is operably linked to the delivery unit 5 through a knife edge lock 15 that engages/disengages teeth 16 of a rack 44 mounted on the mandrel 1.

In the loaded position, the mandrel 1 is forcibly biased towards the distal end for delivery by a tension spring 17 such that a tooth 16 of the rack 44 contacts the knife edge lock 15, thereby locking the mandrel 1 with respect to its longitudinal position. The knife edge lock 15 of the toggle (e.g. 14) is forcibly biased into a tooth 16 of the rack 44 by a flat spring 45 of the delivery controller 3 mounted to delivery unit support 4 by a pair of locking screws 47. Activation of the toggle (e.g. 14) disengages the knife edge lock 15 from the teeth 16, thereby allowing distal longitudinal movement of the mandrel 1 due to the biasing force of the tension spring 17.

The tension spring 17 is housed by a pair of bushings 19, 20. Bushing 19 is secured to the mandrel 1 by locking screw 21 but remains unsecured to the delivery unit support 4 to allow advancement of the mandrel 1 upon disengagement of the knife edge lock 15 from the teeth 16. Bushing 20 is secured to the delivery unit support 4 by locking screws 47 to resist expansion of tension spring 17 while the mandrel 1 is retracted to the loaded position, but is unsecured from the mandrel 1 to allow longitudinal movement of the mandrel 1 relative to bushing 20 and delivery unit support 4. Because the locking screw 21 reversibly secures the bushing 19 to the mandrel 1, the tension, delivery speed, and loaded position of the mandrel 1 are optionally adjusted by changing the longitudinal position that bushing 19 is secured to the mandrel 1.

Surprisingly, such a configuration provides a high precision device that is capable of easy maneuverability, smooth delivery of delicate tissue, and simple to use to provide more accurate placement of the substance (e.g. beneath the retina) and less trauma to the target site (e.g. retina) and its environment.

Such a configuration allows the device to be operated with little or no force or motion perpendicular to the mandrel guide at the insertion site, thereby reducing trauma to the patient.

An adjustable rate of delivery speed controlled by an internal coaxial spring and an delivery unit engaging means (e.g. ratcheting system) allows superior delivery of delicate tissue, which is optionally protected in the nozzle to be placed in the subretinal space without damage to the tissue or retina.

Example 10

Device with Passive Action Push-Button Control

FIG. 9 depicts one embodiment of the invention. The device comprises a delivery unit 5 comprising a mandrel guide (e.g. 2), as described in Example 6, and a mandrel 1, as described in Example 4, disposed internally of the mandrel guide (e.g. 2). A delivery unit support 4 comprises a tubular housing and is provided with a distal endcap 24 having a port 25 (e.g. shoe fit for the proximal length of guide 6) for longitudinal acceptance but latitudinal or radial support of the mandrel guide (e.g. 2) to allow the mandrel guide (e.g. 2) to slide longitudinally through the endcap port 25 with little or no latitudinal or radial movement of the mandrel guide (e.g. 2) at the endcap 24. The endcap 24 is fit to the delivery unit support 4 by an endcap lip 26 for sliding fit into the delivery support 4.

The proximal end of the mandrel 1 is fixed to the delivery unit support 4 in a Luer housing 43, which is itself fixed to the distal end of the delivery unit support 4 by a locking screw 28. The Luer housing 43 is optionally connected to an external device through a Luer lock of the external device (not shown).

The delivery controller 3 comprises a toggle (e.g. 14) disposed externally of the delivery unit support 4. The toggle (e.g. 14) is operably linked to the delivery unit 5 through a knife edge lock 46 that engages/disengages teeth 49 of a rack 48 mounted on the proximal length of guide 6.

In the loaded position, the proximal length of guide 6 is forcibly biased towards the proximal end for delivery by a tension spring 17 such that a tooth 49 of the rack 48 contacts the knife edge lock 46, thereby locking the mandrel guide (e.g. 2) with respect to its longitudinal position. The knife edge lock 46 of the toggle (e.g. 14) is forcibly biased into a tooth 49 of the rack 48 by a flat spring 45 of the delivery controller 3 mounted to delivery unit support 4 by a pair of locking screws 47. Activation of the toggle (e.g. 14) disengages the knife edge lock 46 from the teeth 49, thereby allowing proximal longitudinal movement of the mandrel guide (e.g. 2) due to the biasing force of the tension spring 17.

The tension spring 17 is housed by a pair of bushings 50, 51. Bushing 50 is secured to the proximal length of guide 6 by set screws but remains unsecured to the delivery unit support 4 to allow retraction of the mandrel guide (e.g. 2) upon disengagement of the knife edge lock 46 from the teeth 49. Bushing 51 is secured to the delivery unit support 4 by locking screw 52 to resist expansion of tension spring 17 while the mandrel guide (e.g. 2) is advanced to the loaded position. Because the locking screw 52 reversibly secures the bushing 51 to the mandrel delivery unit support 4, the tension and delivery (retraction) speed of the mandrel guide (e.g. 2) are optionally adjusted by changing the longitudinal position that bushing 51 is secured to the delivery unit 4.

Surprisingly, such a configuration results in a high precision device that is readily maneuverable, can smoothly deliver delicate tissue, and is simple to use to provide more accurate placement of the substance (e.g. beneath the retina) with less trauma to the target site (e.g. retina) and its environment.

Such a configuration allows the device to be operated with little or no force or motion perpendicular to the mandrel guide at the insertion site, thereby reducing trauma to the patient. Such a configuration is also advantageous because it provides regulated delivery, and immediate stoppage on release of finger pressure.

An adjustable rate of delivery speed controlled by an internal coaxial spring and a delivery unit engaging means (e.g. ratcheting system) allows superior delivery of delicate tissue, which may be protected in the nozzle to be placed in the subretinal space without damage to the tissue or retina.

The device is optionally provided with an 18 gauge proximal length of guide 6, optionally provided with a 15 gauge rack 48 in order to, for example, deliver RPE cells under the retina.

Example 11

Preparation of an Implant

An implant was prepared to be delivered using a device of the present invention. Although any method of preparing a substance may be used, the following method was used to prepare RPE cells.

RPE cells were harvested as sheets using dispase as described previously [Tezel T H, Del Priore L V, Kaplan H J. Harvest and storage of adult human retinal pigment epithelial sheets. Current eye research 1997; 16:802-809]. In brief, following removal of the sclera, eyes were treated with 2% dispase for 40 minutes at 37 degrees C. Dispase-treated eyes were washed in DMEM and an incision was made into the subretinal space. RPE sheets were isolated, gently placed on Transwell membrane insert [Corning Life Sciences, Wilkes Barre, Pa.], and were cultured in growth media consisting of DMEM supplemented 10% FBS, 100 IU/ml penicillin, and 100 g/ml streptomycin. Monolayer cell sheets were harvested one week later for retinal implantation.

Example 12

Precise Delivery with Reduced Trauma

Various devices of the present invention were used to deliver a substance to a target site. Although any device configurations taught herein may be used for delivery, we selected for this example devices having sliding member or push-button delivery controllers of the present invention, conductive mandrels of the present invention with infusion/aspiration (30 gauge tubes) and fiber optics, and flexible, transparent nozzles (e.g. made from fluorinated ethylene propylene) for delivering RPE cells which had been prepared by the method set forth in Example 11. The porcine RPE cells on the Transwell membrane were cut to pieces 2 millimeters by 5 millimeters and placed in a fluid in a petri dish for loading into the nozzle.

The lighted nozzle allowed superior visualization of the orientation of the pig RPE cells on the membrane, so it could be loaded correctly with RPE cells on top of the membrane, and so its position in the nozzle could easily be seen. For animal and human, neural retina together with the RPE was provided on top of a nanoplate. The device was especially useful because it provided for placement with proper orientation which is important for integration and synaptic connection to occur between the host and the transplant.

Figure 12:
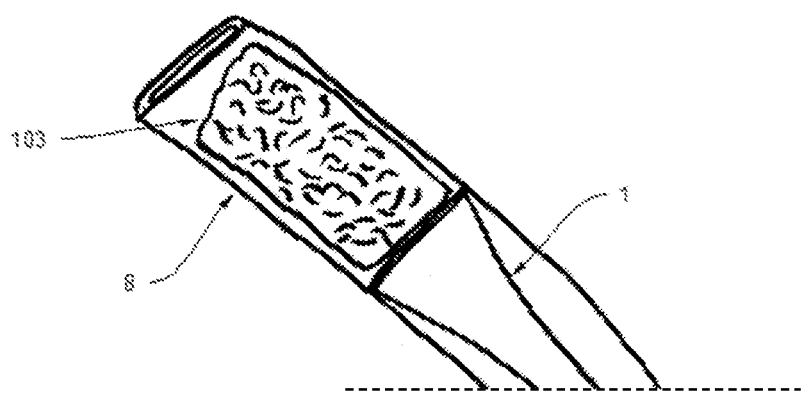
FIG. 12 depicts a transparent nozzle of the present invention with a substance loaded therein.

The suction on the instrument allowed loading of the tissue into the instrument with no damage to the tissue because of the very controlled gentle infusion/aspiration conductive members. Visualization of the transplant (porcine RPE cells on the Transwell membrane) 103 in the nozzle 8 was excellent, after loading and prior to transplantation into the human cadaver eye both because of the clear plastic nozzle 8, as seen in FIG. 12, and the fiber optic cables which illuminate the nozzle and target site. In addition, the size and ergonomics of the instrument was very conducive to easy maneuverability.

The tip was readily introduced through the scleral opening in the human cadaver eye. Retraction of the nozzle 8 relative 1 to the mandrel allowed the delicate monolayer stem cells carried on the nanoplate to be delivered gently out of the open end of the nozzle into the target area under the retina. Surprisingly, delivery of the nanoplate using the push-button or the push-pull controller allowed precise placement of the tissue beneath the retina and minimal trauma to the retina with a complete preservation of the RPE cells on the Transwell membrane observed after it had been placed under the retina. Even more surprisingly, the use of infusion/aspiration mandrels during delivery further enhanced these properties of the instruments. This eliminated any need for external venting of the instrument. Further, the instrument prevented subretinal bleeding because of the ease with which it was able to maneuver subretinally.

The 30-gauge tube that formed the ports that perform the aspiration/infusion function was extremely efficient and its location was at a most critical position of the instrument, i.e. at the distal end of the mandrel, behind the loaded substance. The fiber optic light at the distal end of the mandrel allowed for visualization of the tissue under the retina when placing the transplant beneath the retina of the cadaver eye. In addition to this, the light provided very good illumination of the porcine RPE Transwell membrane in the loading stage, and in the fluid in the petri dish, to assure proper orientation of the RPE cells transplantation.

The distal end of the mandrel in the nozzle was matched to fit the nozzle such that movement was done smoothly without binding yet providing a leak-free tip.

The health and viability of the RPE cells prior to transplantation were maintained after transplantation in the cadaver eye as documented by microscopic histopathology after the subretinal placement.

These data on the cell growth and instrument performance for transplantation of porcine RPE cells (e.g. on a Transwell membrane and/or nanoplate and the like) into the subretinal space of a human cadaver eye demonstrates examples of superior properties of devices taught herein.

Example 13

Nozzle Coupler with Gripping Members

Figure 17A:
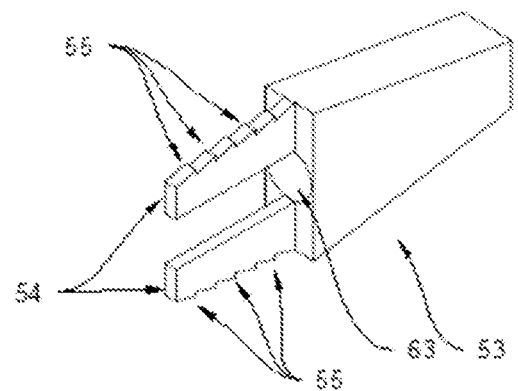
FIG. 17 depicts a reversible nozzle coupler of the present invention.
Figure 17B:
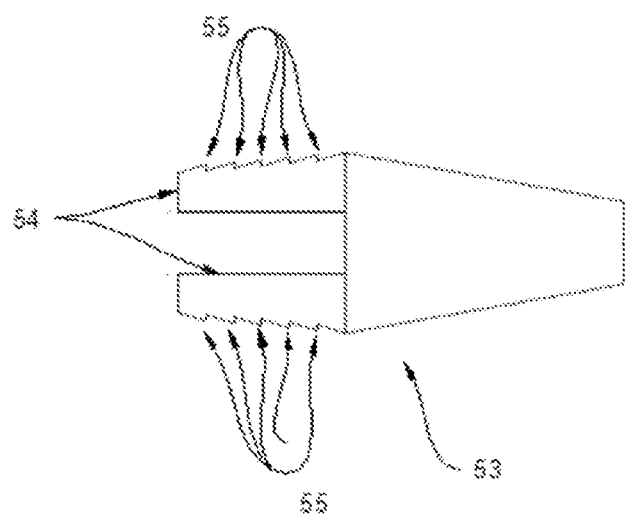

An example of a nozzle coupler for a mandrel guide is shown in FIG. 17a and FIG. 17b. The nozzle coupler 53 comprises gripping members 54 to grip a nozzle slid there over, for example, to grip the nozzle shown in FIG. 16. The gripping members 54 optionally comprise serrations 55, or other traction-imparting means (e.g. adhesive, rubber, grit or other non-slip coating), to provide additional grip. The nozzle coupler 53 comprises a port 63 to allow passage of a mandrel there through.

The nozzle is made from stainless steel, for example.

Surprisingly, a nozzle coupler with gripping members is optionally configured to provide a minimally evasive, low profile coupling means which is optionally inserted through an insertion site (e.g. the eye).

Such a configuration can not only be configured to provide ease of entry into and exit from the eye, but also to facilitate rapid yet sturdy on-site assembly of the mandrel guide.

Example 14

Conductive Mandrel

Figure 18A:
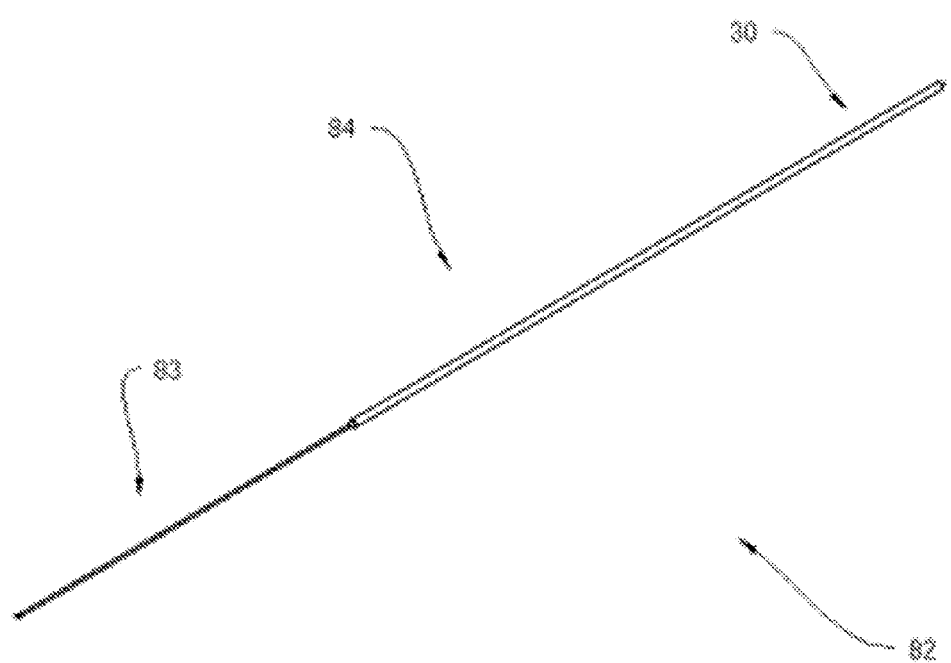
FIG. 18 depicts a conductive mandrel of the present invention.

An example of a conductive mandrel 84 of the present invention is shown in FIG. 18a, A magnified view of the distal portion 83 of the mandrel 84 is shown in FIG. 18b. The mandrel 84 is constructed from a proximal elongated tubular (cannular) conductive member 30 connected to, and optionally tapers down to, a distal tubular conductive member 83. Although proximal member 30 and distal member 83 is optionally constructed as a single, non-tapered tubular member (cannula), the smaller diameter (or other cross-section) provided by the taper optionally allows the use of a smaller nozzle, thereby reducing trauma at the site of entry, while retaining strength at the proximal member 30. Additionally, or alternatively, the tapered configuration optionally provides enhanced flexibility using a smaller diameter distal tubular conductive member 83 and/or aids infusion/suction, for example, for loading of a substance.

As depicted in FIGS. 18b and 18c, a cannula 89 connects the distal end 88 and the proximal end 90, to conductively link the distal end 99 to the proximal member 30, which can itself be conductively linked (not shown) to the users choice of secondary device (not shown) to allow gas, liquid, fiber optics, and/or others to be transmitted between the target delivery site and the external device through the mandrel 84 (not shown).

As depicted in FIGS. 18b and 18c, the distal end 88 is optionally flared, for example, in order to provide increase the surface area at the interface of the substance to be delivered (e.g. nanoplate) or extracted (not shown) and a means of manipulation (e.g. hydraulic pressure, suction, or other biasing force).

Figure 19A:
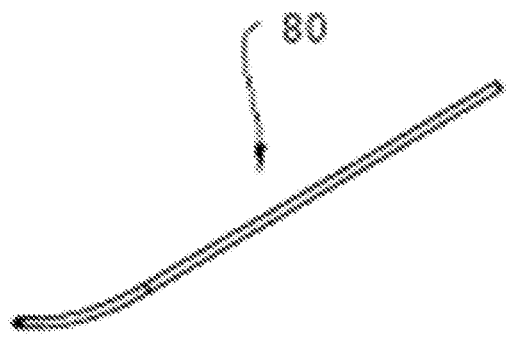
FIG. 19 depicts a nozzle of the present invention.
Figure 19B:
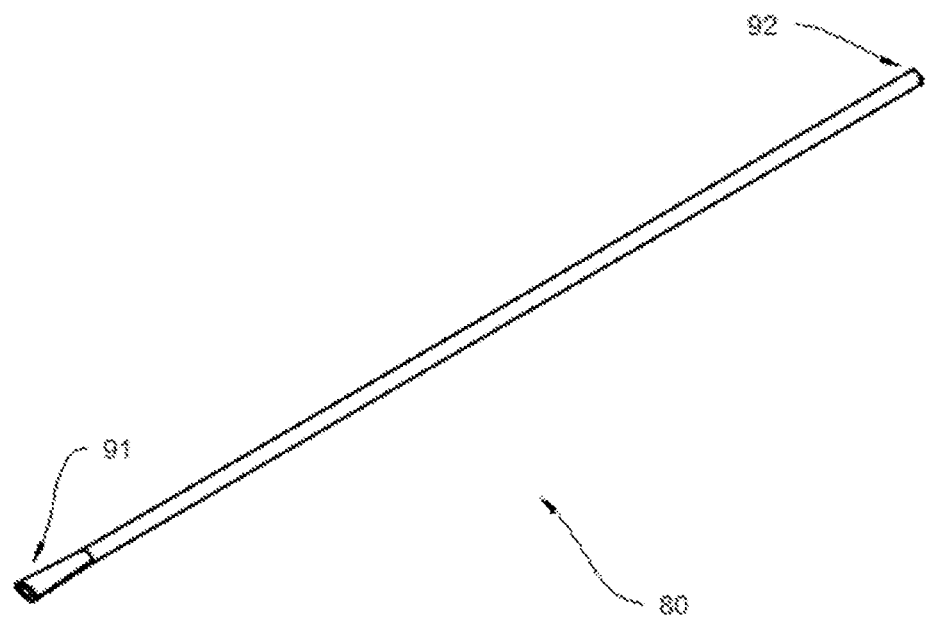

In one embodiment, the mandrel 84 is combined with the nozzle 80 depicted in FIG. 19*a* and the magnified view of FIG. 19*b*. The distal tip 91 of nozzle 80 is sized is flared similarly but slightly larger than the distal end 88 to provide a matched-fit.

Such a mandrel can optionally be configured and used to perform additional functions that were previously performed by separate devices, yet effectively performs the function of a mandrel and/or extraction (i.e. to bias the substance for discharge upon movement through the mandrel guide). The oblate- or elliptical-like flare is especially well suited for substances in the form of a sheet, for example, retinal tissue or a nanoplate (e.g. comprising stem cells or retinal tissue for implantation into the eye).

Further, such a conductive mandrel can optionally be combined with a transparent nozzle.

Surprisingly, infusion/aspiration conductive members mandrel can optionally be configured eliminate the need for external venting of the instrument during delivery. Further surprising is that infusion/aspiration conductive members are optionally used to load a substance into the device with gentle suction, which is significantly less damaging to delicate substances such as RPE cells and/or sheets and nanoplates.

Example 15

Modular Mandrel Guide

Figure 20A:
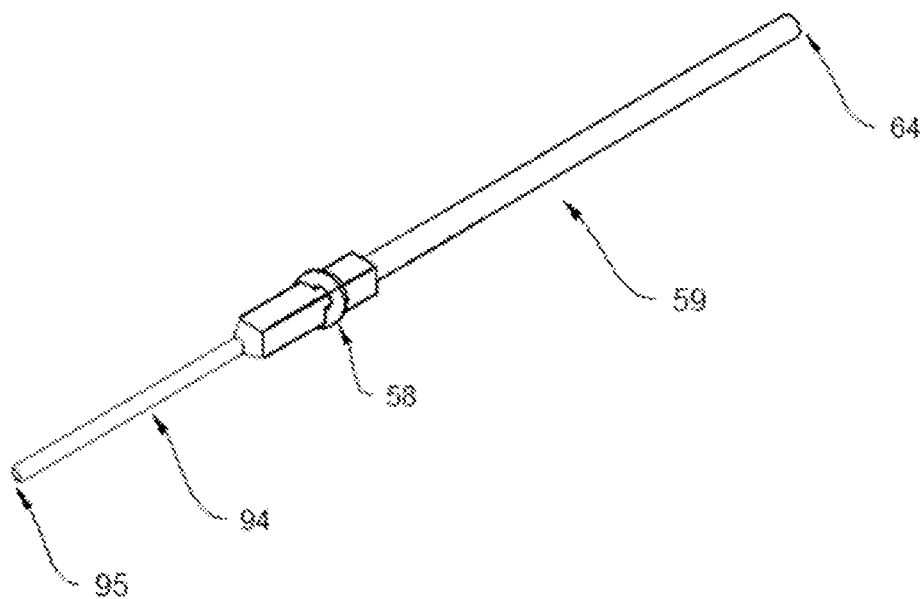
FIG. 20 depicts reversibly coupled members of a modular mandrel guide of the present invention.
Figure 20B:
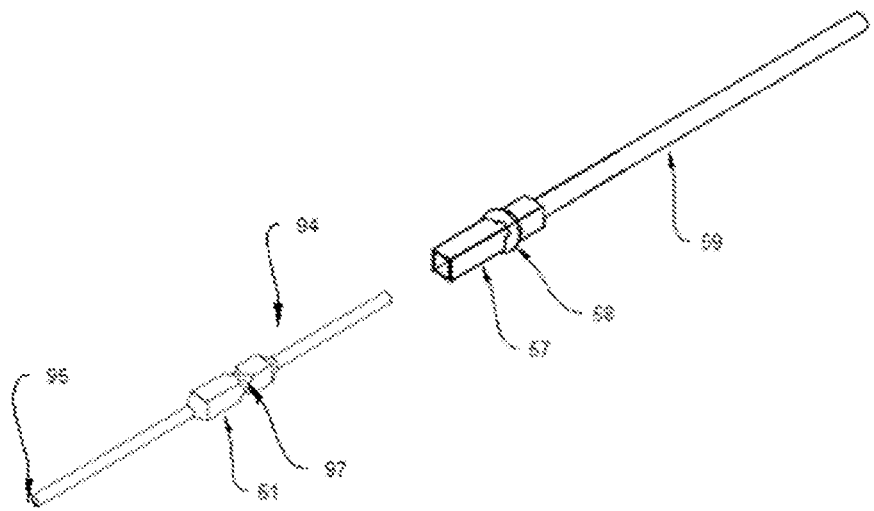

FIG. 20*a* and FIG. 20*b* depict a modular mandrel guide or modular proximal length of guide ('modular mandrel guide') of the present invention. As with any mandrel guide or proximal length of guide taught herein, the modular mandrel guide comprises a guide for a mandrel, for example, a cannula extending from port 95 at the distal end to the proximal end 64. The modular mandrel guide is comprised of two members disposed longitudinally and reversibly coupled to each other by a key/keyway coupler. As depicted in FIG. 20*a* and FIG. 20*b*, the nozzle holder 95 comprises a key 61 configured to engage a keyway 57 of base 59.

In the non-limiting example illustrated in FIG. 20*a* and FIG. 20*b*, the corners of the keyway 57 are partially cutaway to allow o-ring 58 to protrude partially inside the keyway 57, and the keyway 57 is a match-fit for the key 61 such that the key 61 "snaps" into place when grooves 97 formed in key 61 align with O-ring 58. With this configuration, the o-ring 58 optionally helps to support the mandrel guide when placed in a handpiece or other delivery unit support, and optionally imparts "rolling" action about the handpiece to reduce friction in a passive-action setup (where the mandrel guide moves about the hand piece.

The nozzle holder is made from, for example, from stainless steel hypodermic tubing such as 18 gauge stainless steel hypodermic tubing for delivering substances to the eye.

The base 59 is made from, for example, stainless steel, for example, 13 gauge 304 ss hypodermic tubing for delivering substances to the eye.

The key way 57 is made from, for example, brass seamless telescoping tubing, for example, 3/32" brass seamless telescoping tubing, for delivering substances to the eye.

The modular mandrel guide allows, for example, the alternative use of a plurality of nozzles, each associated with a different nozzle holder 95. For example, nozzle holder 81 (FIG. 20*c*) is optionally coupled to nozzle 80 (FIG. 19*a*), for use with mandrel 82 (FIG. 18*a*), as illustrated in FIG. 22*a* and FIG. 22*b*. Similarly, nozzle holder 60 (FIG. 20*d*) is optionally coupled to nozzle 86 (FIG. 16), for use with the mandrel of FIG. 5*a*, as illustrated in FIG. 21*a* and FIG. 21*b*.

Example 16

Traction Pad Delivery Controller

FIG. 10 depicts a useful delivery controller in a section view of a delivery device of the present invention. The delivery controller is of the toggle type, comprising a toggle (e.g. 14) disposed about the delivery unit support 4 and operably linked to the delivery unit 5 (e.g the mandrel guide of the delivery unit) through a traction pad 96 as a delivery unit engagement means.

Figure 23A:
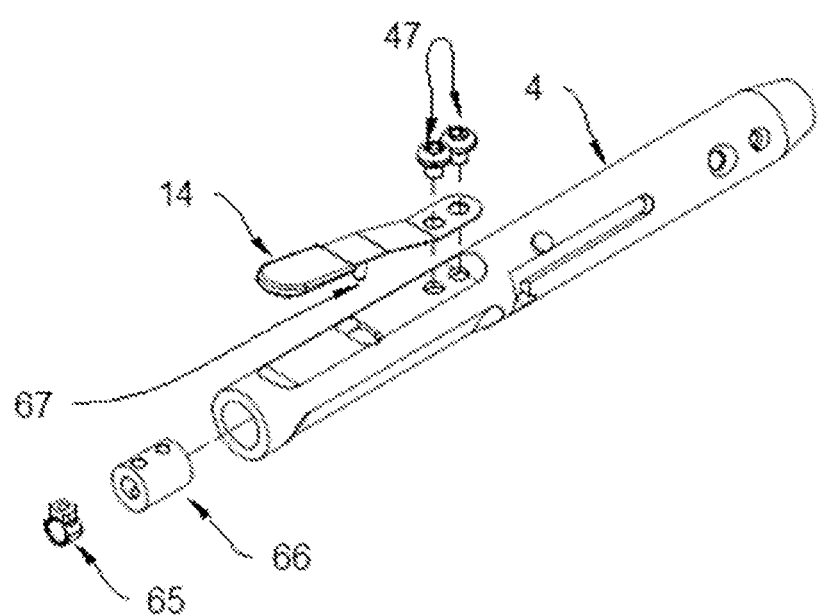
FIG. 23 depicts a delivery controller with delivery unit engagement means of the present invention.

In the loaded position, delivery unit 5 is biased for delivery (e.g. a mandrel guide positioned distally but biased towards the proximal end), for example, by a first spring (delivery unit biasing means not shown). The traction pad 96 is biased to engage and inhibit movement of the delivery unit 5 by a delivery controller biasing means (construction of delivery controller biasing means is not illustrated), for example, by a second spring attached the toggle (e.g. 14) (e.g. the toggle (e.g. 14) is optionally attached to or constructed as a flat spring, as illustrated in FIG. 23*a*). The user can operate the delivery controller by pushing on the toggle (e.g. 14), thereby disengaging traction pad 96 from delivery unit 5 to allow the delivery unit biasing member to induce movement of the delivery unit and delivery of a loaded substance.

Surprisingly, this delivery controller provides a high precision device that is readily maneuverable, can smoothly deliver delicate tissue, and is simple to use to provide more accurate placement of the substance (e.g. beneath the retina) with less trauma to the target site (e.g. retina) and its environment.

Such a configuration allows the device to be operated with lithe or no force or motion perpendicular to the mandrel guide at the insertion site, thereby reducing trauma to the patient. Such a configuration is also advantageous because it provides regulated delivery, and immediate stoppage on release of finger pressure.

The delivery controller is optionally configured to require less than about 3 lbs. (e.g. less than about any of: 2 lbs, 1 lb, or ¾ lb, or about any of: 0.25 lb to 2 lb, 0.25 lb to 1 lb, or 0.25 lb to 0.75 lb, or about 200 g to about 500 g, or about 300 g) to disengage traction pad 96 from delivery unit 5 and allow movement of the delivery unit 5, for example, by configuring the force of delivery controller biasing means (e.g. flat spring).

Example 17

Traction Pad Delivery Controller

Figure 23B:
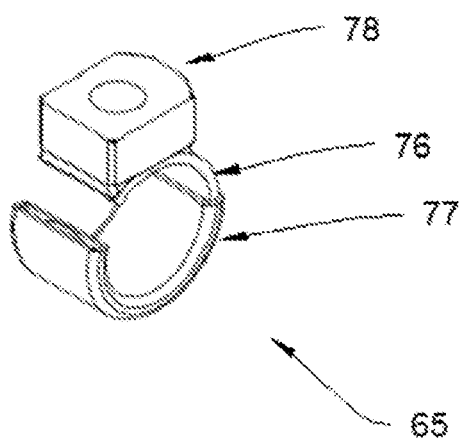

FIG. 23*a* and FIG. 23*b* depict a useful delivery controller according to the present invention. The delivery controller is an embodiment of that illustrated in FIG. 10 and detailed in Example 16. More specifically, the delivery controller is of the toggle type, comprising a toggle (e.g. 14) (depicted as flat spring-based lever) disposed about the delivery unit support 4 (depicted as a handpiece).

The delivery unit engagement means is a traction pad 65 comprising a hook 76 (or other configuration) with frictional surface 77. By way of example, the toggle (e.g. 14) is attached to the traction pad 65 by inserting the traction pad into the delivery unit support 4 and threading nut 78 onto screw 67 of the toggle (e.g. 14).

The toggle (e.g. 14) is mounted to the delivery unit support 4, for example, by inserting a toggle-mount 66 into the delivery unit 4 such that it aligns with the toggle (e.g. 14) and screwing screws 47 into female threaded holes ('tapped holes') of toggle-mount 66. The non-limiting example of the toggle-mount 66 depicted in FIG. 23a comprise cannula to allow passage of a delivery unit member such as base 59 of a mandrel guide, as depicted in FIG. 23c.

Figure 23C:
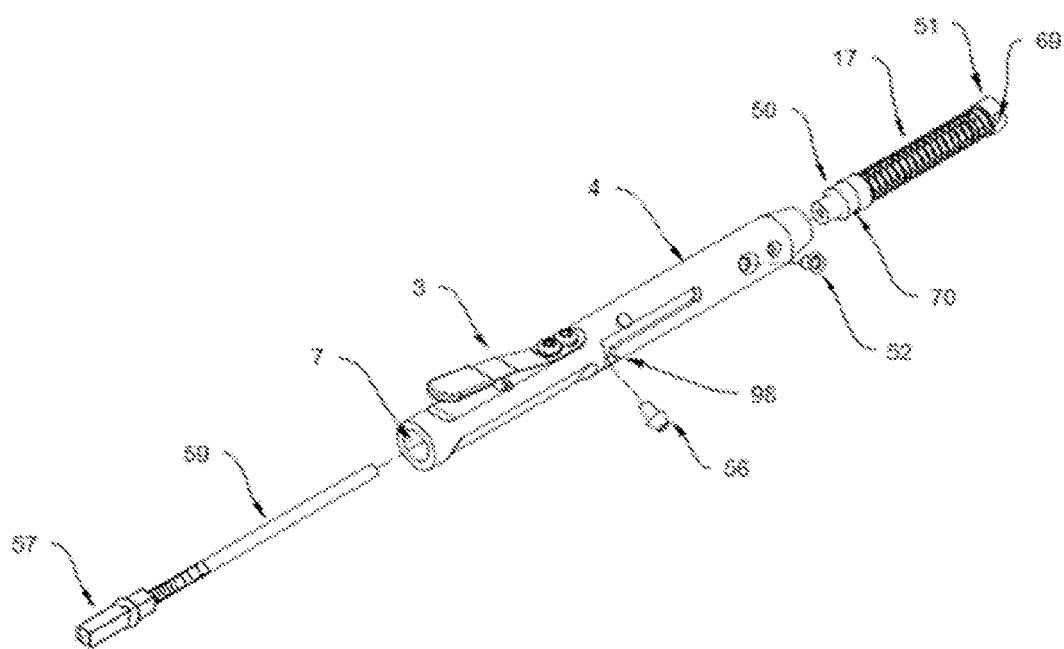

The delivery unit is optionally combined with any delivery unit member such as a proximal length of mandrel guide, for example, a mandrel guide base 59, as depicted in FIG. 23c. Using the mandrel guide base 59 as specific example of a delivery unit member, the base 59 is linked to a biasing means such as spring 17 by inserting the proximal end of base 59 into movable bushing 50, screwing screw 56 into threaded hole 70 to join 59 and spring bushing 50. Fixed bushing 51 is secured to the delivery unit support 4 by screwing screw 52 into threaded hole 69. In the loaded position, mandrel guide base 59 is positioned in the forward position (distally) but biased towards the rear by spring 17. Toggle (e.g. 14) (depicted as a flat spring type lever) biases traction pad 65 to engage and inhibit movement of mandrel guide base 59. The user can operate the delivery controller by pushing on the toggle (e.g. 14), thereby disengaging traction pad 65 mandrel guide base 59 to allow spring 17 to induce rearward movement of the mandrel guide and ejection (delivery) of a loaded substance when the device is fully assembled with a mandrel (see, for example, FIG. 24).

Screw 56 (or other set-pin) optionally provides a means of setting the delivery unit to the loaded position by moving it screw 56 forward (distally) while the traction pad 65 is disengaged from the delivery unit. As depicted in FIG. 23c, the delivery device is optionally configured with a safety mechanism, for example, by providing a safety latch 98 on delivery unit support 4. The user can move screw 56 (or other set-pin) into safety latch 98 to lock the delivery unit in the loaded position to prevent inadvertent movement.

The hook 76 is made from, for example, hypodermic tubing (e.g. 9 gauge tw).

The frictional surface 77 is made from, for example, silicon tubing 9 (e.g. medical) such as tubing with 0.065" o.d.× 0.030" i.d.

Figure 23D:
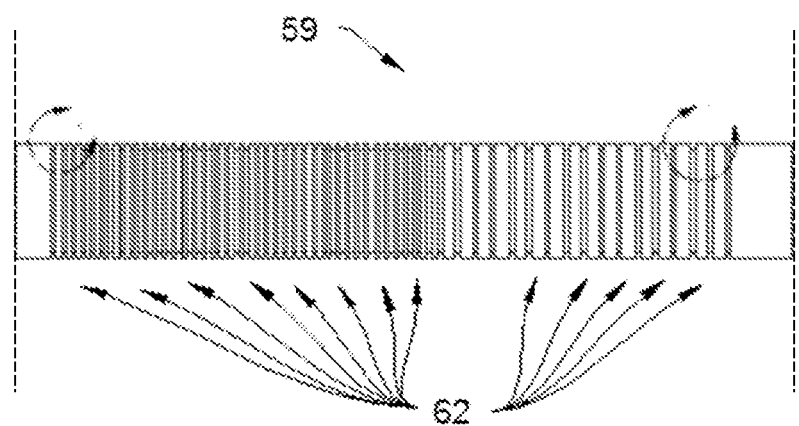

The delivery unit member (depicted as mandrel guide base 59) optionally comprises a frictional surface 62 to aid in braking (i.e. inhibiting movement) when the traction pad engages the delivery unit member. The frictional surface 62 is optionally provided, for example, as a textured surface such as a plurality of grooves in the delivery unit member, as illustrated in FIG. 23d. Optionally, the plurality of grooves or other texture are spaced tighter at the distal portion than at the proximal portion, and/or are tapered from the distal end to the proximal end, for example, to provide a smoother departure of the mandrel.

Surprisingly, this delivery controller of the traction pad type provides a high precision device that is readily maneuverable, can smoothly deliver delicate tissue, and is simple to use to provide more accurate placement of the substance (e.g. beneath the retina) with less trauma to the target site (e.g. retina) and its environment.

Such a configuration allows the device to be operated with little or no force or motion perpendicular to the mandrel guide at the insertion site, thereby reducing trauma to the patient. Such a configuration is also advantageous because it provides regulated delivery, and immediate stoppage on release of finger pressure.

Toggle (e.g. 14) is optionally configured to require less than about 3 lbs. (e.g. less than about any of: 2 lbs, 1 lb, or ¾ lb, or about any of: 025 lb to 2 lb, 0.25 lb to 1 lb, or 0.25 lb to 0.75 lb, or about 200 g to about 500 g, or about 300 g) to disengage traction pad 65 from delivery unit (e.g. mandrel guide base 59), for example, by configuring the force of delivery controller biasing means (e.g. flat spring type lever).

Example 18

Delivery Device with Modular Mandrel Guide and Conductive Mandrel

One embodiment of the present invention provides a delivery device comprising a modular mandrel guide, for example, as described in Example 15 and a conductive mandrel, for example, as described in Example 4 or Example 14. The delivery unit support comprises an interface such as a Luer lock for conductively linking the conductive mandrel to a fluid pump. The coupler of the modular mandrel guide is optionally provided as a key/keyway coupler such that the base of the modular mandrel guide is optionally assembled with interchangeable nozzle holders and their respective nozzles and mandrels. For example, a delivery device is optionally provided as depicted in FIG. 24 with keyway 57 such that either of the nozzle holders (and their respective mandrels) depicted in FIG. 24 or FIG. 22b can used (FIG. 25 depicts a fully assembled delivery device). Accordingly, the delivery device can also be provided in a kit comprising the modular mandrel guide base and one or more sets, wherein each set comprises a mandrel and its respective nozzle (e.g. a nozzle which is size matched for the mandrel) and nozzle holder. If a plurality of sets are provided, each set is optionally different or the same. As an alternative to the kit or full device, a partial delivery device is provided comprising the delivery unit support, delivery controller, and modular mandrel guide, i.e. the delivery device without the mandrel, nozzle, and/or nozzle holder. Although the delivery device is optionally provided as a disposable device, the user can then use a single partial delivery device with his choice of the mandrel, nozzle, and/or nozzle holder.

Figure 26:
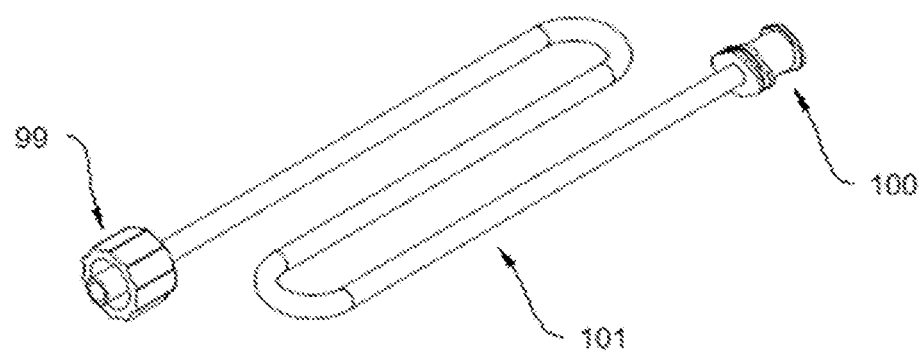
FIG. 26 depicts a conductive mandrel interface of the present invention.
Figure 27A:
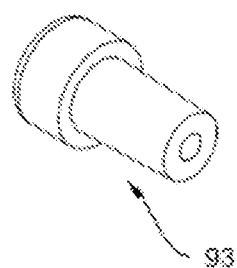
FIG. 27 depicts a back seal/plug.
Figure 27B:
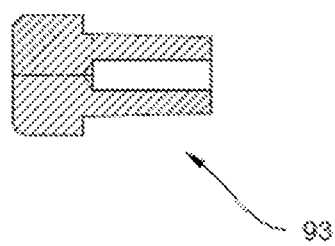

In one embodiment, the delivery device, kit, or partial delivery device is provided with a Luer lock (Luer fitting) and tubing 100 comprising Luer fittings 99, 100 on each end, as depicted in FIG. 26. Additionally, or alternatively, the delivery device, kit, or partial delivery device comprises a plug or seal 93.

In either embodiment, the delivery device, kit, or partial delivery device is delivery of a substance into an eye (e.g. into the subretinal space), for example, delivery of retinal tissue and/or nanoplates.

Example 19

Optional Configurations

A device is provided as in any of the previous examples and configured for delivering therapeutic substances such as retinal tissue and/or nanoplates into a subject (e.g. into the eye such as into the subretinal space). More specifically, the device is configured to any of the following specifications:
 a) Is fabricated from components which are suitable for sterilization by gamma radiation, for example, the mandrel, the mandrel guide, the nozzle, the proximal length of guide, the delivery unit support, or the entire device are fabricated from materials suitable for sterilization by gamma radiation (e.g. using stainless steel or gamma-compatible polymers);

b) the size of the device does not exceed about: 1 inches diameter×12 inches in longitudinal length, optionally wherein the diameter does not exceed about 0.5 inches, optionally, optionally wherein the longitudinal length does not exceed about 7 inches;
c) the device is configured for one-handed operation;
d) the delivery controller is configured for longitudinal movement of the mandrel relative to the mandrel guide in a smooth and incremental, manner as desired by the user;
e) the nozzle and mandrel are configured to be removed from the delivery unit support without damage to either the nozzle or mandrel, respectively;
f) the nozzle and mandrel assembly are fabricated of materials which are inert when exposed to human tissue;
g) the device comprises a transparent nozzle;
h) the nozzle and mandrel are configured to accommodate tissue specimens up to 3.5 mm wide×11 mm long×0.5 mm thick or up to 2.25 mm wide×7.5 mm long×0.25 mm thick;
i) a and b;
j) a and c;
k) a and d;
l) a and e;
m) a and f;
n) a, b, and c;
o) a, b, and d;
p) a, b, c, and d;
q) a e, and f;
r) a, b, and g;
s) a, c, and g;
t) a, d, and g;
u) a, e, and g;
v) a, f, and g;
w) a, b, and g c;
x) a, b, d, and g;
y) a, b, c, d, and g;
z) a, e, f, and g;
aa) a and g;
bb) g and c;
cc) g and d;
dd) g and e;
ee) g and f;
ff) a, g, and h;
gg) a and h;
hh) g and h;
ii) a and b;
jj) h, a and c;
kk) h, a and d;
ll) h, a and a;
mm) h, a and f;
nn) h, a, b, and c;
oo) h, a, b, and d;
pp) h, a, b, c, and d;
qq) h, a e, and f;
rr) h, a, b, and g;
ss) h, a, c, and g;
tt) h, a, d, and g;
uu) h, a, a, and g;
vv) h, a, f, and g;
ww) h, a, b, and g c;
xx) h, a, b, d, and g;
yy) h, a, b, c, d, and g;
zz) h, a, e, f, and g;
aaa) h, a and g;
bbb) h, g and c;
ccc) h, g and d;
ddd) h, g and e; or
eee) h, g and f.

The citations provided herein are hereby incorporated by reference for the cited subject matter.

We claim:
1. A device for implanting a substance comprising:
(a) a delivery unit comprising:
  (i) a mandrel guide, wherein the mandrel guide has an open distal end suitable for discharging a substance when loaded therein; and
  (ii) a longitudinally elongated mandrel disposed internally to the mandrel guide, whereby relative longitudinal movement of the mandrel through the mandrel guide towards the open distal end biases the loaded substance to move longitudinally towards the open end;
(b) a delivery unit support providing support to the delivery unit, wherein at least one of the mandrel and the mandrel guide is not fixed to the delivery unit support to allow longitudinal movement there about;
(c) a delivery unit biasing member imparting a force on the delivery unit to bias the delivery unit for the relative longitudinal movement;
(d) a delivery unit engagement means for opposing said force on the delivery unit, wherein
  (i) when the delivery unit engagement means can be engaged and disengaged with the delivery unit;
  (ii) when the delivery unit engagement means is engaged with the delivery unit, the delivery unit engagement means opposes said force on the delivery unit, thereby preventing the relative longitudinal movement of the delivery unit; and
  (iii) when the delivery unit engagement means is disengaged with the delivery unit, the delivery unit engagement means does not prevent the relative longitudinal movement of the delivery unit; and
(e) a delivery controller configured to engage and disengage the delivery unit engagement means from the delivery unit,
wherein:
the mandrel can move longitudinally relative to the mandrel guide from a first longitudinal position to a second longitudinal position and to plurality of longitudinal positions intermediate of the first longitudinal position and the second longitudinal position;
the delivery controller is configured for operation by a user's operating member such that:
engagement of the user's operating member with the delivery controller disengages the delivery unit engagement means from the delivery unit; and
disengagement of the user's operating member from the delivery controller engages the delivery unit engagement means with the delivery unit, thereby stopping the relative longitudinal movement; and
the delivery unit engagement means is configured to engage and disengage the delivery unit when the mandrel is at each of the plurality of longitudinal positions relative to the mandrel guide, whereby the delivery unit engagement means can be controlled by the delivery controller to start and stop the relative longitudinal movement when the mandrel is at each of the plurality of longitudinal positions relative to the mandrel guide.

2. The device of claim 1, wherein the longitudinally elongated mandrel is a conductive mandrel comprising:
(a) a distal end and at least a first distal port positioned at the distal end;

(b) at least a first proximal port positioned proximal to the at least first distal port; and
(c) a conductive member linking the at least first distal port and the at least first proximal port, wherein the conductive member is configured to conduct one or more of a fluid and a wave between the at least first distal port and the at least first proximal port.

3. The device of claim 2, wherein the conductive member comprises:
  (a) a fluid-conducting tube;
  (b) an electrically conductive wire;
  (c) a wave-transmitter;
  (d) a fiber optic cable;
  (e) a combination of a fluid-conducting tube and an electrically conductive wire;
  (f) a combination of a fluid-conducting tube and a wave-transmitter or a combination of a fluid-conducting tube and a fiber optic cable; or
  (g) a combination of a fluid-conducting tube, an electrically conductive wire, and a wave-transmitter or a combination of a fluid-conducting tube, an electrically conductive wire, and a fiber optic cable.

4. The device of claim 2, wherein the distal end of the conductive mandrel comprises a plurality of fluid-conducting tubes disposed laterally of each other and a surface area-increasing member that increases the lateral surface area of the conductive mandrel.

5. The device of claim 1, wherein the delivery controller comprises a toggle configured to interface a finger of a user thereof.

6. The device of claim 1 wherein the delivery controller comprises a biasing member for biasing the delivery unit engagement means to engage the delivery unit when the delivery unit engagement means is disengaged with the delivery unit; whereby applying a user force to the delivery controller disengages the delivery unit engagement means from the delivery unit to allow the relative longitudinal movement.

7. The device claim 3, wherein the delivery controller comprises a toggle configured to interface a finger of a user thereof.

8. The device of claim 4, wherein disengagement of the delivery unit engagement means requires less than about 3 lbs of force on the delivery controller from the user, optionally, wherein said less than about 3 lbs of force is:
  less than about 2 lbs of force, less than about 1 lb of force, or less than ¾ lb of force; or
  about any of 0.25 lb to 2 lb, 0.25 lb to 1 lb, or 0.25 lb to 0.75 lb; and about 200 g to about 500 g of force.

9. The device of claim 5, further comprising a safety switch configured to be in an engaged state and a disengaged state, wherein the user can operate the safety switch to change the state of the safety switch, wherein:
  when in the engaged state, the safety switch opposes the force of the delivery unit basing member, thereby preventing said relative longitudinal movement of the delivery unit irrespective of whether the delivery unit engagement means is engaged; and
  when in the disengaged state, the safety switch does not oppose the bias of the delivery unit basing means, thereby allowing said relative longitudinal movement of the delivery unit when the delivery unit engagement means is disengaged from the delivery unit.

10. The device of claim 9, wherein the delivery controller comprises an engagement biasing means for biasing the delivery unit engagement means to engage the delivery unit; whereby applying a user force to the delivery controller disengages delivery unit engagement means from the delivery unit to allow the relative longitudinal movement.

11. The device of claim 6, wherein the safety switch comprises:
  a pin fixed to the delivery unit and configured to move along a longitudinal path with the delivery unit, and
  a latch disposed laterally of said longitudinal path, wherein the pin is configured to be movable into the latch, and thereby becomes longitudinally immobilized, wherein said relative longitudinal movement is prevented when the pin is longitudinally immobilized.

12. The device of claim 1, wherein:
  the delivery unit engagement means comprises a traction pad wherein said opposing said force on the delivery unit comprises opposing said force on the delivery unit with a friction force; or
  the delivery unit engagement means comprises a knife edge lock, the delivery unit comprises a ratchet rack comprising a plurality of ratchet teeth, and the engagement of the delivery unit engagement means with the delivery unit comprises engagement of the knife edge lock with a ratchet tooth of the ratchet rack.

13. The device of claim 1, wherein at least a distal portion of at least of one of the elongated mandrel and the mandrel guide are flexible or curved.

14. The device of claim 13, wherein said distal portion is flexible or curved enough to slide under the retina into the subretinal space when inserted through the pars plana of the eye.

15. The device of claim 1, wherein the mandrel guide comprises a proximal length of guide and a nozzle coupled thereto, wherein the proximal length of guide comprises:
  a modular mandrel guide base; and
  a nozzle holder, wherein:
    the modular mandrel guide base and the nozzle holder are coupled to each other such that the modular mandrel guide base and the nozzle holder can be connected to each other and disconnected from each other; and
    the nozzle holder is coupled to a nozzle.

16. The device of claim 1, wherein the mandrel guide comprises a transparent nozzle.

17. The device of claim 1, wherein:
  a) the mandrel guide comprises a nozzle at a distal end of the mandrel guide;
  b) the delivery controller is operably linked to the delivery unit at a location proximal of the nozzle; and
  c) the delivery controller is operably linked to the delivery unit inside the delivery unit support.

18. A device for implanting a substance comprising:
  (a) a delivery unit comprising:
    (i) a mandrel guide, wherein the mandrel guide has an open distal end suitable for discharging a substance when loaded therein; and
    (ii) a longitudinally elongated mandrel disposed internally to the mandrel guide, whereby relative longitudinal movement of the mandrel through the mandrel guide towards the open distal end biases the loaded substance to move longitudinally towards the open end;
  (b) a handpiece providing support to the delivery unit, wherein the mandrel or the mandrel guide is not fixed to the handpiece; wherein the mandrel or the mandrel guide is a non-fixed delivery unit member to allow longitudinal movement there about;

(c) a spring that biases the non-fixed delivery unit member for said relative longitudinal of the mandrel through the mandrel guide towards the open distal end;

(d) a delivery unit engagement means fixed to the handpiece that engages and disengages with the non-fixed delivery unit member; and (e) a push button operably linked to the delivery unit engagement means to cause said engagement and disengagement of the delivery unit; wherein:

when the delivery unit engagement means is engaged with the non-fixed delivery unit member, the delivery unit engagement means opposes said spring bias, thereby preventing said relative longitudinal of the mandrel through the mandrel guide towards the open distal end; and when the delivery unit engagement means is disengaged with the non-fixed delivery unit member, the delivery unit engagement means does not oppose said spring bias, thereby not preventing said relative longitudinal of the mandrel through the mandrel guide towards the open distal;

the mandrel can move longitudinally relative to the mandrel guide from a first longitudinal position to a second longitudinal position and to plurality of longitudinal positions intermediate of the first longitudinal position and the second longitudinal position;

the delivery unit engagement means is configured to engage and disengage the non-fixed delivery unit member when the mandrel is at each of the plurality of longitudinal positions relative to the mandrel guide, wherein, by causing the delivery unit engagement means to engage and disengage the non-fixed delivery unit member, the push button can be used to start and stop the longitudinal movement of the mandrel relative to the mandrel guide when the mandrel is at each of the plurality of longitudinal positions relative to the mandrel guide.

19. The device of claim 18, wherein:

the delivery unit engagement means comprises a traction pad wherein said opposing said force on the delivery unit comprises opposing said force on the delivery unit with a friction force; or the delivery unit engagement means comprises a knife edge lock, the delivery unit comprises a ratchet rack comprising a plurality of ratchet teeth, and the engagement of the delivery unit engagement means with the delivery unit comprises engagement of the knife edge lock with a ratchet tooth of the ratchet rack.

20. The device of claim 18, further comprising:

a pin fixed to the non-fixed delivery unit member such that the pin travels along a longitudinal path when the mandrel moves longitudinally relative to the mandrel guide;

a latch disposed laterally of said longitudinal path and fixed in position relative to the handpiece, wherein the pin is configured to be movable from laterally, from said longitudinal path, into the latch, and thereby becomes longitudinally immobilized, wherein said longitudinal movement of the mandrel relative to the mandrel guide is prevented when the pin is longitudinally immobilized by the latch.

21. The device of claim 18 wherein the device comprises a biasing member for biasing the delivery unit engagement means to engage the non-fixed delivery unit member when the delivery unit engagement means is disengaged with the non-fixed delivery unit member; whereby applying a user force to the push button disengages the delivery unit engagement means from the delivery unit to allow the relative longitudinal movement.

22. The device of claim 18, wherein:

a) the mandrel guide comprises a nozzle at a distal end of the mandrel guide;

b) the push button is operably linked to the non-fixed delivery unit member at a location proximal of the nozzle; and c) the push button is operably linked to the non-fixed delivery unit member inside the handpiece.

* * * * *